US011445981B1

United States Patent
Fortney et al.

(10) Patent No.: US 11,445,981 B1
(45) Date of Patent: Sep. 20, 2022

(54) SURVIVAL PREDICTION USING METHYLOMIC PROFILES

(71) Applicant: BioAge Labs, Inc., Berkeley, CA (US)

(72) Inventors: Kristen Patricia Fortney, Crockett, CA (US); Jonah Daniel Sinick, Berkeley, CA (US); Andrew Jarai Ho, Berkeley, CA (US); Yonatan Nissan Donner, Sunnyvale, CA (US)

(73) Assignee: BioAge Labs, Ipc., Richmond, CA (US)

( * ) Notice: Subject to any disclaimer, the term of this patent is extended or adjusted under 35 U.S.C. 154(b) by 387 days.

(21) Appl. No.: 16/040,615

(22) Filed: Jul. 20, 2018

Related U.S. Application Data

(60) Provisional application No. 62/536,827, filed on Jul. 25, 2017.

(51) Int. Cl.
| | |
|---|---|
| *A61B 5/00* | (2006.01) |
| *A61B 5/021* | (2006.01) |
| *A61B 5/107* | (2006.01) |
| *A61B 5/11* | (2006.01) |
| *C12Q 1/6883* | (2018.01) |
| *G16H 50/20* | (2018.01) |
| *G16H 50/30* | (2018.01) |

(52) U.S. Cl.
CPC .......... *A61B 5/7275* (2013.01); *A61B 5/021* (2013.01); *A61B 5/1072* (2013.01); *A61B 5/1118* (2013.01); *C12Q 1/6883* (2013.01); *G16H 50/20* (2018.01); *G16H 50/30* (2018.01); *C12Q 2600/136* (2013.01); *C12Q 2600/154* (2013.01)

(58) Field of Classification Search
CPC .................................................... A61B 5/7275
See application file for complete search history.

(56) References Cited

PUBLICATIONS

Marioni et al., DNA methylation age of blood predicts all-cause mortality in later life, Genome Biol. Jan. 30, 2015;16:25. doi: 10.1186/s13059-015-0584-6.*

Kuo et al., A prognostic predictor panel with DNA methylation biomarkers for early-stage lung adenocarcinoma in Asian and Caucasian populations, Journal of Biomedical Science vol. 23, Article No. 58 (2016).*

Qu et al., Prognostic methylation markers for overall survival in cytogenetically normal patients with acute myeloid leukemia treated on SWOG trials, Cancer. Jul. 1, 2017;123(13):2472-2481. doi: 10.1002/cncr.30626. Epub Feb. 21, 2017.*

Wei et al., A CpG-methylation-based assay to predict survival in clear cell renal cell carcinoma, Nat Commun. Oct. 30, 2015;6:8699. doi: 10.1038/ncomms9699.*

Zhang et al., Smoking-Associated DNA Methylation Biomarkers and Their Predictive Value for All-Cause and Cardiovascular Mortality, Environ Health Perspect. Jan. 2016;124(1):67-74. doi: 10.1289/ehp.1409020. Epub May 27, 2015.*

(Continued)

*Primary Examiner* — Travis R Hunnings
(74) *Attorney, Agent, or Firm* — Fenwick & West LLP

(57) ABSTRACT

In various embodiments, the present description relates to the use of factors related to survival. The methods, compositions and systems described herein may be used to determine factors affecting survival, assess survival risk based on factors related to survival and/or make suggestions to increase the likelihood of survival or extend the period of survival.

19 Claims, 2 Drawing Sheets

(56) References Cited

PUBLICATIONS

Zhang et al., DNA methylation signatures in peripheral blood strongly predict all-cause mortality, Nat Commun 8, 14617 (2017), https://doi.org/10.1038/ncomms14617.*

Breitling L. P. et al. "Frailty is Associated with the Epigenetic Clock But Not With Telomere Length in a German Cohort," Clinical Epigenetics, 2016, 8 pages, vol. 8, No. 21.

Florath I. et al., "Cross-Sectional and Longitudinal Changes in DNA Methylation with Age: An Epigenome-Wide Analysis Revealing Over 60 Novel Age-Associated CpG sites," Human Molecular Genetics, 2014, pp. 1186-1201, vol. 23, No. 5.

Friedman, J.H., "Greedy Function Approximation: A Gradient Boosting Machine," The Annals of Statistics, 2011, pp. 1189-1232, vol. 29, No. 5.

Hannum G. et al., "Genome-Wide Methylation Profiles Reveal Quantitative Views of Human Aging Rates," Molecular Cell, 2013, pp. 359-367, vol. 49.

Horvath, S., "DNA Methylation Age of Human Tissues and Cell Types," Genome Biology, 2013, 19 pages, vol. 14, R115.

Marioni, R. E. et al., "DNA Methylation Age of Blood Predicts All-Cause Mortality in Later Life," Genome Biology, 2015, 12 pages, vol. 16, 25.

Moore, A. Z. et al., "Change in Epigenome-Wide DNA Methylation Over 9 Years and Subsequent Mortality: Results From the InCHIANTI Study," Journals of Gerontology A Biol. Sci. Med. Sci., 2016, pp. 1029-1035, vol. 71.

Polsterl, S. et al., "Fast Training of Support Vector Machines for Survival Analysis," Machine Learning and Knowledge Discovery in Databases, ECML PKDD 2015, Part II, LNAI 9285, A. Appice et al. (Eds.), 2015, pp. 243-259.

Ridgeway, G., "Generalized Boosted Models: A Guide to the GBM Package," Aug. 3, 2007, 12 pages.

Simon et al. "Regularization Paths for Cox's Proportional Hazards Model via Coordinate Descent," Journal of Statistical Software, Mar. 2011, pp. 1-13, vol. 39, No. 5.

Weidner, C. I. et al., "Aging of Blood Can be Tracked by DNA Methylation Changes at Just Three CpG Sites," Genome Biology, 2014, 12 pages, vol. 15, R24.

Zhang, Y. et al., "DNA Methylation Signatures in Peripheral Blood Strongly Predict All-Cause Mortality," Nature Communication, Mar. 17, 2017, pp. 1-11.

* cited by examiner

SURVIVAL PREDICTION USING METHYLOMIC PROFILES

CROSS REFERENCE TO RELATED APPLICATIONS

This application claims benefit to U.S. provisional application No. 62/536,827 filed Jul. 25, 2017, the contents of which are incorporated herein in its entirety by reference thereto.

BACKGROUND

Predicting mortality, i.e. how long an individual's risk of death, and predicting related outcomes such as an individual's future risk of developing an age-related disease, remains very challenging. Human aging is complex and multiple factors play a role, including genetic and environmental factors that are integrated together in the methylome. Predictive biomarkers of mortality are of substantial clinical and scientific interest. They can be applied to help doctors identify and treat populations at increased risk of dying, and to assess human frailty, pace of aging, and the effects of new therapies. Thus, there is a need to identify and use proxies for mortality and survival in many important applications. Specifically, there is a need to find methylomic factors that correlate with survival and/or mortality. There is a further need to have suitable methods to study survival and the effect of various factors on survival in shorter time periods. Also, there is a need to identify drugs and life-style choices that have a positive or negative effect on factors that correlate with survival and/or with mortality. Such drugs may be used to increase survival. The methods and systems described herein, in various embodiments, address these needs in novel and effective ways.

SUMMARY

In a first aspect, the methods, compositions and systems described herein relate to a method for determining a survival metric for a subject. In one embodiment, a computer system for predicting survival likelihood comprises a computer processor and a memory storing a survival predictor model configured to: accept methylation fraction values for n nucleic acid methylation sites relating to i test subjects; and generate a survival metric for each of the i test subjects based on the methylation fraction values for the n nucleic acid methylation sites; wherein the survival predictor model is trained on a training dataset comprising methylation fraction values for m methylation sites relating to j training subjects. In some embodiments, the survival predictor model is nonlinear.

In some embodiments, the survival predictor model is trained with a Cox proportional hazard loss function. In some embodiments, the survival predictor model is trained by gradient boosting. In some embodiments, the survival predictor model is trained using elastic net regression. In some embodiments, the training dataset further comprises values for k clinical factors. In some embodiments, the clinical factors are selected from the group consisting of age, sex, systolic blood pressure, diastolic blood pressure, high cholesterol status, cardiovascular disease status, high blood sugar status, smoking status, alcohol consumption status, the number of cigarettes smoked per day, period lived as a smoker, frequency of alcohol consumption, daily amount of alcohol consumption, time spent engaging in mild physical activity, time spent engaging in moderate physical activity, time spent engaging in heavy physical activity, race, ethnicity, diastolic blood pressure, systolic blood pressure, height, weight, a body mass index, resting heart rate, a family history parameter, a medical history parameter, and a medical symptom parameter. In some embodiments, the survival predictor model is further configured to accept values for l clinical factors and to generate a survival metric for the i test subjects based on the l clinical factors. In some embodiments, the l clinical factors are selected from the group consisting of age, sex, systolic blood pressure, diastolic blood pressure, high cholesterol status, cardiovascular disease status, high blood sugar status, smoking status, alcohol consumption status, the number of cigarettes smoked per day, period lived as a smoker, frequency of alcohol consumption, daily amount of alcohol consumption, time spent engaging in mild physical activity, time spent engaging in moderate physical activity, time spent engaging in heavy physical activity, race, ethnicity, diastolic blood pressure, systolic blood pressure, height, weight, a body mass index, resting heart rate, a family history parameter, a medical history parameter, and a medical symptom parameter. In some embodiments, i is at least 1, 2, 3, 4, 5, 6, 7, 8, 9, 10, 15, 20, 30, 40, 50, 100, 500, 1000, or more. In some embodiments, j is at least 5, 10, 20, 50, 100, 200, 250, 300, 350, 400, 450, 500, 750, 1000, 1500, 2000, 3000, 5000, 10000, 20000, 50000, or more. In some embodiments, n is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 90, 100, 110, 120, 130, 140, 150, 160, 170, 180, 190, 200, or more. In some embodiments, m is at least 2, 3, 4, 5, 10, 50, 100, 500, 1000, 5000, 10000, 25000, 50000, 100000, 250000, 300000, 350000, 400000, 450000, 500000, 750000, 1000000, 2000000, 3000000, 4000000, 5000000, or more.

In some embodiments, k is at least 1, 2, 3, 4, 5, 6, 7, 8, 9, 10, 11, 12, 13, 14, 15, 20, 25, 30, 40, 50, or more. In some embodiments, l is at least 1, 2, 3, 4, 5, 6, 7, 8, 9, 10, 11, 12, 13, 14, 15, 20, 25, 30, 40, 50, or more. In some embodiments, the survival predictor model yields a Harrell's concordance index of greater than 0.5926, 0.612, 0.7105, 0.7110, 0.7134, 0.7210, 0.7248, 0.7258, 0.7318, 0.7325, 0.7382, 0.7435, 0.7439, 0.7472, 0.7492, 0.7574, 0.7581, 0.7662, 0.7393, 0.7472, 0.7531, 0.7539, 0.7595, 0.7725, 0.7769, 0.7789, 0.7829, 0.7872, 0.7947, 0.8000 or more for the training dataset. In some embodiments, the methylation fraction values for the n nucleic acid methylation sites are derived from a blood sample. In some embodiments, the methylation fraction values for the n nucleic acid methylation sites relating to i test subjects are derived from a blood sample. In some embodiments, the methylation fraction values for the m nucleic acid methylation sites relating to j training subjects are derived from a blood sample. In some embodiments, the i test subjects are human. In some embodiments, the j training subjects are human. In some embodiments, the j test subjects are drawn from one of the Offspring cohort of the Framingham Heart Study (Example 1, 15) and the Normative Aging Study (Example 14, 16). In some embodiments, the training dataset consists of subjects having a preset value for a screening clinical factor. In some embodiments, the screening clinical factor is gender. In some embodiments, the value for the clinical factor is preset to male. In some embodiments, the survival metric is indicative of the subject's relative survival risk. In some embodiments, the survival metric is indicative of the subject's relative likelihood of contracting an aging-related disease, chance of survival, or chance of death. In certain embodiments, the n nucleic acid methylation sites of the survival predictor model comprise y nucleic acid methylation sites identified using a first dataset and a first modeling technique, and n-y nucleic acid methylation sites identified using a second dataset and a second modeling technique. In certain embodiments, the first dataset is different from the second dataset, the first modeling technique is different from the second modeling technique, or combinations thereof. In some embodiments, the nucleic acid methylation sites include at least two or more of cg05575921, cg06126421, cg08362785, cg10321156, cg14975410, cg19572487, cg23665802, cg24704287 and cg25983901. In some embodiments, the nucleic acid methylation sites include at least two or more of cg26987613, cg00252813 and cg07890785. In some embodiments, the nucleic acid methylation sites include at least two or more of cg02679745, cg15814508, cg20430631, and cg00984060. In some embodiments, the nucleic acid methylation sites includes cg05575921. In some embodiments, the nucleic acid methylation sites includes cg06126421. In some embodiments, the nucleic acid methylation sites includes cg08362785. In some embodiments, the nucleic acid methylation sites includes cg10321156. In some embodiments, the nucleic acid methylation sites includes cg14975410. In some embodiments, the nucleic acid methylation sites includes cg19572487. In some embodiments, the nucleic acid methylation sites includes cg23665802. In some embodiments, the nucleic acid methylation sites includes cg24704287. In some embodiments, the nucleic acid methylation sites includes cg25983901. In some embodiments, the nucleic acid methylation sites includes cg26987613. In some embodiments, the nucleic acid methylation sites includes cg00252813. In some embodiments, the nucleic acid methylation sites includes cg07890785. In some embodiments, the nucleic acid methylation sites includes cg02679745. In some embodiments, the nucleic acid methylation sites includes, cg15814508. In some embodiments, the nucleic acid methylation sites includes cg20430631. In some embodiments, the nucleic acid methylation sites includes cg00984060. In some embodiments, the nucleic acid methylation sites include at least two or more of the nucleic acid methylation sites of Table 1. In some embodiments, the nucleic acid methylation sites include at least two or more of the nucleic acid methylation sites of Table 2. In some embodiments, the nucleic acid methylation sites include at least two or more of the nucleic acid methylation sites of Table 3. In some embodiments, the nucleic acid methylation sites include at least two or more of the nucleic acid methylation sites of Table 4. In some embodiments, the nucleic acid methylation sites include at least two or more of the nucleic acid methylation sites of Table 5. In some embodiments, the nucleic acid methylation sites include at least two or more of the nucleic acid methylation sites of Table 6. In some embodiments, the nucleic acid methylation sites include at least two or more of the nucleic acid methylation sites of Table 7. In some embodiments, the nucleic acid methylation sites include at least two or more of the nucleic acid methylation sites of Table 8. In some embodiments, the nucleic acid methylation sites include at least two or more of the nucleic acid methylation sites of Table 9. In some embodiments, the nucleic acid methylation sites include at least two or more of the nucleic acid methylation sites of Table 10. In some embodiments, the nucleic acid methylation sites include at least two or more of the nucleic acid methylation sites of Table 11.

In one embodiment, a method for predicting survival likelihood comprises receiving methylation fraction values for n nucleic acid methylation sites relating to i test subjects; and generating, using a survival predictor model, a survival metric for each of the i test subjects based on the methylation fraction values for the n nucleic acid methylation sites; wherein the survival predictor model is trained on a training dataset comprising methylation fraction values for m methylation sites relating to j training subjects. In some embodiments, the method further comprises generating a life insurance policy for each of the i test subjects based on the survival metric.

In one embodiment, a non-transitory computer readable storage medium comprises computer program instructions that when executed by a computer processor cause the processor to: receive methylation fraction values for n nucleic acid methylation sites relating to i test subjects; and generate, using a survival predictor model, a survival metric for each of the i test subjects based on the methylation fraction values for the n nucleic acid methylation sites; wherein the survival predictor model is trained on a training dataset comprising methylation fraction values for m methylation sites relating to j training subjects.

In one embodiment, a kit for determining survival risk in a subject comprises: a set of reagents for generating via at least one assay a dataset associated with a sample from the subject comprising presence and/or abundance and/or degree of methylation of one or more survival biomarkers.

In one embodiment, a method of drug screening comprises: contacting one or more biological samples with a test compound; obtaining a dataset associated with the one or more biological samples representing presence and/or abundance and/or degree of methylation of one or more survival biomarkers; calculating a survival metric that is dependent on the dataset; and designating the test compound as an anti-aging drug candidate, if the survival metric falls within a pre-designated range.

BRIEF DESCRIPTION OF THE DRAWINGS

These and other aspects and features of the present invention will become apparent to those ordinarily skilled in the art upon review of the following description of specific embodiments of the invention in conjunction with the accompanying figures, wherein.

DETAILED DESCRIPTION OF THE PREFERRED EMBODIMENTS

Advantages and Utility

Figure 1:
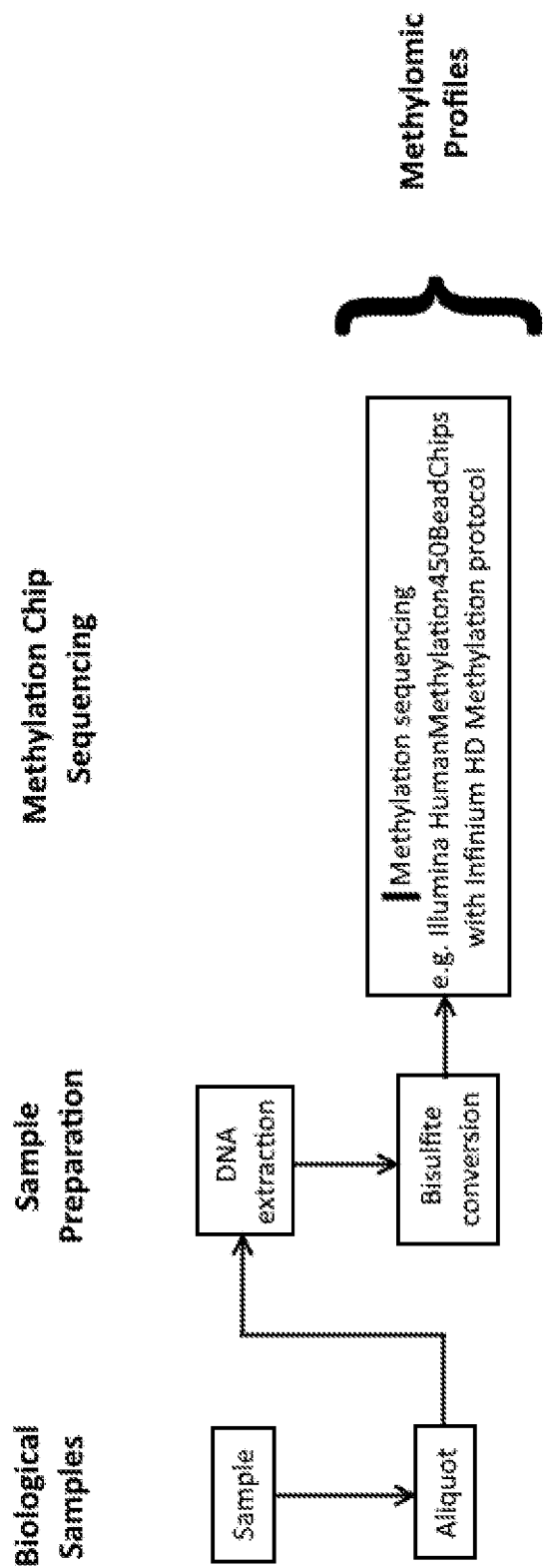
FIG. 1 depicts an exemplary illustration of a methylation study where methylation markers can be tracked in samples from one or more subjects.

This description, in various embodiments, relate to identification of methylomic features and/or methylation marker identities that correlate with all-cause mortality. Methods described herein allow for the selection of those biomarkers. Survival biomarkers may be used to build survival predictor models capable of determining the value for a survival metric given information regarding the abundance and/or presence (and/or absence) and/or the degree of methylation of those biomarkers in an individual, for example in a sample obtained from an individual. Survival metrics are used to predict survival related values, such as time to an aging event. An aging event may comprise the occurrence of an aging related condition, such as death or contraction of an aging related disease, including, without limitation, cardiovascular disease, angina, myocardial infarction, stroke, heart failure, hypertensive heart disease, hypertension, cardiomyopathy, heart arrhythmia, valvular heart disease, aortic aneurysms, peripheral artery disease, venous thrombosis, atherosclerosis, coronary artery disease, cancer, Type 1 diabetes, Type 2 diabetes, chronic obstructive pulmonary disease ("COPD"), stroke, arthritis, cataracts, macular degeneration, osteoporosis, fibrotic diseases, sarcopenia, osteoporosis, cognitive decline, dementia and/or Alzheimer's. Survival related values may be predicted in an absolute or relative fashion. This description also relates to determining the relative effect of a factor, such as, without limitation, a drug or a lifestyle choice, on a survival related value.

The principles described herein are useful for determining a survival metric for a subject from an analysis of a biological sample. The methods and compositions described herein may rely on one or more survival biomarker detection assays to analyze biological sample to identify information that can be used in determining the survival metric. The principles described herein are further useful for determining survival biomarkers and/or building survival predictor models that rely on those identified survival biomarkers for the prediction of the survival metric. Survival predictor models may be built with any plurality of biomarkers identified herein, in particular in Tables 1-5. The principles described herein are further useful for identifying drugs or life-style changes that have an effect on survival biomarkers and/or a survival metric predicted according to the methods and compositions described herein.

In addition to methods and compositions, embodiments include using a processor in conjunction with a non-transitory computer readable storage medium to create, store, process, access, and otherwise use data, models, and other computer instructions related to survival biomarkers or survival predictor models.

DEFINITIONS

Terms used in the claims and specification are defined as set forth below unless otherwise specified.

The term "ameliorating" refers to any therapeutically beneficial result in the treatment of a disease state, in extending life expectancy, or in decreasing the effect of a factor in all-cause mortality, e.g., an aging related disease state, including prophylaxis, lessening in the severity or progression, remission, or cure thereof.

The term "sufficient amount" means an amount sufficient to produce a desired effect, e.g., an amount sufficient to modulate protein aggregation or modulate protein signaling in a cell.

The term "therapeutically effective amount" is an amount that is effective to ameliorate a symptom of a disease, a cause of mortality, aging or an aging related disease or a factor that correlates with mortality, aging or aging related disease. A therapeutically effective amount can be a "prophylactically effective amount" as prophylaxis can be considered therapy.

It must be noted that, as used in the specification and the appended claims, the singular forms "a," "an" and "the" include plural referents unless the context clearly dictates otherwise.

A "subject" or an "individual" in the context of the present teachings is generally an animal, e.g. a mammal. The subject can be a human patient, e.g., a human having an increased risk of mortality. The term "mammal" as used herein includes but is not limited to a human, non-human primate, canine, feline, murine, bovine, equine, and porcine.

Mammals other than humans can be advantageously used as subjects that represent animal models of, e.g., aging. A subject can be male or female. A subject can be one who has been previously diagnosed or identified as having an aging related disease. A subject can be one who has already undergone, or is undergoing, a therapeutic intervention for aging related disease. A subject can also be one who has not been previously diagnosed as having aging related disease; e.g., a subject can be one who exhibits one or more symptoms or risk factors for aging related disease, or a subject who does not exhibit symptoms or risk factors for aging related disease, or a subject who is asymptomatic for aging related disease.

A "sample" in the context of the present teachings refers to any biological sample that is isolated from a subject. A sample may comprise a single cell or multiple cells, fragments of cells, an aliquot of body fluid, whole blood, platelets, serum, plasma, red blood cells, white blood cells or leucocytes, endothelial cells, a tissue, a tissue extract, a tissue biopsy, synovial fluid, lymphatic fluid, ascites fluid, bronchoalveolar lavage, interstitial or extracellular fluid, the fluid in spaces between cells, including gingival crevicular fluid, bone marrow, cerebrospinal fluid (CSF), saliva, mucous, sputum, semen, sweat, urine, or any other bodily fluid, a swab, or extracts thereof. "Blood sample" can refer to whole blood or any fraction thereof, including blood cells, red blood cells, white blood cells or leucocytes, platelets, serum and plasma. Samples can be obtained from a subject by any suitable method, including but not limited to venipuncture, excretion, ejaculation, massage, biopsy, needle aspirate, lavage, scraping, surgical incision, or intervention or any other suitable method known in the art. In one embodiment the sample is a whole blood sample. A sample can include protein extracted from blood of a subject.

To "analyze" includes measurement and/or detection of data associated with a methylation marker or biomarker (such as, e.g., presence or absence of a methylation marker feature or methylation marker) in the sample (or, e.g., by obtaining a dataset reporting such measurements, as described in further detail elsewhere herein). In some aspects, an analysis can include comparing the measurement and/or detection against a measurement and/or detection in a sample or set of samples from the same subject or other control subject(s). The methylation marker features and methylation marker identities of the present teachings can be analyzed by any of the various conventional methods known in the art.

Methylation site features may be used to characterize, identify, or otherwise analyze methylation markers. A feature can be a collection of data points, e.g. raw color channel intensities for the methylated and unmethylated form of a methylation site, a region in a mass spectrum and time, and/or other metadata about the methylation site, including information about the biological relevance of the methylation marker. Methylation site features may be obtained through standardized methylomics methods and methylomics data reporting. Methylation site features may also be linked to methylation marker databases or epigenome databases, e.g., Database of CpG Islands (dbcat.cgm.nt-u.edu.tw/), MEC Data Portal (epigenomesportal.ca/ihec/), Roadmap Epigenomics (egg2.wustl.edu/roadmap/web_portal/), CEEHRC Platform (www.epigenomes.ca/data-release/), DeepBlue (deepblue.mpi-inf mpg.de/), Human Epigenome Atlas (www.genboree.org/epigenomeatlas/index.rhtml), MethylomeDB (www.neuroepigenomics.org/ methylomedb/), UHN Human CpG Island Microarray Database (www.pmgenomics.ca/cpg/), MethDB (www.methdb.de/), and others to facilitate data processing and interpretation.

A "dataset" is a set of data (e.g., numerical values) resulting from evaluation of a sample (or population of samples) under a desired condition. The values of the dataset can be obtained, for example, by experimentally obtaining measures from a sample and constructing a dataset from these measurements; or alternatively, by obtaining a dataset from a service provider such as a laboratory, or from a database or a server on which the dataset has been stored. Similarly, the term "obtaining a dataset associated with a sample" comprises obtaining a set of data determined from at least one sample. Obtaining a dataset may comprise obtaining a sample, and/or processing the sample to experimentally determine the data, e.g., via measuring, such as by mass spectrometry and/or computationally processing data that was measured from a sample. Obtaining a dataset associated with a sample may comprise receiving a set of data, e.g., from a third party that has processed the sample to experimentally determine the dataset. In some embodiments, obtaining a dataset associated with a sample comprises mining data from at least one database or at least one publication or a combination of at least one database and at least one publication.

"Measuring" or "measurement" in the context of the present teachings refers to determining the presence, absence, quantity, amount, or effective amount of a substance in a clinical or subject-derived sample, including the presence, absence, or concentration levels of such substances, and/or evaluating the values or categorization of a subject's clinical parameters based on a control.

The term "FDR" means false discovery rate. FDR may be estimated by analyzing randomly-permuted datasets and tabulating the average number of methylation markers at a given p-value threshold.

This description generally relates to identification and quantification of methylation markers that correlate with all-cause mortality. Such methylation markers and/or methylation marker identities may be determined by use of methylomics analysis. Methylomics analysis, in various embodiments, comprises detection of changes in the degrees of methylation of methylation at specified CpG sites in subjects or groups of subjects that have differing survival periods, survival expectancies, and/or risk of death.

This description also relates to building of survival predictor models that output a survival metric. Such survival metrics may relate to survival related observables, such as survival expectancy and/or risk of death. In various embodiments, survival predictor models may be built by selecting methylation marker features that strongly associate with survival periods ("survival biomarkers") or other observables that relate to survival periods ("aging indicator"). Such aging indicators may comprise variables that correlate with all-cause mortality, such as certain clinical factors. In some embodiments, survival predictor models utilize one or a plurality of survival biomarkers together with one or more aging indicators to generate a survival metric.

Survival biomarkers may be selected by conducting a cohort study. The cohort study may be designed such that certain variables that strongly correlate with survival are absent from the study. For example, individuals with major age-related diseases, such as, without limitation, hypertensive heart disease, Type 2 diabetes, coronary artery disease, cancer, Type 1 diabetes, chronic obstructive pulmonary disease (COPD), history with stroke, and/or Alzheimer's, at the time of sample collection may be excluded from the study cohort. A range of data about the cohort subjects, such as, without limitation, information from their health history, such as age, gender, smoking status, alcohol consumption status, height, weight, BMI, and blood pressure metrics, may be used as aging indicators to build a survival predictor model and/or to select survival biomarkers. In various embodiments, a list of survival biomarkers is prepared by correlation with aging indicators and/or with survival.

Methylomic Profiles

The distribution of methylation sites, the presence and/or abundance of methylation at methylation sites, and/or CpG site methylation fractions (as a way of quantifying methylation at CpG sites) may be determined using methylomic profiling. Methylomic profiling may comprise characterization and/or measurement of CpG sites in the DNA contained within a biological sample, according the methods and compositions described herein in various embodiments. Biological samples may include, without limitation, a single cell or multiple cells, fragments of cells, an aliquot of body fluid, whole blood, platelets, serum, plasma, red blood cells, white blood cells or leucocytes, endothelial cells, a tissue, a tissue extract, a tissue biopsy, synovial fluid, lymphatic fluid, ascites fluid, bronchoalveolar lavage, interstitial or extracellular fluid, the fluid in spaces between cells, including gingival crevicular fluid, bone marrow, cerebrospinal fluid (CSF), saliva, mucous, sputum, semen, sweat, urine, or any other bodily fluid, a swab, or extracts thereof.

A methylation profile or methylomic profile may include information such as the quantity and/or type of CpG sites present in a sample and/or the methylation fraction of one or more CpG sites. Methylation profiles may vary in complexity and information content. In some embodiments, a methylation profile can be determined using a single technique. In other cases, several different techniques may be used in combination to generate a methylation profile.

The complexity and information content of a methylation profile can be chosen to suit the intended use of the profile. For example, the complexity and information content may be chosen according to the disease state of the test individuals, the disease state to be predicted, the types of small molecules present in an assayed biological sample, such as, without limitation, a single cell or multiple cells, fragments of cells, an aliquot of body fluid, whole blood, platelets, serum, plasma, red blood cells, white blood cells or leucocytes, endothelial cells, a tissue, a tissue extract, a tissue biopsy, synovial fluid, lymphatic fluid, ascites fluid, bronchoalveolar lavage, interstitial or extracellular fluid, the fluid in spaces between cells, including gingival crevicular fluid, bone marrow, cerebrospinal fluid (CSF), saliva, mucous, sputum, semen, sweat, urine, or any other bodily fluid, a swab, or extracts thereof The methylation profile may comprise and/or be or have been created so as to give information about the presence and/or abundance of one or more CpG sites or classes of CpG sites and/or to give information about the absolute or relative distribution of CpG sites or classes of CpG sites and/or the methylation fraction and/or the abundance, absolute distribution, or relative distribution of methylation fraction of some or all of the CpG sites measured. For example, the methylation profile may comprise and/or be or have been created so as to give information about the methylation fractions of a plurality of CpG sites or classes of CpG sites, for example, about or at least about 2, 3, 4, 5, 6, 7, 8, 9, 10, 12, 15, 20, 25, 30, 50, 75, 100, 250, 500, 1000, 2000, 3000, 4000, 5000, 10000, 20000, 30000, 40000, 50000, 75000, 100000, 200000, 300000, 400000, 500000, 750000, 1000000, 2000000, 3000000, 4000000, 5000000 or more CpG sites.

FIG. 1 illustrates an example for creation of methylation profiles according to various embodiments. The creation of methylation profiles may start with biological sample collection. Sample collection may take place immediately before subsequent analysis steps. In some embodiments, samples are collected over time. One or more samples may be collected from each individual. The samples collected from some or all of the individuals in a group of individuals may be collected as a time series to create longitudinal data about a subset or all of the individuals in the group. The time series may be set so as to start at a certain start time and comprise periodic intervals. The periodic intervals may be linear, semi-linear, comprise decreasing or increasing interval lengths, or be random. The start time may be set at a particular point in time, at a particular age, or be random for some or all of the individuals. About or at least about 1, 2, 3, 4, 5, 6, 7, 8, 9, 10, 12, 15, 20, 25, 30, 40, 50, 75, 100 or more samples may be collected from each individual. The biological sample may comprise any suitable sample type, such as, without limitation, a single cell or multiple cells, fragments of cells, an aliquot of body fluid, whole blood, platelets, serum, plasma, red blood cells, white blood cells or leucocytes, endothelial cells, a tissue, a tissue extract, a tissue biopsy, synovial fluid, lymphatic fluid, ascites fluid, bronchoalveolar lavage, interstitial or extracellular fluid, the fluid in spaces between cells, including gingival crevicular fluid, bone marrow, cerebrospinal fluid (CSF), saliva, mucous, sputum, semen, sweat, urine, or any other bodily fluid, a swab, or extracts thereof.

The analysis of the biological samples or specimens described herein may involve one or more analysis methods. In some embodiments, biological samples or specimens described herein are split into aliquots. In some embodiments, genomic material such as DNA is extracted from the biological samples or specimens described herein or their derived aliquots. For example, analytic methods suitable to differentiate or differentially elute the different constituents of human blood or another type of biological sample or specimen may be utilized to isolate the fractions of those constituents in the biological samples or specimens described herein. Additionally, the isolated constituents of biological samples may be subjected to one or multiple extraction techniques suitable for the biological nature of the isolated constituent. In some embodiments, the extraction of genomic material is performed upon the biological samples or specimens described herein, such as upon a whole blood sample. In some embodiments, the extraction of genomic material is performed upon one, some, or all of the separated constituents of the biological samples or specimens described herein, such as upon peripheral blood lymphocytes or upon buffy coat. In some embodiments, the extracted genomic material is prepared for methylation sequencing via the method of bisulfite conversion (e.g. with the EZ-96 DNA Methylation Kit (Zymo Research, Orange, Calif., USA)), polymerase chain reaction (PCR) amplification, PCR purification enzyme digestion, end repair, A-tailing, sequence adapter ligation, fragment purification, and/or other suitable methods known to those skilled in the art.

The genomic material that is extracted and/or prepared with the method of bisulfite conversion and/or methods as described in further detail elsewhere herein may be further analyzed using methylation sequencing via a methylation chip (e.g. with Illumina HumanMethylation450BeadChips using the Infinium HD Methylation protocol and Tecan robotics with the Illumina Infinium Methylation Assay (Illumina, San Diego, Calif., USA)). The methylomic data that are acquired via methylation sequencing may be further analyzed using a suitable data analysis method. In some embodiments, the methylomic data are subjected to sequence alignment and/or analysis with a suitable data analysis method known in the art (e.g. Maq, BS Seeker, Bismark, or BSMAP).

Methylation profiles may be generated by one or more suitable method, including, without limitation, bisulfite sequencing, polymerase chain reaction (PCR), direct sequencing, bisulfite pyrosequencing, methylation-sensitive single-strand conformation analysis (MS-SSCA), high resolution melting analysis (HRM), methylation-sensitive single-nucleotide primer extension (MS-SnuPE), base-specific cleavage, matrix-assisted laser desorption ionization/time-of-flight (MALDI-TOF) mass spectrometry, methylation-specific PCR (MSP), microarray-based methods, genome-wide methylation analysis, oxidative bisulfite sequencing, reduced representation bisulfite sequencing (RRBS), shotgun bisulfite sequencing (MethylC-seq), methylated DNA immunoprecipitation sequencing (MeDIP-seq), methylated DNA binding domain sequencing (MBD-seq), methylation-sensitive restriction enzyme (MRE-seq), clonal bisulfite sequencing, Sanger sequencing, 36-base single-end sequencing reads, MethyLight, mass spectrometry (MS), liquid chromatography-mass spectrometry (LC-MS), and/or any other suitable methods known in the art, or combinations thereof.

Data Cleaning

In some embodiments, certain CpG markers are identified and filtered from the methylation data after sequencing on a methylation chip. For example, outliers may be identified with quality control plots, principal component analysis (PCA) plots, and/or any other suitable methods known in the art or combinations thereof, and identified outliers may be removed from the methylation data. In some embodiments, the identification of data to remove is performed qualitatively or visually, e.g. by examining a graph produced by PCA, and/or any other suitable method known in the art, or combinations thereof. In some embodiments, the identification of data to remove is performed with the use of quantitative thresholds, mathematical analysis, and/or any other suitable method known in the art, or combinations thereof. For example, data corresponding to values over or under specified numerical thresholds may be removed. For another example, data with values on one, some or all dimensions more than n measures of statistical variance (e.g. standard deviation, standard error, or variance) away from some measure of statistical centrality (e.g. mean, median, or mode) computed from the entire set of data or subsets of the entire set of data may be removed, where the measure of statistical variance and statistical centrality may include all those known in the art or combinations thereof. The n measures of statistical variance may equal to, about, or at least 0.1, 0.2, 0.3, 0.4, 0.5, 0.6, 0.7, 0.8, 0.9, 1.0, 1.5, 2.0, 2.5, 3.0, 3.5, 4.0, 5.0, 10.0, 15.0 measures of statistical variance, or greater, or values exceeding, lesser to, or in between any of the aforementioned numerical thresholds. In some embodiments, the identification of data to remove is performed using a combination of qualitative and quantitative methods, including those previously mentioned, and including any other suitable methods known in the art, or combinations thereof. In some embodiments, the data are transformed with statistical or computational methods. For example, background correction and normalization techniques may be applied to the methylation data. For example, background correction and normalization may be performed with multi-array analysis, Bayesian modeling, Gaussian process regression, quantile normalization, locally weighted scatterplot smoothing (LOESS), rank inverse normal transformation, internal control normalization, logarithm and power transformations, or other suitable methods known in the art, or combinations thereof. In some embodiments, background correction, normalization, and/or other statistical transformations are performed relative to a subset of the data, such as relative to one or multiple internal standards, internal references, or reference datasets.

In some embodiments, principal component analysis (PCA) is used in the data cleaning process, in the model fitting process, and/or in other steps of the data analysis process, including in the creation of survival predictor models. In the method of principal component analysis, the data may be expressed as a matrix X with the individuals represented by the rows and the variables represented by the columns, and the matrix of principal components is given by $T=X*W$, where X is the aforementioned matrix of data, the operation * represents standard matrix multiplication, and W is a square matrix of dimension p-by-p (where p is equal to the number of variables in X) with its columns being the eigenvectors of $X^T*\lambda$ where $X^T$ denotes the transpose of the matrix X. In some embodiments, the columns of the matrix X are scaled (e.g. by a linear transformation such that their means are equal to 0, and/or such that their standard deviations are equal to 1) prior to the calculation of the matrix T. The first n columns of T, with the numbering beginning at 1 from the leftmost column and proceeding rightward, may be denoted as the "first n principal components (PCs)" of the data. Calculation of the matrix T, and/or of other mathematically equivalent formulations of the principal components of the data, may be performed with statistical or mathematical software, such as Python, R, Mathematica, NumPy, SciPy, Julia, Fortran, and/or other suitable methods known to those skilled in the art.

Methods

In various embodiments, the methods and compositions described herein comprise use of methylation sequencing methods alone or in combination. For example, aliquots of the same sample may be analyzed using each aliquot in a different methylation sequencing method. Methylation sequencing methods may target different methylation sites, methylation site types or classes.

Genetic material in an aliquot may be extracted using a suitable method, such as, without limitation, salt precipitation, ethanol precipitation, isopropanol precipitation, odium acetate precipitation, general alcohol precipitation, or affinity precipitation.

Data acquisition on a methylation chip may result in data files comprising raw intensity information for red, green, and/or other color channels. The data files may comprise information on raw color channel information for both the methylated and unmethylated form of each CpG site. For methylation sequencing methods, data files may comprise raw color channel intensity measured over time. Relative quantitation and/or identification of methylation markers may comprise processing and transforming the raw color channel information at each CpG site for both unmethylated and methylated forms. For example, relative quantification may comprise the computation of $M/(M+U+100)$ for each CpG site, where M denotes the strength of the methylated signal and U denotes the strength of the unmethylated signal, and M and U are computed from the raw color channel information. Relative quantification may also comprise the computation of other functions of M and U and/or transformations of the raw color channel information not expressible as a function of M and U alone. Such processing may be performed with any suitable software known in the art.

Predictors

This section relates to generating a survival predictor model, as well as using the survival predictor model to determine the value for a survival metric for a subject based on the survival predictor model and at least one sample from a subject. Survival predictor models described herein may use one or more survival biomarkers and/or one or more aging indicators. In various embodiments, survival predictor models use at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more survival biomarkers.

Models of all-cause mortality are used to build predictors and/or to use predictors for survival. Suitable statistical models for the predictor models described herein can take a variety of forms, including, without limitation, survival models, such as a model based on a hazard function comprising a generalized gamma distribution, exponential distribution, a Weibull distribution, a Gompertz distribution, a gamma distribution, a log-logistic distribution, or an exponential-logarithmic distribution, with or without frailty. In various embodiments a Cox model, such as a Cox proportional hazards (CoxPH) or an accelerated failure time model is used for a survival predictor model. In some cases, tree-structured survival models comprising a regression tree or classification tree, such as a survival random forest can be used. Further, in some cases a predictor model is built using Support Vector Machines, quadratic discriminant analysis, a LASSO, ridge regression, or elastic net regression model, or neural networks.

Survival predictor models may be built in supervised or unsupervised fashion. Regularization and/or clustering methods may be used to build the predictor models described herein. Parametric or semiparametric mathematical models may be used to build predictor models. Mathematical models may be fit to a dataset using any suitable method known to a person of ordinary skill, including without limitation, gradient-based optimization, constrained optimization, maximum likelihood optimization and variations thereof, Bayesian inference methods, Newton's method, gradient descent, batch gradient descent, stochastic gradient descent, cyclical coordinate descent, or a combination thereof.

Predictor Performance

The performance of a survival predictor model may be assessed using a suitable method known in the art. In various embodiments, two or more survival predictor models are compared based on their assessed performance.

A variety of measures can be used to quantify the predictive discrimination of the survival predictor models discussed herein, including, without limitation, Hazard Ratio ("HR"), area under the curve (AUC), Akaike's Information Criterion (AIC), Harrell's concordance index c, or a likelihood-ratio based statistic such as a $\chi^2$ test, Z-test, or G-test, or any other suitable measure known to a skilled person in the art.

A suitable concordance measure may be used to evaluate the overall performance of the survival predictor model. The concordance measure may be based on an explicit loss function between the predictor model output and the dataset, such as the survival time or on rank correlations between these quantities. For example, Harrell's concordance index c may be used as a rank-correlation measure. In various embodiments, survival predictor models described herein have a Harrell's concordance index that is at least or at least about 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, 0.99, or higher. Survival predictor models may have a Harrell's concordance index of at most or at most about 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, or 0.99. Survival times in the presence of censoring may be ordered by assigning probability scores to pairs in which ordering is not obvious due to censoring, for example by the use of a pooled Kaplan-Meier estimate for event times. Alternative statistics may consider only usable pairs of predicted and measured data and calculate the proportion of concordant pairs among them. Usable pairs maybe selected excluding ties and/or censored data.

In some embodiments, predictive model performance is characterized by an area under the curve (AUC). In some embodiments, predictor model performance is characterized by an AUC greater than or greater than about 0.50, 0.51, 0.52, 0.60, 0.68, 0.70, 0.75, 0.79, 0.80, 0.81, 0.85, 0.89, 0.90, 0.95, 0.99, or greater. In some embodiments, predictor model performance is characterized by an AUC less than or less than about 0.99, 0.95, 0.90, 0.89, 0.85, 0.81, 0.80, 0.79, 0.75, 0.70, 0.68, 0.60, 0.52, 0.51 or less. The AUC of a predictor model may fall in a range having upper and lower bounds defined by any of the foregoing values; e.g. the AUC of a predictor model may be between 0.51-0.95.

In various embodiments, Akaike's Information Criterion (AIC) can be used to measure a predictor model M's performance having k parameters to be estimated. AIC can be expressed as a function of the log likelihood, or deviance, of the model adjusted by the number of parameters in the model:

AIC=2k−2 ln(L), wherein L represents the maximized value of the likelihood function of a model M, i.e. L=p(x|θ,M) where θ are the parameter values that maximize the likelihood function; x represents observed data; and k represents the number parameters in a model M. For survival predictor models, AIC can be expressed as AIC=−2 log(L)+2(i+2+k), where i=0 for the exponential model, i=1 for the Weibull, log-logistic and log-normal models, and i=2 for the generalized gamma model. In some embodiments, x represents instead of the observed data, some or all of the principal components of the observed data.

In some embodiments, a predictor model M's performance is expressed as a corrected AIC (AIC$_c$). Generally, AIC$_c$, as a correction for finite sample sizes, relates to AIC while imposing a penalty for extra parameters. Thus, model fitting methods using AIC$_c$ as a measure of model performance may have a decreased chance of selecting models that have too many parameters, i.e. of overfitting. Suitable expressions of AIC$_c$ can be selected based on the type of the statistical model used and are known in the art.

In various embodiments, survival times are used as a metric for all-cause mortality in a group of subjects. The relationship of one or more covariates and the survival time T can be modeled using the Cox proportional hazards (CoxPH) function as $h_i(t|\beta,h_0)=h_0(t)\exp(x_i'\beta)$ where $h_0(\cdot) \geq 0$ is a baseline hazard function and $\beta=(\beta_1, \ldots, \beta_{p_x})'$ denotes the $p_x$-dimensional vector of regression coefficients associated to the time-independent covariates $x_i=x_{i1}, \ldots, xp_x)' \subset v_i$. In some embodiments, the time-independent covariates comprise some or all of the principal components of the observed data. The impact of the covariates is subsumed in the predictor $\eta=\eta_i(\beta)=x_i'\beta$, which acts through the exponential function. The hazard ratio of two individuals with covariates $x_i$, $x_j$, i≠j can be denoted as $$\frac{h_i(t|\beta, \lambda_0)}{h_j(t|\beta, \lambda_0)} = \exp(\eta_i - \eta_j) = \exp((x_i - x_j)'\beta)$$

Using CoxPH as the model function, some embodiments optimize a regularized objective function which can be expressed as follows:

$\lambda\|\beta\|^2+\Sigma_{i:C_i=1} \log \theta_i - \log(\Sigma_{j:Y_j \geq Y_i}\theta_j)$ where $C_i$ is 1 for occurred events (e.g. deaths) and 0 for censored, $Y_i$ are the event times, $\lambda$ is the regularization coefficient, which can be chosen using cross validation, $\theta_i = \exp(\beta^T X_i)$, $\beta$ represent the Cox weights (that are being optimized, as introduced in the prior paragraph) for $X_i$, the independent variables for individual i. In various embodiments, the independent variables represent values for clinical factors and/or methylation sites, such as in the form of methylation marker normalized scores, which may be obtained from one or more samples from one or more subjects. In some embodiments, the independent variables represent some or all of the principal components of the observed data.

In some embodiments, regularization penalties may use lasso or ridge regression penalty or a combination thereof, such as an elastic net penalty. An elastic net penalty may be expressed as follows:

$$\lambda P_\alpha = (\beta) = \lambda \left( \alpha \sum_{i=1}^{p} |\beta_i| + \frac{1}{2}(1-\alpha) \sum_{i=1}^{p} \beta_i^2 \right)$$

with $0 \leq \alpha \leq 1$, where $\alpha=1$ represents the lasso penalty, and $\alpha=0$ represents the ridge penalty.

Model Fitting

Maximum and Partial Likelihood

Under certain assumptions, a full likelihood for the hazard function can be expressed as:

$$L(\theta|\mathcal{D}) = \prod_{i=1}^{n} L_i(\theta|\mathcal{D}) = \prod_{i=1}^{n} h_i(\tilde{t}_i|\theta)^{d_i} \exp(-H_i(\tilde{t}_i|\theta))$$

where $\theta=(\beta', \alpha')$ denote the parameters of interest that the survival distribution depends on, $\mathcal{D}$ denotes the data, and H denotes the cumulative hazard function given as:

$$H_T(t) = \int_0^t h_T(s)ds, t \geq 0.$$

The inference of the regression coefficients $\beta$ in the semiparametric Cox proportional hazards model can also be carried out in terms of the partial likelihood without the need to specify a baseline hazard function. The partial likelihood function can be expressed as $$pL(\beta|\mathcal{D}) = \prod_{i=1}^{n} \left\{ \frac{\exp(x_i'\beta)}{\sum_{k=1}^{n} 1_{(\tilde{t}_k \geq \tilde{t}_i)} \exp(x_k'\beta)} \right\}^{d_i}$$

where the indicator function 1 in the denominator is used to describe the risk set $$R(\tilde{t}_i) = \{k: \tilde{t}_k \geq \tilde{t}_i\}$$

at the observed survival times, which consists of all individuals who are event-free and still under observation just prior each such observed survival time. The partial likelihood pL can be treated as a regular likelihood function and an inference on $\beta$ can be made accordingly, by optimizing pL. Further, the log partial likelihood log pL can be treated as an ordinary log-likelihood to derive partial maximum likelihood estimates of $\beta$ absent ties in the dataset. Where the dataset contains ties, approximations to the partial log-likelihood, such as the Breslow or Efron approximations to the partial log-likelihood, may be used for fitting models.

Bayesian Inference

As an alternative to likelihood inference, Bayesian inference can be used to fit a survival function. Bayesian inference relies on the posterior distribution of the model parameters $\theta \in \Theta$ given the observed dataset $\mathcal{D}$. Using Bayes theorem, the density of the posterior distribution $p(\theta|\mathcal{D})$ can be expressed as $$p(\theta|\mathcal{D}) = \frac{L(\theta|\mathcal{D})p(\theta)}{\int_\Theta L(\theta|\mathcal{D})p(\theta)d\theta} \propto L(\theta|\mathcal{D})p(\theta),$$

where the denominator $\int_\Theta L(\theta|\mathcal{D})p(\theta)d\theta$ represents evidence or marginal likelihood. As such, the posterior distribution can be expressed in terms of the prior density $p(\theta)$, which can be used to represent prior knowledge of the complete set of model parameters $\theta \in \Theta$ and the likelihood $L(\theta|\mathcal{D})$.

Bayesian analysis can also be carried out using partial likelihood, where the full likelihood $L(\theta|\mathcal{D})$ in is replaced by the partial likelihood $pL(\theta|\mathcal{D})$.

Incorporation of additional assumptions about the model parameters into the estimation problem allows for constrained exploration of model parameters in regularization approaches. In practice, regularized regression techniques can be used to add a penalty term to the estimation function to enforce that the solutions are determined with respect to these constraints. The resulting penalized log-likelihood $$\log L_{pen}(\beta,\lambda) = \log L(\beta|\mathcal{D}) - \text{pen}(\beta;\lambda),$$

where log $L(\beta|\mathcal{D})$ denotes the logarithm of the model specific likelihood $L(\beta|\mathcal{D})$ and pen($\beta;\lambda$) is the penalty term, can then be optimized. The penalty term may be split into two components pen($\beta;\lambda$)=pen($\beta$), where pen($\beta$) can define the form of the penalty and $\lambda \geq 0$ can be utilized as the regularization parameter to tune the impact of pen($\beta$) at the solution of the regularized optimization problem. In many cases, reasonable values for the regularization parameter $\lambda$ can be determined using cross validation.

Under certain conditions, the penalty terms correspond to log-prior terms that express specific information about the regression coefficients. Using the posterior definition under Bayes theorem with an informative prior $p(\beta|\lambda)$ for the regression coefficients given the tuning parameter $\lambda \geq 0$ and an additional prior $p(\lambda)$, the posterior for an observation model $L(\beta|\mathcal{D}|\beta)$ can be expressed as $$p(\beta,\lambda|\mathcal{D}) \propto L(\Sigma|\beta)p(\beta|\lambda)p(\lambda)$$

with $\theta=(\beta',\lambda)'$ and $p(\theta)=p(\beta|\lambda)p(\lambda)$. If the regularization parameter $\lambda$ is assumed to be known or fixed, the prior $p(\lambda)$ can be negligible and the resulting optimization problem becomes $$\hat{\beta}(\lambda) = \text{argmax}_\beta \{\log L(\mathcal{D}|\beta) + \log p(\beta|\lambda)\}$$

In many optimization approaches, the tuning parameter $\lambda$ is not fixed. Further, many approaches specify a prior $p(\lambda)$. A full Bayesian inference approach can be used where all model parameters are simultaneously estimated. In some cases, the regression parameters $\beta$ and the tuning parameter $\lambda$ can be jointly estimated. Typical choices for a prior $p(\beta|\lambda)$ for the regression coefficients include, without limitation Gaussian priors, double exponential priors, exponential power priors, Laplace priors, gamma priors, bimodal spike-and-slab priors, or combinations thereof.

Elastic-Net Penalized Cox Proportional Hazards Model Fit Using Coordinate Descent In an exemplary embodiment, an elastic-net penalized Cox proportional hazards model is fit using coordinate descent. Assuming no ties, an algorithm that is geared to finding $\beta$ which maximizes the likelihood $$L(\beta) = \prod_{i=1}^{m} \frac{e^{x_{j(i)}^T \beta}}{\sum_{j \in R_i} e^{x_j^T \beta}}$$

may be found by maximizing a scaled log partial likelihood, which can be expressed as $$\frac{2}{n}\ell(\beta) = \frac{2}{n}\left[\sum_{i=1}^{m} x_{j(i)}^T \beta - \log\left(\sum_{j \in R_i} e^{x_j^T \beta}\right)\right]$$

using as a constraint $\alpha\Sigma|\beta_i| + (1-\alpha)\Sigma\beta_i^2 \leq c$. Using the Lagrangian formulation, the problem can be reduced to $$\hat{\beta} = \text{argmax}_\beta \left[\frac{2}{n}\left(\sum_{i=1}^{m} x_{j(i)}^T \beta - \log\left(\sum_{j \in R_i} e^{x_j^T \beta}\right)\right) - \lambda P_\alpha(\beta)\right]$$

where $$\lambda P_\alpha(\beta) = \lambda\left(\alpha \sum_{i=1}^{p} |\beta_i| + \frac{1}{2}(1-\alpha)\sum_{i=1}^{p} \beta_i^2\right).$$

As described above, $\alpha$ is varied between 0 and 1, inclusive, where $\alpha=1$ represents the lasso penalty and $\alpha=0$ represents the ridge penalty.

A strategy that is similar to the standard Newton Raphson algorithm may be used to maximize $\hat{\beta}$. As an alternative, instead of solving a general least squares problem, a penalized reweighted least squares problem can be solved. The gradient and Hessian of the log-partial likelihood with respect to β and η, respectively, can be denoted by İ(β), Ï(β), l'(η), and l"(η), where X denotes the design matrix, β denotes the coefficient vector and η=Xβ. A two term Taylor series expansion of the log-partial likelihood centered at $\tilde{\beta}$ can be expressed as $$l(\beta) \approx l(\tilde{\beta}) + (\beta-\tilde{\beta})^T \dot{l}(\tilde{\beta}) + (\beta-\tilde{\beta})^T \ddot{l}(\tilde{\beta})(\beta-\tilde{\beta})/2 = l(\tilde{\beta}) + (X\beta-\tilde{\eta})^T l'(\tilde{\eta})(X\beta-\tilde{\eta})^T l''(\tilde{\eta})(X\beta-\tilde{\eta})/2$$

where $\tilde{\eta} = X\tilde{\beta} \cdot l(\beta)$ can be reduced to $$\ell(\beta) \approx \frac{1}{2}(z(\tilde{\eta}) - X\beta)^T \ell''(\tilde{\eta})(z(\tilde{\eta}) - X\beta) + C(\tilde{\eta}, \tilde{\beta})$$

where $$z(\tilde{\eta}) = \tilde{\eta} - l''(\tilde{\eta})^{-1} l'(\tilde{\eta})$$

and $C(\tilde{\eta}, \tilde{\beta})$ does not depend on β. l"($\tilde{\eta}$)l"($\tilde{\eta}$)l"($\tilde{\eta}$). can be replaced by a diagonal matrix with the diagonal entries of l"($\tilde{\eta}$)l"($\tilde{\eta}$), for example, to speed up the fitting algorithm, where the ith diagonal entry of l"($\tilde{\eta}$) is denoted by w($\tilde{\eta}$)$_i$ω($\tilde{\eta}$)$_i$. Thus, an exemplary fitting algorithm can comprise the steps of: 1) initializing β and setting $\tilde{\eta}=X\tilde{\beta}$; 2) computing l" ($\tilde{\eta}$) and $z(\tilde{\eta})$; 3) finding $\tilde{\beta}$ minimizing $$M(\beta) = \frac{1}{n}\sum_{i=1}^{n} w(\tilde{\eta})_i (z(\tilde{\eta})_i - x_i^T \beta)^2 + \lambda P_\alpha(\beta);$$

4) setting $\tilde{\beta}=\hat{\beta}$ and, $\tilde{\eta}=X\tilde{\beta}$; and 5) repeating steps 2-4 until convergence of $\hat{\beta}$.

The minimization in step 3 can be done by cyclical coordinate descent. With estimates for $\beta_l$ for all l≠k, the derivative of M(β) can be expressed as $$\frac{\partial M}{\partial \beta_k} = \frac{1}{n}\sum_{i=1}^{n} w(\tilde{\eta})_i x_{ik} (z(\tilde{\eta})_i - x_i^T \beta) + \lambda\alpha \cdot \text{sgn}(\beta_k) + \lambda(1-\alpha)\beta_k.$$

The coordinate solution can be expressed as $$\hat{\beta}_k = \frac{S\left(\frac{1}{n}\sum_{i=1}^{n} w(\tilde{\eta})_i x_{i,k}\left[z(\tilde{\eta})_i - \sum_{j\neq k} x_{ij}\beta_j\right], \lambda\alpha\right)}{\frac{1}{n}\sum_{i=1}^{p} w(\tilde{\eta})_i x_{ik}^2 + \lambda(1-\alpha)}$$

with $$S(x, \lambda) = \text{sgn}(x)(|x| - \lambda)_+$$

$$w(\tilde{\eta})_k = \ell''(\tilde{\eta})_{k,k} = \sum_{i \in C_k}\left[\frac{e^{\tilde{\eta}_k}\sum_{j \in R_i} e^{\tilde{\eta}_j} - (e^{\tilde{\eta}_k})^2}{\left(\sum_{j \in R_i} e^{\tilde{\eta}_j}\right)^2}\right]$$

$$z(\tilde{\eta})_k = \tilde{\eta}_k - \frac{\ell'(\tilde{\eta})_k}{\ell''(\tilde{\eta})_{k,k}} = \tilde{\eta}_k + \frac{1}{w(\tilde{\eta})_k}\left[\delta_k - \sum_{i \in C_k}\left(\frac{e^{\tilde{\eta}_k}}{\sum_{j \in R_i} e^{\tilde{\eta}_j}}\right)\right]$$

and $C_k$ is the set of i with $t_i < y_k$ (the times for which observation k is still at risk).

By combining a usual least squares coordinate wise solution with proportional shrinkage from the ridge regression penalty and soft thresholding from the lasso penalty, a solution for $\beta_k$ may be reached by applying $$\hat{\beta}_k = \frac{S\left(\frac{1}{n}\sum_{i=1}^{n} w(\tilde{\eta})_i x_{i,k}\left[z(\tilde{\eta})_i - \sum_{j\neq k} x_{ij}\beta_j\right], \lambda\alpha\right)}{\frac{1}{n}\sum_{i=1}^{p} w(\tilde{\eta})_i x_{ik}^2 + \lambda(1-\alpha)}$$

to the coordinates of β in a cyclic fashion until convergence minimizes M(β).

To obtain models for more than one value of λ, the solutions for a path of λ values may be computed for fixed α. Beginning with λ sufficiently large to set β=0, λ may be decreased until arriving near the unregularized solution. The first λ maybe set to $$\lambda_{max} = \max_j \frac{1}{n\alpha} \sum_{i=1}^{n} w_i(0) x_{ij} z(0)_i.$$

Solutions over a grid of m values between $\lambda_{min}$ and $\lambda_{max}$ may be computed by setting $\lambda_{min} = \in \lambda_{max}$, where $\lambda_j = \lambda_{max}(\lambda_{min}/\lambda_{max})^{j/m}$ for j=0, . . . , m. A suitable value for m may be selected as appropriate in a given implementation, for example m=100. A suitable value of E may also appropriately be selected in a given implementation; for example, ∈=0.05 for n<p or ∈=0.0001 for n≥p.

Further methods for the computation of $w_k$ and $z_k$ can be implemented as described in Simon et al. (Simon, N., Friedman, J., Hastie, T., Tibshirani, R (2011) Regularization Paths for Cox's Proportional Hazards Model via Coordinate Descent, Journal of Statistical Software; Vol. 39(5) 1-13), which is herein incorporated by reference in its entirety. Weights and ties can be handled as described in Simon et al.

Support Vector Machines

In various embodiments, margin maximization algorithms of support vector machines (SVMs) may be implemented to model survival data. Under such an approach, a hyperplane {x' β=−bt} can be constructed separating the individual(s) deceased or having reached an observed event at time t from the individuals remaining in the risk set after time t, at every event time t, where $\beta \in \mathbb{R}^d$ are the coefficients. The margin may be maximized as in support vector classification machines. Using this approach, for different event times t, the hyperplanes can just be translated, keeping their orientation (determined by β) the same, in analogy to using the same β for all events under proportional hazards assumptions.

In this approach, the first hyperplane can be set to separate $\mathcal{D}_1 := \{i_1\}$ from $\mathcal{R}^+_1 := \{i_2, i_3, i_4, i_5, i_6\}$, i.e. the subject to experience an event (such as an aging event), from the remaining individuals which are still at risk right after t=1. Similarly, the second hyperplane can be set to separate $\mathcal{D}_2 := \{i_2\}$ from $\mathcal{R}^+_2 := \{i_3, i_4, i_5, i_6\}$; the third hyperplane can be set to separate $\mathcal{D}_5 := \{i_5\}$ from $\mathcal{R}^+_5 := \{i_6\}$; etc.

Some modeling approaches may relax the condition that the hyperplanes achieve perfect separation. Similar to soft-margin SVMs, some observations may be allowed to lie on the 'wrong' side of the margin, with an associated penalty that is proportional to the distance $\xi_{ij}$ between the observation and the corresponding margin separating the individual i from a survivor j.

Survival support vector machines can take various forms, e.g. they may be ranking-based, regression-based, or can take the form of a hybrid of the ranking- and regression-based approaches. As an example, the objective function of a ranking-based linear survival support vector machine may be expressed as:

$$f(\beta) = \frac{1}{2}\beta^T\beta + \frac{\gamma}{2}\sum_{i,j \in P}\max(0, 1 - (\beta^T x_i - \beta^T x_j))^2,$$

where $\gamma > 0$ is a regularization parameter. A set of data points X can be ranked with respect to their predicted survival time according to elements of $X\beta$.

In some embodiments, Newton's method is applied to minimize the objective function. Where suitable, a truncated Newton method that uses a linear conjugate gradient method to compute the search direction may be applied. Use of survival support vector machines to model survival data is described in further detail in Pölsterl et al. (S. Pölsterl, N. Navab, A. Katouzian. 2015. Fast Training of Support Vector Machines for Survival Analysis. Machine Learning and Knowledge Discovery in Databases), which is herein incorporated by reference in its entirety.

Gradient Boosting

In some embodiments, gradient boosting is used to create predictive models. Gradient boosting may be used for the entire process of creating a predictive model. Gradient boosting may also be used for one or more parts of a process to create a predictive model. In some embodiments, the process of gradient boosting follows the algorithm described in the paper "Greedy function approximation: A gradient boosting machine" by Jerome H. Friedman (Ann. Statist., Volume 29, Number 5 (2011), 1189-1232; "Friedman). In some embodiments, the process of gradient boosting is an variation of the algorithm described by Friedman, which may include additional functionality. In some embodiments, the process of gradient boosting to create a Cox proportional hazards model follows the algorithm described in the paper "Generalized Boosted Models: A guide to the gbm package" by Greg Ridgeway published Aug. 3, 2007 ("Ridgeway"). In some embodiments, gbm models involve the maximization or minimization of various algebraic quantities, which may be calculated with the methods and algorithms described above or any other suitable method known in the art.

In some embodiments, the process of gradient boosting to create a Cox proportional hazards model is carried out via an implementation in the R programming language of the following algorithm: (1) Let T denote the number of iterations, input in R as "n.trees" and describe the number of trees used in the predictive model. (2) Let K denote the depth of each tree, input in R as "interaction.depth" and describe the interaction depth of the predictive model. (3) Let $\lambda$ denote the shrinkage or learning rate parameter, input in R as "shrinkage". (4) Let p denote the subsampling rate, input in R as "bag.fraction" and understood to be set to the value of 0.5 if not explicitly specified otherwise. (5) Let $\Psi(y, f(X))$ denote the loss function defined by the following sub-algorithmic steps: Let $w_i$ denote the weight of each observation, defaulting to 1 if not otherwise specified; Let $f(X_i)$ denote the prediction made for the i-th observation or row; Let $\delta_i$ denote whether or not the i-th sample is classified as dead or not, taking on the value of 1 if so and 0 otherwise; Let $t_i$ be defined as the amount of time for which the i-th observation has survived; Let $I_{j,i}$ be defined as 1 if $t_j$ is greater than or equal to $t_i$ and 0 otherwise; Let $R_i$ be defined as the sum, from integer values of j from 1 to N where N is the number of observations, of $w_j * I_{j,i} * \exp(f(X_i))$; Let the value of the loss function be defined as the sum over all valid values of i of the expression $-2*(w_i)*(\delta_i)*(f(X_i)-\log((R_i)/(w_i)))$ (6) Let y denote a vector of N values to be predicted by the predictive model, and let $y_i$ denote the i-th value of the vector y. (7) Let X denote a set of M different predictor variables and let $X_i$ denote the i-th row or observation made over those M predictor variables. (8) Let f(X) denote a predictive function which takes as input a data matrix with M columns (a representation of the M predictor variables in X) and returns a vector of predicted values, wherein the i-th value of the output was predicted from the i-th row of the input data matrix.

This algorithm will describe a method for initializing and incrementally changing the function f(X) until a termination condition has been attained. Let fhat(X) be defined similarly as f(X) to represent a provisional estimate of the final model. (8) Initialize the function fhat(X) to be equal to the value of p which minimizes the sum of $\Psi(y_i, p)$ for integer values of i from 1 to N inclusive. (9) For integer values of t, beginning at 1 and terminating at T inclusively, perform the following algorithmic steps (10) through (14). (10) For each value of i from 1 to N inclusive, let $z_i$ be defined as the negative partial derivative of $\Omega(y_i, f(X_i))$ with respect to the variable $f(X_i)$ evaluated at $f(X_i)=$fhat$(X_i)$. (11) Compute R=floor (p*N), i.e. the integer closest to but not exceeding the value of p multiplied by N, and randomly select R rows from the data matrix X such that each row has an equal probability of being selected. Let RSET denote the indices corresponding to the selected rows. (12) Fit a standard regression tree model with K terminal nodes (i.e., a depth of K) to predict the values of z corresponding to the indices contained in RSET from the corresponding observations or rows in the matrix of data X, and let this be denoted g(X). (13) For each integer from 1 to K inclusive, define $\rho_k$ as equal to the value of $\rho$ which minimizes the sum of $\Psi(y_i, f(X_i)+\varphi$ taken over all values of i such that $X_i$ is in the set $S_k$, the set of observations or rows which define terminal node k. (14) Redefine the function fhat(X) as being equal to fhat(X) plus $\lambda * \rho_k(x)$, where k(X) denotes the index of the terminal node into which an observation with features X would fall. (15) Return the function fhat as the predictive model, which terminates the overall algorithm.

In some embodiments, a gbm predictive model is fully specified by providing (1) an initial numerical value, called "initF" and algebraically denoted which is equal to 0 if gbm is used for the purpose of creating a Cox survival model, and should furthermore be assumed to be 0 if not explicitly specified otherwise, and (2) a table of numerical values or null values with columns "tree", "node", "SplitVar", "SplitCodePred", "LeftNode", and "RightNode", algebraically denoted by T, wherein given a set of input variables $\lambda$ the prediction made by the gbm predictive model is calculated with the following algorithm: (1) Let y denote the predictions made, and initialize y as a vector with length equal to the number of samples represented in X, with every value equal to "initF" (i.e., the variable I). (2) For every unique value in the column "tree" of T, denoting the particular value of "tree" as t, and for every sample $X_i$ in the data, wherein $X_i$ represents the i-th row or sample in X, perform the following algorithmic steps to obtain a vector of numbers $V_i$ corresponding to each row or sample in X: (2a) Let the variable n be equal to 0. (2b) Denote by V the variable name indicated in the column "SplitVar" of T on the row with "tree"=t and "node"=n. (2c) If V is a null value, such as "NA" or "N/A" or the empty string, return the value of "SplitCodePred" in the row with "tree"=t and "node"=n. (2d) If V is not a null value, such as "NA" or "N/A" or the empty string, then let L denote the value of "LeftNode" and let R denote the value of "RightNode", and let S denote the value of "SplitCodePred", all referring to the row in T where "tree"=t and "node"=n. If the value of the variable V in $X_i$ is less than or equal to S, then update the value of n to L, and if not, update the value of n to R. Subsequently, repeat the sub-algorithmic steps (2b) through (2d) until a numeric value is returned by the sub-algorithm. (3) For each value in y, update $y_i$ to be equal to $y_i$ plus the sum of all values in $V_i$. Return y as the vector of predictions made by the gbm predictive model. This terminates the overall algorithm. The creation of a gradient boosting predictive model, as described by any one or multiple of the algorithms and references outlined herein, may be performed with statistical or mathematical software, such as Python, R, Mathematica, NumPy, SciPy, Julia, Fortran, and/or other suitable methods known to those skilled in the art.

Survival predictor models built using any of the described methods or other suitable methods known in the art may have covariates comprising a representation of one or more survival biomarkers and/or one or more aging indicators.

Selection of Biomarkers

In some embodiments, significance associated with one or more methylation markers and/or clinical factors is measured by its estimated impact on the value of a subject's survival metric, relative chance of survival, or chance of having and aging event (e.g. death or acquiring an aging-related disease) within an equivalent time period as compared to a default state ("relative survival risk"). The default state may relate to a subject having a normalized methylation marker value at a unit amount lower. In cases tracking a methylation marker's presence or absence only, a unit amount may mean the difference between having a methylation marker present and absent. In some embodiments, the relative survival risk is measured with respect to a comparison group having, setting, representing, or approximating the default state. For example, a survival predictor model that is configured to calculate relative survival risk may have used data from samples from a comparison group. Such a survival predictor model may determine a value for relative survival risk based on the degree of methylation at one or more CpG sites, such as survival biomarkers, and/or clinical factors. The unit amount for a normalized methylation marker value may be determined based on the distribution of a methylation marker's degree of methylation within a set of samples from subjects. A unit amount of a significant methylation marker may have an impact on the value of relative survival risk of at least or at least about 1.01, 1.05, 1.1. 1.15, 1.2, 1.3, 1.4, 1.5, 1.6, 1.7, 1.8, 1.9, 2.0, 2.1, 2.2, 2.3 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3 or greater. A unit amount of a significant methylation marker may have an impact on the value of relative survival risk of at most or at most about 0.99, 0.95, 0.90, 0.87, 0.85, 0.8, 0.75, 0.7, 0.65, 0.60, 0.58, 0.5, 0.53, 0.52, 0.5, 0.49, 0.48, 0.47, 0.46, 0.45, 0.44, 0.43, 0.42, 0.41, 0.4, 0.39, 0.38, 0.37, 0.36, 0.35, 0.34, 0.33, 0.32, 0.31, 0.3, 0.29, 0.28, 0.27, 0.26, 0.25, 0.24, 0.23, or less. One or more survival biomarkers may be selected from methylation markers having a threshold amount of significance.

A survival metric can be calculated by combining data representing presence and/or abundance and/or degree of methylation of multiple survival biomarkers, such as at least or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75 or more biomarkers. A survival metric can be calculated by combining data representing presence and/or abundance of multiple protein markers, such as at least or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75 or more biomarkers with data representing one or more clinical factors (e.g., age, sex, race, ethnicity, smoking status, alcohol consumption status, diastolic blood pressure, systolic blood pressure, a family history parameter, a medical history parameter, a medical symptom parameter, height, weight, a body-mass index, or resting heart rate of a subject). Survival predictor models, described in further detail elsewhere herein, may be capable of combining selected survival biomarker(s) and clinical factor(s) to determine the survival metric.

A univariate or multivariate survival predictor model may be assessed for its estimated impact on the value of a subject's survival metric, relative chance of survival, or chance of having and aging event within an equivalent time period as compared to a default state. One way to assess a predictor's performance is to calculate a hazard ratio using a Cox proportional hazards model. In the case of a continuous univariate predictor, the hazard ratio reflects the change in the risk of death if the value of the predictor rises by one unit. In the case of a continuous multivariate survival predictor model, the hazard ratio reflects the change in the risk of death if the output of the multivariate model rises by one unit. The covariate vector used in a multivariate model may represent values of one or more aging indicators and/or one or more normalized methylation marker values.

A score produced via a combination of data types can be useful in classifying, sorting, or rating a sample from which the score was generated.

Clinical Factors

In some embodiments, one or more clinical factors in a subject, can be assessed. In some embodiments, assessment of one or more clinical factors in a subject can be combined with a survival biomarker analysis in the subject to provide a survival metric for the subject.

The term "clinical factor" comprises a measure of a condition of a subject, e.g., disease activity or severity. "Clinical factor" comprises all indicators of a subject's health status, which may be obtained from a patient's health record and/or other characteristics of a subject, such as, without limitation, age and gender. A clinical factor can be a score, a value, or a set of values that can be obtained from evaluation of a sample (or population of samples) from a subject. A clinical factor can also be predicted by markers, including genetic markers, and/or other parameters such as gene expression profiles.

A clinical factor may comprise, age, sex, race, ethnicity, smoking status, alcohol consumption status, diastolic blood pressure, systolic blood pressure, a family history parameter, a medical history parameter, such as a disease diagnosis, a medical symptom parameter, height, weight, a body-mass index, or resting heart rate of a subject.

In some embodiments, one or more clinical factors are used to identify significant methylation markers. In some embodiments, one or more clinical factors are used to select survival biomarkers to be used in a survival predictor model. In some embodiments, one or more clinical factors are used as covariates in a survival predictor model. In some embodiments, one or more clinical factors are used to include or exclude subjects from a study cohort, such as a study cohort for model testing or model cross-validation. In each case, the methods and compositions described herein may use at least or at least about 1, 2, 3, 4, 5, 6, 7, 8, 9, 10, 11, 12, 13, 14, 15, 16, 17, 18, 19, 20, or more clinical factors.

Computer Implementation

The methods and compositions described herein, including the methods of generating a prediction model and the methods of for determining a survival metric for a subject, may comprise a computer or use thereof.

In one embodiment, a computer comprises at least one processor coupled to a chipset. Also coupled to the chipset may be one or more of a memory, a storage device, a keyboard, a graphics adapter, a pointing device, and a network adapter. A display may be coupled to the graphics adapter. In one embodiment, the functionality of the chipset is provided by a memory controller hub and an I/O controller hub. In another embodiment, the memory is coupled directly to the processor instead of the chipset.

The storage device may be any device capable of holding data, like a hard drive, compact disk read-only memory (CD-ROM), DVD, or a solid-state memory device. The memory may be configured to hold instructions and data used by the processor. The pointing device may be a mouse, track ball, or other type of pointing device, and is used in combination with the keyboard to input data into the computer system. The graphics adapter may be configured to display images and other information on the display. The network adapter may be configured to couple the computer system to a local or wide area network.

As is known in the art, a suitable computer can have different and/or other components than those described previously. In addition, the computer can lack certain components. A storage device can be local and/or remote from the computer (such as embodied within a storage area network (SAN)).

In various embodiments, the computer is adapted to execute computer program modules for providing functionality described herein. A computer module may comprise a computer program logic and/or computer program parameters utilized to provide the specified functionality. A module can be implemented in hardware, firmware, and/or software. Program modules may be stored on the storage device, loaded into the memory, and/or executed by the processor.

The methods and compositions described herein may comprise other and/or different modules than the ones described here. The functionality attributed to any module or modules may be performed by one or more other or different modules in other embodiments. This description may occasionally omit the term "module" for purposes of clarity and convenience.

Methods of Therapy

In various embodiments, the methods and compositions described herein comprise treatment of subjects, such as a treatment of an aging related disease. A treatment may be applied following a diagnostic step performed according to the various embodiments described throughout, including those comprising determination of a survival metric.

In various embodiments, the methods and compositions described herein comprise a therapeutically effective amount of a drug, such as a drug that is identified through a drug screen as described in further detail elsewhere herein and/or administration or distribution thereof. These drugs may be formulated in pharmaceutical compositions. These compositions may comprise, in addition to one or more of the drugs identified through a drug screen, a pharmaceutically acceptable excipient, carrier, buffer, stabilizer or other materials well known to those skilled in the art. Such materials may be selected so that they are non-toxic and do not interfere with the efficacy of an active ingredient, such as a drug that is identified through a drug screen as described in further detail elsewhere herein. The precise nature of the carrier or other material may depend on the route of administration, e.g. oral, intravenous, cutaneous or subcutaneous, nasal, intramuscular, intraperitoneal routes.

Pharmaceutical compositions for oral administration may be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required.

Whether it is a polypeptide, antibody, nucleic acid, small molecule or other pharmaceutically useful compound that is to be given to an individual, administration dose may be set to be in a "therapeutically effective amount," such as in a "prophylactically effective amount," the amount being sufficient to show benefit to the individual. The amount which will be therapeutically effective in the treatment of a particular individual's disorder or condition may depend on the symptoms and severity thereof. The appropriate dosage, e.g. a safe dosage or a therapeutically effective dosage, may be determined by any suitable clinical technique known in the art, e.g., without limitation in vitro and/or in vivo assays.

A composition can be administered alone or in combination with other treatments, either simultaneously or sequentially dependent upon the condition to be treated.

Suitable survival related therapies for a subject may comprise advising lifestyle changes, cessation of smoking, avoiding secondhand smoke, eating a healthy diet, regular exercise, achieving and/or maintaining a healthy weight, keeping a healthy mental attitude; weight management; reducing blood pressure; reducing cholesterol; managing diabetes; administration of therapeutics such as drugs, undertaking of one or more procedures; performing further diagnostics on the subject; assessing the subject's health further; or optimizing medical therapy.

Actuarial Methods

In various embodiments, the methods and systems described herein comprise assessment of absolute or relative risk of mortality or likelihood of survival within a specified time period. A survival metric that is generated according to the methods described herein may be used to assess risk of mortality or likelihood of survival for one or more subjects. For example, a relative or absolute risk of having at least 1, 2, 3, 4, 5, or more subjects die out of a group of subjects may be calculated based on the survival metric for one or more of such subjects. A life or health insurance packages may be offered or priced based on a relative or absolute risk of mortality or likelihood of survival. In each case, a risk of mortality or likelihood of survival may be assessed, for the following 1, 2, 3, 4, 5, 6, 9, 12, 18, 24, 30, 36, 48, 60, or more months.

Screens

In various embodiments, the methods and compositions described herein are used to identify one or more survival factors, such as outside factors, that have a positive or negative effect on a survival metric, time to aging event, chance of survival, life expectancy, chance of death, and/or another survival related outcome. In some embodiments, survival predictor model outputs are used to identify a survival factor. A test target, such as, without limitation, a subject, an organ, a tissue, a cell, or a portion thereof may be contacted by or interacted with one or more candidate factors. The test target may be derived from an animal, such as a mammal, e.g. a rat, a mouse, a monkey, a rabbit, a pig, or a human. One or more samples may be collected from the test target. A Methylation marker profile may be obtained from the test target or one or more samples. A survival predictor model may be used to obtain a survival metric based on the methylation marker profile. Survival metrics of various candidate factors may be compared to identify candidate factors that have a high likelihood of having a significant relationship to survival related outcomes. In some embodiments, candidate factors comprise a library of test drugs. For example, if drug-tested test targets show significantly altered prediction for survival, the tested drug may be selected for use in aging relating applications, including therapeutic applications. Accordingly, a drug screen may be implemented screening test drugs for survival related outcomes.

Kits

Also disclosed herein are kits for obtaining a survival metric. Such kits may comprise one or more of a sample collection container, one or more reagents for detecting the presence and/or abundance and/or degree of methylation of one or more survival biomarkers, instructions for calculating a survival metric based on the expression levels, and credentials to access a computer software. The computer software may be configured to intake survival biomarker data, determine a survival biometric, and/or store survival biomarker data and/or survival biometric.

In some embodiments, a kit comprises software for performing instructions included with the kit. The software and instructions may be provided together. For example, a kit can include software for generating a survival metric by mathematically combining data generated using the set of reagents.

A kit can include instructions for classifying a sample according to a score. A kit can include instructions for rating a survival related outcome, such as life expectancy, chance of survival, or risk of death using a survival metric. Rating may comprise a determination of an increase or decrease in a survival related outcome.

A kit may comprise instructions for obtaining data representing at least one survival biomarker and/or at least one clinical factor associated with a subject as described in further detail elsewhere herein. In certain embodiments, a kit can include instructions for mathematically combining the data representing at least one clinical factor with data representing the presence and/or abundance and/or degree of methylation of one or more survival biomarkers to generate a score.

A kit may include instructions for taking at least one action based on a score for a subject, e.g., treating the subject, advising lifestyle changes to the subject, performing a procedure on the subject, performing further diagnostics on the subject, assessing the subject's health further, or optimizing medical therapy.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of methylomics, protein chemistry, biochemistry, recombinant DNA techniques and pharmacology, within the skill of the art. Such techniques are explained fully in the literature. See, e.g., M. Fraga and A. F. Fernandez, *Epigenomics in Health and Disease* (Academic Press, 2015); T. O. Tollefsbol, *Epigenetic Protocols* (Springer Protocols, 2011); A. Meissner and J. Waller, *Epigenetic Mechanisms in Cellular Reprogramming* (Springer, 2015); K. Ayyanathan, *Specific Gene Expression and Epigenetics* (Apple Academic Press, 2014); N. Carey and D. Fox, *Epigenetics for Drug Discovery* (Royal Society of Chemistry, 2015); W. Sippl and M. Jung, *Epigenetic Targets in Drug Discovery* (Wiley-VCH, 2009); A. L. Lehninger, *Biochemistry* (Worth Publishers, Inc., current edition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990); Carey and Sundberg *Advanced Organic Chemistry* $3^{rd}$ Ed. (Plenum Press) Vols A and B(1992).

Example 1: Study Cohort

In order to study methylation sites (CpG sites) that are associated with aging, a study cohort was designed. Study subjects were drawn from the Offspring cohort of the Framingham Heart Study (Thomas R. Dawber, Gilcin F. Meadors, and Felix E. Moore, Jr. Cohort Profile: Framingham Heart Study, of the National Heart, Lung, and Blood Institute and Boston University. Am J Public Health Nations Health. first published March 1951 as "Epidemiological Approaches to Heart Disease: The Framingham Study" at www.ncbi.nlm.nih.gov/pmc/articles/PMC1525365/). Members of the Offspring cohort of the Framingham Heart Study began to be enrolled in 1971 and in-person evaluations occurred approximately every 4 to 8 years afterward. The members of the study used for the following analyses were determined as follows. Initially, subjects used for the study were all members of the Offspring cohort of the Framingham Heart Study who survived until the eighth examination cycle, occurring from 2005 to 2008, and consented to participation in genetic research. These criteria yield 2,566 study members for which methylation readings were taken, a process which is described in Examples 2 through 3. Study members were further restricted to those for which the methylation readings passed quality control, as described in Example 5, yielding 2,563 study members. Study members were further restricted to those for which at least one follow-up date later than the date of Examination 8 (at which the blood was drawn) was recorded, yielding 2,559 study members. These 2,559 study members comprise the final study cohort, i.e., the sample of people upon which analysis was performed, as described below. For the 2,559 subjects in the study cohort, 339 deaths were recorded as of June 2017. These 2,559 subjects have ages with a mean of 66.34 years and a standard deviation of 8.95 years.

Example 2: Sample Collection

Peripheral blood samples from the 2,566 Framingham Offspring cohort members who survived until the eighth examination cycle, occurring from 2005 to 2008, and consented to participation in genetic research were collected as previously mentioned, with collection occurring during the eighth examination cycle (2005 to 2008).

Example 3: Methylomics Protocols

Genomic material (DNA) was extracted from the buffy coat present in the peripheral blood samples with the Qiagen Gentra Puregene DNA extraction kit. Extracted genomic material was bisulfite converted with the Zymo Research Corporation EZ DNA Methylation kit. Bisulfite converted genomic material (DNA) was hybridized to the 12 sample Illumina HumanMethylation450BeadChips via the Illumina Infinium HD Methylation protocol and Tecan robotics. The Illumina 450k methylation array was used for methylomic sequencing of the prepared genomic material.

Example 4: Methylation Sequencing Data Processing

Raw sequencing data files of high resolution sequencing data acquired at over 485,000 methylation sites (e.g., 485,512 in one example) per sample at single-nucleotide resolution were used for methylation site detection, identification, and quantification of methylation fraction. In each raw data file, R is used to extract the raw red and green channels. Further data processing is described as in Examples 5, 6, and 7.

Example 5: Quality Control for Methylation Data

Methylation data were received from the biological samples analyzed using the Illumina HumanMethylation450BeadChips along with the Infinium HD Methylation protocol and Tecan robotics with the Illumina Infinium Methylation Assay. The methylation data was associated with the dbGaP study at www.ncbi.nlm.nih.gov/projects/gap/cgi-bin/study.cgi?study_id=phs000724.v6.p10. Quality control was performed by using the "plotQC" function in the R package "minfi", version 1.22.1 with the "badSampleCutoff" parameter set to the default value of 10.5, and removing the samples identified by this function as failing quality control. Quality control was performed with R version 3.4.1. In total three samples were removed from the analysis.

Example 6: Data Cleaning

Background correction and control normalization relative to a specified reference array were performed with the "processIllumina" function found in version 1.22.1 of the R package "minfi" (bioconductor.org/packages/release/bioc/html/minfi.html) installed on R version 3.4.1. A rank inverse normal transformation was applied to normalize the data.

At a false discovery rate of 5% and without controlling for the values of clinical factors, 203770 methylation markers were found to associate significantly with all-cause mortality.

At a false discovery rate of 5% and after controlling for the values of clinical factors comprising age, sex, systolic blood pressure, diastolic blood pressure, whether an individual has high cholesterol or not, whether an individual has cardiovascular disease or not, whether an individual has high blood sugar or not, smoking status, smoking rate, time period spent smoking, number of days per week that a person drinks alcohol, the number of drinks per day, the number of hours per day that a person engages in mild physical activity, moderate physical activity, and in heavy physical activity, 24791 methylation markers associate significantly with all-cause mortality.

Predictor models using one or more biomarkers, including but not limited to methylation sites (CpG sites) and metabolites, can be built using a variety of modeling approaches. The following few examples illustrate a few of those approaches.

Example 7: Building Predictor Models Using Machine Learning Methods—L1 Penalized CoxPH Regression with Methylation Markers as Predictors Machine learning methods can be applied to the methylation markers to build predictor models for survival. A multi-methylation marker survival predictor model of all-cause mortality was built using L1 penalized (LASSO) regression. A CoxPH objective function was used and L1 penalized regression via coordinate descent, as described above, was applied as provided in glmnet package for R ("Package 'glmnet'," CRAN, Maintainer: Trevor Hastie, Mar. 17, 2016, 23 pages, may be retrieved at cran.r-project.org/web/packages/glmnet/glmnet.pdf). The regularization parameter lambda was selected with 5-fold cross-validation.

To estimate the generalization performance of the survival predictor model, the hazard ratio (HR) and concordance was calculated using nested 5-fold cross-validation. For each repeat, the data were split into training and testing sets (at 80%/20%), Then, within the training set, another 5-fold CV was used to select the regularization coefficient, using regularized CoxPH regression with objective function $$\lambda \|\beta\|^2 + \Sigma_{i:C_i=1} \log \theta_i - \log(\Sigma_{j:Y_j \ge Y_i} \theta_j)$$

as discussed above. The chosen coefficient was then used to fit weights on the entire training set (80% of the full data), and these weights were evaluated on the test set to determine hazard ratio and concordance.

When methylation markers were thusly selected (i.e., used to train a predictor model for survival) from the set of 485512 methylation markers after the performance of data cleaning methods described in Example 6 (without controlling for clinical factors), we obtained a survival predictor model with 153 methylation markers (HR=2.8372; concordance=0.7789; Table 1).

TABLE 1

(Covariate: methylation marker (CpG site); Coefficient: the coefficient optimal for the corresponding CpG site for the optimal L1 regularized CoxPH survival predictor model, where "optimal" indicates that the value of the hyperparameter "lambda" were selected so as to minimize the 5-fold cross-validated error of the corresponding L1 regularized CoxPH survival predictor model (a process which yielded lambda = 0.022097).)

| Covariate | Coefficient |
| --- | --- |
| cg00328972 | −0.00893 |
| cg04885881 | −0.00943 |
| cg16138181 | −0.00377 |
| cg27400644 | 0.006122 |

TABLE 1-continued (Covariate: methylation marker (CpG site); Coefficient: the coefficient optimal for the corresponding CpG site for the optimal L1 regularized CoxPH survival predictor model, where "optimal" indicates that the value of the hyperparameter "lambda" were selected so as to minimize the 5-fold cross-validated error of the corresponding L1 regularized CoxPH survival predictor model (a process which yielded lambda = 0.022097).)

| Covariate | Coefficient |
| --- | --- |
| cg17339202 | −0.01814 |
| cg06964608 | 0.012657 |
| cg14914422 | 0.004511 |
| cg25745713 | 0.011529 |
| cg13871826 | −0.02077 |
| cg23036668 | −0.00662 |
| cg09368875 | −0.01722 |
| cg26182859 | 0.014572 |
| cg03610604 | 0.011885 |
| cg26677288 | −0.01615 |
| cg05360477 | −0.03817 |
| cg19614911 | 0.002595 |
| cg26691604 | 0.014271 |
| cg06383022 | 0.019925 |
| cg00209520 | −0.00541 |
| cg24705426 | −0.00821 |
| cg17980786 | 0.010496 |
| cg11142705 | 0.006922 |
| cg19281794 | 0.045255 |
| cg07553761 | 0.028599 |
| cg15466157 | 0.008627 |
| cg11078084 | 0.012265 |
| cg11640079 | 0.00706 |
| cg01945641 | 0.040146 |
| cg17903782 | 0.020582 |
| cg07890104 | 0.004239 |
| cg26647566 | −0.00868 |
| cg02188818 | −0.00632 |
| cg15586439 | 0.042116 |
| cg04813875 | 0.032051 |
| cg05575921 | −0.04982 |
| cg08238319 | 0.036921 |
| cg00409356 | 0.022335 |
| cg22978003 | 0.020371 |
| cg20757748 | 0.01979 |
| cg19419291 | −0.07024 |
| cg07465864 | −0.01195 |
| cg24708145 | 0.000714 |
| cg23500537 | 0.003958 |
| cg01201215 | −0.02458 |
| cg17339488 | 0.004662 |
| cg01425680 | 0.0173 |
| cg16006841 | −0.02265 |
| cg01808130 | −0.02115 |
| cg21572722 | 0.085759 |
| cg04861640 | −0.02433 |
| cg15342087 | −0.00847 |
| cg09842479 | −0.01238 |
| cg21570988 | 0.031551 |
| cg26987613 | −0.01571 |
| cg03546163 | −0.09228 |
| cg25114611 | −0.11316 |
| cg22985172 | 0.016746 |
| cg00587301 | 0.023978 |
| cg24160243 | 0.023305 |
| cg12400790 | 0.034345 |
| cg03366574 | 0.106384 |
| cg00277397 | −0.0926 |
| cg00048759 | 0.053013 |
| cg22374237 | 0.022592 |
| cg15310871 | 0.007803 |
| cg08288130 | −0.01191 |
| cg14195992 | −0.04245 |
| cg18029167 | −0.01462 |
| cg17131553 | −0.02335 |
| cg25473866 | 0.041579 |
| cg17052170 | −0.00215 |
| cg01863081 | 0.060272 |
| cg20784950 | −0.05945 |
| cg18000391 | 0.006065 |
| cg14605590 | −0.04897 |
| cg14396892 | 0.001004 |
| cg08414635 | −0.01143 |
| cg00008629 | −0.02538 |
| cg13676763 | −0.02509 |
| cg14541800 | −0.02269 |
| cg03672997 | −0.0065 |
| cg23648810 | 0.021056 |
| cg18454045 | 0.002593 |
| cg04406111 | 0.006309 |
| cg06777902 | −0.02861 |
| cg00321709 | 0.043541 |
| cg09554951 | 0.021583 |
| cg23190089 | −0.0256 |
| cg13632983 | 0.000402 |
| cg12535090 | 0.023462 |
| cg13245152 | 0.002988 |
| cg02791145 | −0.01644 |
| cg18825531 | −0.02274 |
| cg13273340 | 0.03888 |
| cg23796243 | 0.009393 |
| cg17058475 | −0.04572 |
| cg16589644 | 0.006323 |
| cg12491115 | 0.014014 |
| cg01039401 | 0.021191 |
| cg24626079 | −0.00964 |
| cg07178945 | 0.003424 |
| cg02519286 | −0.08686 |
| cg14632906 | −0.01348 |
| cg05921581 | −0.03382 |
| cg18473521 | 0.056912 |
| cg02021442 | −0.01277 |
| cg12286415 | 0.019544 |
| cg01906637 | 0.010283 |
| cg20000562 | 0.037086 |
| cg26992600 | 0.0177 |
| cg16763443 | 0.025383 |
| cg11190278 | 0.020489 |
| cg23998119 | 0.002764 |
| cg25132241 | 0.007135 |
| cg09970175 | 0.002418 |
| cg02812767 | −0.09029 |
| cg12101586 | −0.05748 |
| cg00077297 | −0.00595 |
| cg23633568 | −0.00512 |
| cg08428878 | 0.000184 |
| cg05028929 | −0.00772 |
| cg00459119 | 0.005461 |
| cg02481950 | 0.001057 |
| cg01355753 | −0.01817 |
| cg16376828 | −0.01754 |
| cg08770961 | 0.017035 |
| cg08726900 | 0.0027 |
| cg22283643 | 0.000943 |
| cg19265972 | −0.04546 |
| cg19789473 | −0.03248 |
| cg02486253 | 0.046565 |
| cg18596621 | 0.00925 |
| cg15756507 | 0.008104 |
| cg17807001 | 0.007953 |
| cg24084891 | 0.008694 |
| cg06706875 | 0.018073 |
| cg07573872 | −0.01176 |
| cg00804433 | 0.006947 |
| cg14074174 | −0.00371 |
| cg22693863 | −0.01368 |
| cg11249283 | −0.08453 |
| cg09935271 | −0.01885 |
| cg03707168 | −0.00247 |
| cg07134608 | −0.00047 |
| cg05205351 | −0.01508 |
| cg07414492 | −0.0044 |

TABLE 1-continued (Covariate: methylation marker (CpG site); Coefficient: the coefficient optimal for the corresponding CpG site for the optimal L1 regularized CoxPH survival predictor model, where "optimal" indicates that the value of the hyperparameter "lambda" were selected so as to minimize the 5-fold cross-validated error of the corresponding L1 regularized CoxPH survival predictor model (a process which yielded lambda = 0.022097).)

| Covariate | Coefficient |
|---|---|
| cg00871610 | −0.0733 |
| cg13840526 | 0.024644 |
| cg05072413 | −0.06308 |
| cg13909895 | −0.0526 |
| cg06128881 | −0.01501 |
| cg00141845 | −0.00611 |
| cg27590787 | −0.00107 |

Example 8: Building Predictor Models Using Machine Learning Methods—L1 Penalized CoxPH Regression with Methylation Markers and Clinical Factors as Predictors As in Example 7, a multi-methylation marker predictor model for all-cause mortality was built with L1 penalized regression using a CoxPH objective function. Certain clinical factors, namely age, sex, systolic blood pressure, diastolic blood pressure, whether an individual has high cholesterol or not, whether an individual has cardiovascular disease or not, whether an individual has high blood sugar or not, whether an individual is a smoker or not, the number of cigarettes smoked per day, the number of years an individual has smoked, the number of days per week an individual drinks alcohol, the number of drinks of alcohol per day, the number of hours per day for which an individual engages in mild physical activity, the number of hours per day for which an individual engages in moderate physical activity, and the number of hours per day for which an individual engages in heavy physical activity, were also included in the L1 LASSO regression to build a multi-methylation marker predictor model. The variable corresponding to age was not subjected to regularization when fitting the parameters of the model as described above. When values of the clinical factors were unavailable, they were imputed with their means. These clinical factors can be found in the files "phs000007.v29.pht003099.v4.p10.c1.vr_dates_2014_a_0912s.HMB-IRB-MDS.txt.gz" (for age and sex) and "phs000007.v29.pht000747.v5.p10.c1.ex1_8s.HMB-IRB-MDS.txt.gz" for the others at the dbGaP archive at www.ncbi.nlm.nih.gov/projects/gap/cgi-bin/study.cgi?study_id=phs000007.v29.p10/.

To estimate the generalization performance of the survival predictor model, the hazard ratio and concordance of the survival predictor model was calculated using nested 5-fold cross-validation as in Example 7.

The regression for the survival predictor model resulted in 132 methylation markers and 3 clinical factors with non-zero coefficients out of the set of methylation markers reduced from the original 485512 markers using the data cleaning methods in Example 6 (without controlling for clinical factors) and the set of 15 clinical factors (HR=3.1469; concordance=0.7872; Table 2).

This multi-methylation marker and multi-clinical factor survival predictor model shows greater generalization performance compared to the 153-methylation marker survival predictor model in Example 7 (HR=2.8372; concordance=0.7789; Table 1), which excluded clinical factors as covariates.

TABLE 2

(Covariate (clinical factor or methylation marker (CpG site); Coefficient: the coefficient optimal for the corresponding CpG site or clinical factor in the optimal L1 regularized CoxPH survival predictor model, where "optimal" indicates that the value of the hyperparameter "lambda" were selected so as to minimize the 5-fold cross-validated error of the corresponding L1 regularized CoxPH survival predictor model (a process which yielded lambda = 0.022097)).

| Covariate | Coefficient |
|---|---|
| age | 0.808722 |
| cardiovascular_disease | 0.121482 |
| years_smoking | 0.037132 |
| cg07965774 | 0.009072 |
| cg23814214 | −0.00216 |
| cg16138181 | −0.00419 |
| cg12717729 | −0.02883 |
| cg16401270 | −0.01755 |
| cg11193462 | 0.039239 |
| cg13871826 | −0.0143 |
| cg19361456 | 0.022571 |
| cg03610604 | 0.005337 |
| cg10573505 | 0.000868 |
| cg26677288 | −0.0213 |
| cg05360477 | −0.0343 |
| cg07548255 | 0.016727 |
| cg05971072 | −0.00306 |
| cg23023604 | 0.002989 |
| cg19281794 | 0.056892 |
| cg10773224 | −0.00602 |
| cg09573795 | 0.006832 |
| cg11078084 | 0.014936 |
| cg15586439 | 0.000735 |
| cg04813875 | 0.023573 |
| cg05575921 | −0.15021 |
| cg08238319 | 0.040898 |
| cg00409356 | 0.009505 |
| cg22978003 | 0.007986 |
| cg19419291 | −0.02367 |
| cg11937703 | 0.003771 |
| cg11339912 | −0.01386 |
| cg25090510 | −0.0447 |
| cg01425680 | 0.005387 |
| cg16006841 | −0.01344 |
| cg09842479 | −0.00858 |
| cg26987613 | −0.03359 |
| cg03546163 | −0.06871 |
| cg25114611 | −0.06227 |
| cg15478981 | 0.003699 |
| cg24900370 | −0.02759 |
| cg22985172 | 0.037826 |
| cg11454936 | 0.008267 |
| cg12400790 | 0.015813 |
| cg03366574 | 0.051667 |
| cg25975690 | −0.00811 |
| cg00137629 | 0.006549 |
| cg10691866 | −0.00755 |
| cg13234848 | −0.00391 |
| cg07602571 | 0.002236 |
| cg17583077 | 0.00345 |
| cg24285543 | 0.021921 |
| cg18107989 | 0.000608 |
| cg15310871 | 0.010624 |
| cg14195992 | −0.00212 |
| cg18029167 | −0.01903 |
| cg08792272 | 0.01791 |
| cg25473866 | 0.030616 |
| cg01863081 | 0.03793 |
| cg20784950 | −0.03764 |
| cg18000391 | 0.005756 |
| cg07980830 | −0.01439 |
| cg13982318 | −0.03762 |
| cg14396892 | 0.020238 |
| cg00008629 | −0.02459 |
| cg14138047 | 0.000609 |

TABLE 2-continued (Covariate (clinical factor or methylation marker (CpG site); Coefficient: the coefficient optimal for the corresponding CpG site or clinical factor in the optimal L1 regularized CoxPH survival predictor model, where "optimal" indicates that the value of the hyperparameter "lambda" were selected so as to minimize the 5-fold cross-validated error of the corresponding L1 regularized CoxPH survival predictor model (a process which yielded lambda = 0.022097)).

| Covariate | Coefficient |
|---|---|
| cg14541800 | −0.03232 |
| cg03672997 | −0.01569 |
| cg23648810 | 0.005904 |
| cg04406111 | 0.012743 |
| cg02124758 | −0.00632 |
| cg00321709 | 0.016134 |
| cg24577116 | 0.004622 |
| cg13632983 | 0.025828 |
| cg04733365 | −0.00566 |
| cg12535090 | 0.000754 |
| cg03447554 | −1.20E−05 |
| cg02791145 | −0.03315 |
| cg14161454 | 0.006645 |
| cg13273340 | 0.001085 |
| cg02100918 | 0.020947 |
| cg17058475 | −0.00245 |
| cg12491115 | 3.63E−05 |
| cg01039401 | 0.002943 |
| cg07178945 | 0.025626 |
| cg02519286 | −0.01928 |
| cg17817168 | 0.000448 |
| cg05921581 | −0.0004 |
| cg02384661 | −0.01277 |
| cg02021442 | −0.03415 |
| cg00308065 | 0.012028 |
| cg00748494 | −0.00125 |
| cg01906637 | 0.035198 |
| cg16763443 | 0.001973 |
| cg11190278 | 0.01665 |
| cg09954698 | 0.004931 |
| cg25132241 | 0.005179 |
| cg26102435 | 0.028249 |
| cg07197326 | 0.006508 |
| cg23811289 | 0.005125 |
| cg09970175 | 0.004967 |
| cg02812767 | −0.07323 |
| cg12101586 | −0.03435 |
| cg23633568 | −0.00332 |
| cg08428878 | 0.002501 |
| cg02481950 | 0.008377 |
| cg01355753 | −0.03331 |
| cg02531193 | 0.008276 |
| cg16376828 | −0.01784 |
| cg10241823 | 0.016286 |
| cg22748407 | −0.00558 |
| cg19789473 | −0.01911 |
| cg02486253 | 0.002025 |
| cg15756507 | 0.047154 |
| cg24181662 | −0.01238 |
| cg17807001 | 0.005752 |
| cg19590707 | −0.00337 |
| cg13765206 | −0.02277 |
| cg17318716 | 0.005239 |
| cg07573872 | −0.05191 |
| cg00804433 | 0.007634 |
| cg04234014 | 0.000291 |
| cg16526705 | 0.004168 |
| cg11249283 | −0.04559 |
| cg19477346 | −0.01079 |
| cg03707168 | −0.02684 |
| cg08559712 | 0.011009 |
| cg00871610 | −0.05456 |
| cg14162806 | −0.0082 |
| cg05072413 | −0.03602 |
| cg13909895 | −0.00518 |
| cg16088894 | 0.012475 |
| cg06128881 | −0.01247 |
| cg00141845 | −0.00595 |
| cg27590787 | −0.00484 |
| cg11898347 | −0.01892 |

Example 9: Building Predictor Models Using Machine Learning Methods—Elastic Net Regularized CoxPH Regression with a Small Subset of Methylation Markers in Combination with Clinical Factors A set of 26987 methylation markers was generated by selecting from the 485512 available methylation markers those covered by the HumanMethylation27K BeadChip (HM27), Illumina. A multi-methylation marker survival predictor models was built using these methylation markers and the clinical factors from Example 8 as covariates.

A multi-methylation marker survival predictor model of all-cause mortality including clinical factors as covariates was built using elastic net regularized regression. A CoxPH objective function was used and elastic net penalized regression via coordinate descent, as described above, was applied as provided in glmnet package for R ("Package 'glmnet'," CRAN, Maintainer: Trevor Hastie, Mar. 17, 2016, 23 pages, may be retrieved at cran.r-project.org/web/packages/glmnet/glmnet.pdf). The regularization parameters lambda and alpha were selected with 5-fold cross-validation.

To estimate the generalization performance of the survival predictor model, the hazard ratio and concordance of the survival predictor model was calculated using nested 5-fold cross-validation as in Example 7.

The regression for the survival predictor model resulted in 21 methylation markers and 3 clinical factors with non-zero coefficients, out of a subset of methylation markers reduced from the subset of 26987 methylation markers using the data cleaning methods described in Example 6 and the set of 15 clinical factors (HR=2.9968; concordance=0.7769; Table 3).

TABLE 3

(Covariate (clinical factor or methylation marker (CpG site); Coefficient: the coefficient optimal for the corresponding CpG site or clinical factor in the optimal elastic net regularized CoxPH survival predictor model, where "optimal" indicates that the values of the hyperparameters "alpha" and "lambda" were selected so as to minimize the 5-fold cross-validated error of the corresponding elastic net regularized CoxPH survival predictor model (a process which yielded alpha = 1 and lambda = 0.026278).)

| Covariate | Coefficient |
|---|---|
| age | 0.843974 |
| cardiovascular_disease | 0.110582 |
| years_smoking | 0.085188 |
| cg00141845 | −0.0168 |
| cg02082843 | 0.061002 |
| cg02600394 | 0.061066 |
| cg03000846 | −0.0022 |
| cg03636183 | −0.13706 |
| cg05044994 | 0.000689 |

TABLE 3-continued (Covariate (clinical factor or methylation marker (CpG site); Coefficient: the coefficient optimal for the corresponding CpG site or clinical factor in the optimal elastic net regularized CoxPH survival predictor model, where "optimal" indicates that the values of the hyperparameters "alpha" and "lambda" were selected so as to minimize the 5-fold cross-validated error of the corresponding elastic net regularized CoxPH survival predictor model (a process which yielded alpha = 1 and lambda = 0.026278).)

| Covariate | Coefficient |
| --- | --- |
| cg05516537 | −0.03809 |
| cg06758848 | −0.04162 |
| cg11340260 | −0.02793 |
| cg14360917 | 0.018976 |
| cg15497991 | −0.01864 |
| cg16510657 | −0.00334 |
| cg17339202 | −0.01575 |
| cg18441959 | 0.011952 |
| cg18833140 | −0.00391 |
| cg20430631 | −0.00561 |
| cg21494379 | −0.06331 |
| cg06015525 | 0.000146 |

Example 10: Building Predictor Models Using Machine Learning Methods—Elastic Net Regularized CoxPH Regression with a Large Set of Methylation Markers in Combination with Clinical Factors Multi-methylation marker survival predictor models including clinical factor covariates can be created as described in Example 9 using the full set of all methylation markers described in Example 4.

The methylation data for 485512 methylation sites were collected using the HM450 BeadChip, Illumina (as described in Examples 3 and 4). A multi-methylation marker survival predictor model of all-cause mortality including clinical factor covariates was built using elastic net regularized regression as described in Example 9.

To estimate the generalization performance of the survival predictor model, the hazard ratio and concordance of the survival predictor model was calculated using nested 5-fold cross-validation as described in Example 7.

The regression for the survival predictor model resulted in 132 methylation markers and 3 clinical factors with non-zero coefficients out of the set of methylation markers reduced from the original 485512 markers using the data cleaning methods described in Example 6 and the set of 15 clinical factors (HR=3.1469; concordance=0.7872; Table 4).

This multi-methylation marker and multi-clinical factor survival predictor model shows greater generalization performance compared to the multi-methylation marker survival predictor model of Example 9 created using a smaller subset of methylation sites, indicating that the machine learning techniques described herein would lead to survival predictor models having even greater generalization performance if implemented on larger sets of methylation data having an increased number of methylation sites.

TABLE 4

(Covariate (clinical factor or methylation marker (CpG site); Coefficient: the coefficient for the corresponding CpG site or clinical factor in the optimal elastic net regularized CoxPH survival predictor model, where the "optimal" that the values of the hyperparameters "alpha" and "lambda" were selected so as to minimize the 5-fold cross-validated error of the predictive model (a process which yielded alpha = 1 and lambda = 0.022097)).

| Covariate | Coefficient |
| --- | --- |
| age | 0.808722 |
| cardiovascular_disease | 0.121482 |
| years_smoking | 0.037132 |
| cg07965774 | 0.009072 |
| cg23814214 | −0.00216 |
| cg16138181 | −0.00419 |
| cg12717729 | −0.02883 |
| cg16401270 | −0.01755 |
| cg11193462 | 0.039239 |
| cg13871826 | −0.0143 |
| cg19361456 | 0.022571 |
| cg03610604 | 0.005337 |
| cg10573505 | 0.000868 |
| cg26677288 | −0.0213 |
| cg05360477 | −0.0343 |
| cg07548255 | 0.016727 |
| cg05971072 | −0.00306 |
| cg23023604 | 0.002989 |
| cg19281794 | 0.056892 |
| cg10773224 | −0.00602 |
| cg09573795 | 0.006832 |
| cg11078084 | 0.014936 |
| cg15586439 | 0.000735 |
| cg04813875 | 0.023573 |
| cg05575921 | −0.15021 |
| cg08238319 | 0.040898 |
| cg00409356 | 0.009505 |
| cg22978003 | 0.007986 |
| cg19419291 | −0.02367 |
| cg11937703 | 0.003771 |
| cg11339912 | −0.01386 |
| cg25090510 | −0.0447 |
| cg01425680 | 0.005387 |
| cg16006841 | −0.01344 |
| cg09842479 | −0.00858 |
| cg26987613 | −0.03359 |
| cg03546163 | −0.06871 |
| cg25114611 | −0.06227 |
| cg15478981 | 0.003699 |
| cg24900370 | −0.02759 |
| cg22985172 | 0.037826 |
| cg11454936 | 0.008267 |
| cg12400790 | 0.015813 |
| cg03366574 | 0.051667 |
| cg25975690 | −0.00811 |
| cg00137629 | 0.006549 |
| cg10691866 | −0.00755 |
| cg13234848 | −0.00391 |
| cg07602571 | 0.002236 |
| cg17583077 | 0.00345 |
| cg24285543 | 0.021921 |
| cg18107989 | 0.000608 |
| cg15310871 | 0.010624 |
| cg14195992 | −0.00212 |
| cg18029167 | −0.01903 |
| cg08792272 | 0.01791 |
| cg25473866 | 0.030616 |
| cg01863081 | 0.03793 |
| cg20784950 | −0.03764 |
| cg18000391 | 0.005756 |
| cg07980830 | −0.01439 |
| cg13982318 | −0.03762 |
| cg14396892 | 0.020238 |
| cg00008629 | −0.02459 |
| cg14138047 | 0.000609 |
| cg14541800 | −0.03232 |
| cg03672997 | −0.01569 |
| cg23648810 | 0.005904 |
| cg04406111 | 0.012743 |
| cg02124758 | −0.00632 |

TABLE 4-continued (Covariate (clinical factor or methylation marker (CpG site); Coefficient: the coefficient for the corresponding CpG site or clinical factor in the optimal elastic net regularized CoxPH survival predictor model, where the "optimal" that the values of the hyperparameters "alpha" and "lambda" were selected so as to minimize the 5-fold cross-validated error of the predictive model (a process which yielded alpha = 1 and lambda = 0.022097)).

| Covariate | Coefficient |
| --- | --- |
| cg00321709 | 0.016134 |
| cg24577116 | 0.004622 |
| cg13632983 | 0.025828 |
| cg04733365 | −0.00566 |
| cg12535090 | 0.000754 |
| cg03447554 | −1.20E−05 |
| cg02791145 | −0.03315 |
| cg14161454 | 0.006645 |
| cg13273340 | 0.001085 |
| cg02100918 | 0.020947 |
| cg17058475 | −0.00245 |
| cg12491115 | 3.63E−05 |
| cg01039401 | 0.002943 |
| cg07178945 | 0.025626 |
| cg02519286 | −0.01928 |
| cg17817168 | 0.000448 |
| cg05921581 | −0.0004 |
| cg02384661 | −0.01277 |
| cg02021442 | −0.03415 |
| cg00308065 | 0.012028 |
| cg00748494 | −0.00125 |
| cg01906637 | 0.035198 |
| cg16763443 | 0.001973 |
| cg11190278 | 0.01665 |
| cg09954698 | 0.004931 |
| cg25132241 | 0.005179 |
| cg26102435 | 0.028249 |
| cg07197326 | 0.006508 |
| cg23811289 | 0.005125 |
| cg09970175 | 0.004967 |
| cg02812767 | −0.07323 |
| cg12101586 | −0.03435 |
| cg23633568 | −0.00332 |
| cg08428878 | 0.002501 |
| cg02481950 | 0.008377 |
| cg01355753 | −0.03331 |
| cg02531193 | 0.008276 |
| cg16376828 | −0.01784 |
| cg10241823 | 0.016286 |
| cg22748407 | −0.00558 |
| cg19789473 | −0.01911 |
| cg02486253 | 0.002025 |
| cg15756507 | 0.047154 |
| cg24181662 | −0.01238 |
| cg17807001 | 0.005752 |
| cg19590707 | −0.00337 |
| cg13765206 | −0.02277 |
| cg17318716 | 0.005239 |
| cg07573872 | −0.05191 |
| cg00804433 | 0.007634 |
| cg04234014 | 0.000291 |
| cg16526705 | 0.004168 |
| cg11249283 | −0.04559 |
| cg19477346 | −0.01079 |
| cg03707168 | −0.02684 |
| cg08559712 | 0.011009 |
| cg00871610 | −0.05456 |
| cg14162806 | −0.0082 |
| cg05072413 | −0.03602 |
| cg13909895 | −0.00518 |
| cg16088894 | 0.012475 |
| cg06128881 | −0.01247 |
| cg00141845 | −0.00595 |
| cg27590787 | −0.00484 |
| cg11898347 | −0.01892 |

Example 11: Building Predictor Models Using Elastic Net Regularized CoxPH Regression with Methylation Markers in Combination with Clinical Factor Covariates—Varying Regularization Parameters Multi-methylation marker survival predictor models including clinical factor covariates were created as described in Example 10 with varying regularization parameters. We created 5 such survival predictor models with elastic net regularized CoxPH regression, setting the hyperparameter alpha to 1 and the hyperparameter lambda to the values 0.0625, 0.05226, 0.044194, 0.037163, and 0.03125.

To estimate the generalization performance of the survival predictor models, the hazard ratios and concordances of the survival predictor models were calculated using nested 5-fold cross-validation, with each calculation proceeding as described in Example 7.

The resulting 5 multi-methylation marker survival predictor models using hyperparameter lambda=0.0625, 0.05226, 0.044194, 0.037163, and 0.03125, respectively, had 1, 2, 12, 19, and 29 methylation markers and 1, 1, 2, 2, and 3 clinical factors, respectively (HRs=2.6016, 2.7131, 2.8537, 3.0304, and 3.1446 respectively; concordances=0.7393, 0.7477, 0.7595, 0.7725, and 0.7829 respectively; Tables 6, 7, 8, 9, and 10 respectively).

These multi-methylation marker survival predictor models demonstrate that using survival predictor models having higher numbers of methylation markers can result in higher hazard ratios with the use of the same or suitable modified machine learning techniques described herein.

TABLE 5

(Covariate (clinical factor or methylation marker (CpG site); Coefficient: the coefficient for the corresponding CpG site or clinical factor in the optimal elastic net regularized CoxPH survival predictor model with lambda = 0.0625, where "optimal" indicates that the aforementioned value of lambda was used, and the value of the hyperparameter "alpha" was chosen so as to minimize the 5-fold cross-validated error of the predictor model (a process which yielded alpha = 1)).

| Covariate | Coefficient |
| --- | --- |
| age | 0.938717 |
| cg03707168 | 0.02278 |

TABLE 6

(Covariate (clinical factor or methylation marker (CpG site); Coefficient: the coefficient for the corresponding CpG site or clinical factor in the optimal elastic net regularized CoxPH survival predictor model with lambda = 0.02556, where "optimal" indicates that the aforementioned value of lambda was used, and the value of the hyperparameter "alpha" was selected to as to minimize the 5-fold cross-validated error of the predictor model (a process which yielded alpha = 1)).

| Covariate | Coefficient |
| --- | --- |
| age | 0.920076 |
| cg25975690 | −0.00494 |
| cg03707168 | −0.10137 |

TABLE 7

(Covariate (clinical factor or methylation marker (CpG site); Coefficient: the coefficient for the corresponding CpG site or clinical factor in the optimal elastic net regularized CoxPH survival predictor model with lambda = 0.044194, where "optimal" indicates that the aforementioned value of lambda was chosen, and the value of the hyperparameter "alpha" was selected so as to minimize the 5-fold cross-validated error of the predictor model (a process which yielded alpha = 1)).

| Covariate | Coefficient |
| --- | --- |
| age | 0.89832 |
| cardiovascular_disease | 0.032088 |
| cg12717729 | −0.00628 |
| cg01940273 | −0.00659 |
| cg05575921 | −0.04514 |
| cg26987613 | −0.01725 |
| cg25114611 | −0.01247 |
| cg25975690 | −0.02607 |
| cg10691866 | −0.00922 |
| cg25179876 | −0.00623 |
| cg12101586 | −0.0072 |
| cg07890785 | −0.00201 |
| cg03636183 | −0.00781 |
| cg03707168 | −0.11693 |

TABLE 8

(Covariate (clinical factor or methylation marker (CpG site); Coefficient: the coefficient for the corresponding CpG site or clinical factor in the optimal elastic net regularized CoxPH survival predictor model with lambda = 0.037163, where "optimal" indicates that the elastic net predictor model with the aforementioned value of lambda was chosen, and the value of the hyperparameter "alpha" was selected so as to minimize the 5-fold cross-validated error of the predictor model (a process which yielded alpha = 1)).

| Covariate | Coefficient |
| --- | --- |
| age | 0.865128 |
| cardiovascular_disease | 0.064228 |
| cg12717729 | −0.02016 |
| cg15459165 | 0.020928 |
| cg05575921 | −0.09764 |
| cg26987613 | −0.01995 |
| cg03546163 | −0.02572 |
| cg25114611 | −0.02762 |
| cg03366574 | 0.029192 |
| cg25975690 | −0.03118 |
| cg10691866 | −0.02308 |
| cg08792272 | 0.005577 |
| cg02519286 | −0.01828 |
| cg02812767 | −0.02405 |
| cg12101586 | −0.02648 |
| cg07890785 | −4.50E−05 |
| cg07573872 | −0.00809 |
| cg03636183 | −0.00463 |
| cg11249283 | −0.00264 |
| cg03707168 | −0.09928 |
| cg08559712 | 0.006034 |

TABLE 9

(Covariate (clinical factor or methylation marker (CpG site); Coefficient: the coefficient for the corresponding CpG site or clinical factor in the optimal elastic net regularized CoxPH survival predictor model with lambda = 0.03125, where "optimal" indicates that aforementioned value of lambda was chosen, and the hyperparameter "alpha" was selected so as to minimize the 5-fold cross-validated error of the predictor model (a process which yielded alpha = 1)).

| Covariate | Coefficient |
| --- | --- |
| age | 0.833135 |
| cardiovascular_disease | 0.088182 |
| years_smoking | 0.017062 |
| cg12717729 | −0.02912 |
| cg15459165 | 0.013772 |
| cg05360477 | −0.00594 |
| cg19281794 | 0.026675 |
| cg05575921 | −0.12424 |
| cg19419291 | −0.00652 |
| cg25090510 | −0.00444 |
| cg11770816 | 0.021854 |
| cg26987613 | −0.01914 |
| cg03546163 | −0.05087 |
| cg25114611 | −0.04071 |
| cg03366574 | 0.062101 |
| cg25975690 | −0.03451 |
| cg10691866 | −0.02305 |
| cg08792272 | 0.013326 |
| cg25473866 | 0.002676 |
| cg00008629 | −0.01524 |
| cg18825531 | −0.00055 |
| cg02519286 | −0.02588 |
| cg02812767 | −0.04041 |
| cg12101586 | −0.04043 |
| cg07890785 | −0.00038 |
| cg15756507 | 0.022406 |
| cg13765206 | −0.00017 |
| cg07573872 | −0.03171 |
| cg11249283 | −0.0159 |
| cg03707168 | −0.06523 |
| cg08559712 | 0.011144 |
| cg00871610 | −0.00968 |

Example 12: Building Predictor Models Using Elastic Net Regularized CoxPH Regression Trained on Subpopulations Having Selected Values for Certain Clinical Factors Multi-methylation marker survival predictor models including clinical factor covariates were created as described in Example 10 (i.e., using elastic net regularized CoxPH regression) using only data from a subpopulation of individuals represented in the data cohort. In each case, the survival predictor model was created with a subset of the data corresponding exclusively to individuals all possessing given values of selected clinical factors. It is understood that the values and/or clinical factors used may be varied leading to different survival predictor models.

We created 2 such survival predictor models with elastic net regularized CoxPH regression, setting the hyperparameter alpha to 1, using the subset of the data corresponding to male individuals for the first model and the subset of the data corresponding to female individuals for the second model.

To estimate the generalization performance of the survival predictor models, the hazard ratios and concordances of the survival predictor models were calculated using nested 5-fold cross-validation, with each calculation proceeding as described in Example 7.

Using the data corresponding exclusively to male subjects, we obtained a survival predictor model with 30 methylation markers and 1 clinical factor (HR=2.7434; concordance=0.7531; Table 10).

TABLE 10

(Covariate (clinical factor or methylation marker (CpG site);
Coefficient: the coefficient for the corresponding CpG site or
clinical factor in the optimal elastic net regularized CoxPH survival
predictor model, where the hyperparameter alpha was set to 1, and
where "optimal" indicates that the value of the hyperparameter
lambda was selected so as to minimize the 5-fold cross-validated
error of the corresponding elastic net regularized CoxPH survival
predictor model (a process which yielded lambda = 0.04419)).

| Covariate | Coefficient |
| --- | --- |
| age | 0.937678 |
| cg16552271 | 0.010861 |
| cg21386573 | −0.03184 |
| cg26875665 | 0.000517 |
| cg01200177 | −0.00611 |
| cg12756150 | 0.074438 |
| cg04389058 | −0.00982 |
| cg05575921 | −0.1 |
| cg15556672 | −0.00984 |
| cg07465864 | −0.00284 |
| cg14640659 | −0.02449 |
| cg18468088 | −0.0155 |
| cg19039673 | 0.035115 |
| cg10459111 | −0.00208 |
| cg12535090 | 0.009851 |
| cg26786382 | 0.021226 |
| cg02519286 | −0.07098 |
| cg09954698 | 0.010827 |
| cg10196163 | −0.01668 |
| cg21467108 | −0.06718 |
| cg00701514 | 0.016125 |
| cg24395672 | 0.035792 |
| cg09119854 | 0.015721 |
| cg07573872 | −0.00236 |
| cg21500303 | −0.00509 |
| cg22857356 | 0.002424 |
| cg16526705 | 0.083675 |
| cg26470501 | −0.0189 |
| cg09565639 | −0.02759 |
| cg20098015 | −0.01883 |
| cg06462425 | 0.011592 |

Using the data corresponding exclusively to female subjects, we obtained a survival predictor model with 29 methylation markers and 4 clinical factors (HR=3.1510; concordance=0.8000; Table 11).

TABLE 11

(Covariate (clinical factor or methylation marker (CpG site); Coefficient:
the coefficient for the corresponding CpG site or clinical factor
in the optimal elastic net regularized CoxPH survival predictor model,
where the hyperparameter alpha was set to 1, and where "optimal"
indicates that the value of the hyperparameter lambda was selected so
as to minimize the 5-fold cross-validated error of the corresponding
elastic net regularized CoxPH survival predictor
model (a process which yielded lambda = 0.03125)).

| Covariate | Coefficient |
| --- | --- |
| age | 0.788907 |
| cardiovascular_disease | 0.082494 |
| years_smoking | 0.043094 |
| slight_physical | −0.07562 |
| cg09182189 | −0.04407 |
| cg24629455 | −0.0069 |
| cg10117369 | 0.0088 |
| cg10950251 | −0.01645 |
| cg07582862 | −0.05072 |
| cg05575921 | −0.06913 |
| cg03546163 | −0.1394 |
| cg18828861 | −0.02247 |
| cg22374237 | 0.017843 |
| cg10473158 | −0.05727 |
| cg12728958 | −0.00028 |
| cg07671678 | −0.00552 |
| cg20784950 | −0.07701 |
| cg14396892 | 0.010262 |
| cg14541800 | −0.05743 |
| cg19854666 | 0.012588 |
| cg25592907 | −0.01604 |
| cg17324880 | 0.10339 |
| cg12286415 | 0.068488 |
| cg01671212 | −0.0005 |
| cg23811289 | 0.001548 |
| cg02812767 | −0.23136 |
| cg08726900 | 0.00837 |
| cg08446357 | 0.02212 |
| cg01572694 | −0.01558 |
| cg21576590 | 0.017819 |
| cg06804705 | −0.06731 |
| cg24117676 | 0.001018 |
| cg26499822 | −0.05744 |

We compared the performance of the aforementioned survival predictor models to the performance of elastic net regularized CoxPH regression survival predictor models trained on random subsets of the entire set of data. Each random subset was selected such that both the number of living individuals and the number of dead individuals represented in the random subset are identical to the number of living individuals and the number of dead individuals represented in the subset of the entire set of data corresponding to individuals with a given value of the selected clinical factor (gender).

To estimate the generalization performance of these survival predictor models, the hazard ratios and concordances of the survival predictor models were calculated using nested 5-fold cross-validation, with each calculation proceeding as described in Example 7.

We selected 10 random subsets of the data such that each random subset included 992 living individuals and 202 dead individuals, corresponding to the numbers of alive and dead individuals in the male subpopulation of the entire dataset. We trained a survival predictor model as described in Example 10 on each of these random subsets of data and obtained 10 survival predictor models with an average hazard ratio of 2.4130 and an average concordance of 0.7403 (Table 12).

TABLE 12

(Run Number; Hazard ratio: The 5-fold cross-validated hazard ratio of the survival predictor model trained using the random subset of the entire set of methylation data; Concordance: The 5-fold cross-validated concordance of the survival predictor model trained using the random subset of the entire set of data.).

| Run Number | Hazard ratio | Concordance |
|---|---|---|
| 1 | 2.24006056483055 ± 1.07236433982838 | 0.725801586503606 ± 0.0214406123144625 |
| 2 | 2.44841338026326 ± 1.07592618542407 | 0.732577258737721 ± 0.0213913012246267 |
| 3 | 2.63524647724304 ± 1.0774108486124 | 0.753170562003858 ± 0.0213881978693082 |
| 4 | 2.50162541655271 ± 1.07344936242469 | 0.753947031026778 ± 0.0213487360916529 |
| 5 | 2.08776959402879 ± 1.07094029853629 | 0.713462016578239 ± 0.0214499111775477 |
| 6 | 2.39022197931187 ± 1.07516797512841 | 0.738262670756968 ± 0.0213768278580183 |
| 7 | 2.74889845524337 ± 1.07507778409799 | 0.766287834365705 ± 0.0215134475774756 |
| 8 | 2.55387498944604 ± 1.07185700390123 | 0.757468676326455 ± 0.0214607149634916 |
| 9 | 2.43061997737047 ± 1.07300635180629 | 0.736208562665434 ± 0.0213812423920803 |
| 10 | 2.09350299230992 ± 1.06909260401178 | 0.726322191664904 ± 0.0213984089447506 |

We selected another 10 random subsets of the data such that each random subset included 1269 living individuals and 149 dead individuals, corresponding to the numbers of alive and dead individuals in the female subpopulation of the entire dataset. We trained a survival predictor model as described in Example 10 on each of these random subsets of data and obtained 10 survival predictor models with an average hazard ratio of 2.3285 and an average concordance of 0.7342 (Table 13).

TABLE 13

(Run Number; Hazard ratio: The 5-fold cross-validated hazard ratio of the survival predictor model trained using the random subset of the entire set of data; Concordance: The 5-fold cross-validated concordance of the survival predictor model trained using the random subset of the entire set of methylation data.).

| Run Number | Hazard ratio | Concordance |
|---|---|---|
| 1 | 2.1986071947649 ± 1.0806092381513 | 0.724801272783226 ± 0.024630244758848 |
| 2 | 2.38644479681102 ± 1.08085858729001 | 0.7492748212183 ± 0.0244658403812026 |
| 3 | 2.41694655824455 ± 1.08284427551414 | 0.747273649505453 ± 0.0245364620986431 |
| 4 | 2.30278852603165 ± 1.07620262887894 | 0.743508368611399 ± 0.0243920793286694 |
| 5 | 2.44271603658809 ± 1.08050606902264 | 0.75813517439337 ± 0.0245140321755802 |
| 6 | 2.36547496043207 ± 1.08396043744312 | 0.73186538834232 ± 0.0244622840398397 |
| 7 | 2.27409354638866 ± 1.08287526606428 | 0.721067967668468 ± 0.02422141305926 |
| 8 | 2.14636553127592 ± 1.08052921048975 | 0.710587118395919 ± 0.0244633879970334 |
| 9 | 2.60031212311504 ± 1.08801626354296 | 0.743981064925985 ± 0.0244791771094464 |
| 10 | 2.15150536096812 ± 1.08070669043171 | 0.711090926528747 ± 0.0243491946753389 |

Thus, multi-methylation marker survival predictor models with clinical factor covariates trained on subsets of data corresponding to selected values of a clinical factor (sex) showed higher generalization performance compared to multi-methylation marker survival predictor models with clinical factor covariates trained on identically sized random subsets of the data having identical fractions of alive individuals, indicating that the machine learning techniques exhibited herein may be straightforwardly applied to subsets of the data, where the subsets have specific values for selected clinical factors, to obtain survival predictor models with higher generalization performance compared to survival predictor models trained on subsets of the data of comparable size without the aforementioned restriction.

Example 13: Building Predictor Models Using Principal Component Analysis (PCA) and Support Vector Machines (SVMs) with Methylation Markers and Clinical Factor Covariates Many alternative approaches of machine learning can be used to build predictor models based on survival biomarkers of mortality based on methylomic data. Here we illustrate this using the example of a ranking-based regularized survival Support Vector Machines (SVM) as described above and in further detail by Pölsterl et al. (S. Pölsterl, N. Navab, A. Katouzian. 2015. Fast Training of Support Vector Machines for Survival Analysis. Machine Learning and Knowledge Discovery in Databases), which is herein incorporated by reference in its entirety, in combination with principal component analysis (PCA) as described above and in further detail by Dunteman (G. H. Dunteman, 1989. Principal Components Analysis), which is herein incorporated by reference in its entirety.

Each methylation marker was controlled for all of the clinical factors described in Example 8 (namely: age, sex, systolic blood pressure, diastolic blood pressure, whether an individual has high cholesterol or not, whether an individual has cardiovascular disease or not, whether an individual has high blood sugar or not, whether an individual is a smoker or not, the number of cigarettes smoked per day, the number of years an individual has smoked, the number of days per week an individual drinks alcohol, the number of drinks of alcohol per day, the number of hours per day for which an individual engages in mild physical activity, the number of hours per day for which an individual engages in moderate physical activity, and the number of hours per day for which an individual engages in heavy physical activity) using multivariate linear regression prior to the computation of principal components.

The method of PCA was applied as provided in the flashpcaR package for R (Abraham G and Inouye M (2014).

"Fast Principal Component Analysis of Large-Scale Genome-Wide Data."_PLOS ONE_, *9(4)*, pp. e93766. R package version 2.0, <URL: CRAN.R-project.org/package=flashpcaR>) to extract the first 50 principal components of the set of all methylation markers after controlling for clinical factors.

We repeated the following procedure 20 times: (1) We randomized a balanced split (comprising approximately the same fraction of death and non-death events in each bucket) setting aside 80% of the data for a training set and 20% testing set. (2) Using the 50 principal components previously calculated and both with and without clinical factor covariates, we fit weights using a survival SVM using a rank-based approach described in further detail above. We chose the regularization coefficient by another 5-fold cross-validation within the 80% training set (nested cross-validation), using a grid search. Using the best value, we fit weights on the entire training set (80% of the entire data) and used those weights for evaluation on the 20% test set.

While a survival predictor model only using the 50 principal components has a log-HR of 0.1594 (±0.1804), with Harrell's concordance index c=0.5421 (±0.0345), using the clinical factor covariates (age, sex, systolic blood pressure, diastolic blood pressure, whether an individual has high cholesterol or not, whether an individual has cardiovascular disease or not, whether an individual has high blood sugar or not, whether an individual is a smoker or not, the number of cigarettes smoked per day, the number of years an individual has smoked, the number of days per week an individual drinks alcohol, the number of drinks of alcohol per day, the number of hours per day for which an individual engages in mild physical activity, the number of hours per day for which an individual engages in moderate physical activity, and the number of hours per day for which an individual engages in heavy physical activity) along with the 50 principal components resulted in a survival predictor model having a log-HR of 1.1155 (±0.159), Harrell's concordance index c=0.7947 (±0.0199). These numbers are comparable to the results using elastic net regularized CoxPH for Example 10.

Example 14: An Alternative Cohort Based on the Normative Aging Study for Construction and Evaluation of Survival Predictor Models In order to study methylation sites (CpG sites) that are associated with aging, another study cohort was designed. Study subjects were drawn from the Normative Aging Study (Marioni et al., "DNA methylation age of blood predicts all-cause mortality in later life", published in Genome Biology in 2015, accessible online at 10.1186/s13059-015-0584-6). 657 subjects were used for the study, which excluded 18 cohort participants who were not of European descent or had missing racial background information. The age of the subjects had a mean of 72.9 and a standard deviation of 6.9. Members of the Normative Aging Study began to be enrolled in 1963 and included men between 21 and 80 years of age who were free of known medical conditions at entry. Participants were invited to medical examinations every 3 to 5 years after enrollment. For the 657 subjects in the study cohort, 226 deaths were recorded.

Biological samples from the Normative Aging Study cohort were processed thusly: DNA was extracted from the buffy coat portion of blood with a QIAamp DNA Blood Kit. 500 ng of DNA from each person was used to perform bisulfite conversion with an EZ-96 DNA Methylation Kit. A two-stage age-stratified algorithm was used to randomize sample placement prior to methylation analysis. Quality control analysis was performed to remove samples for which over 1% of methylation probes had a detection P value greater than 0.05. Illumina-type background correction without normalization was applied to the remaining samples. The Bioconductor minfi package was used to generate methylation beta values—the ratio of intensities between methylated and unmethylated alleles. Methylation beta values were used to generate methylation fractions with the following relationship: methylation fraction=(methylation beta value)/(1+methylation beta value), which was derived from the definitions of (1) methylation beta value=(methylated markers)/(unmethylated markers) and (2) methylation fraction=(methylated markers)/(methylated markers+unmethylated markers).

The Normative Aging Study methylation data are accessible at www.ncbi.nlm.nih.gov/projects/gap/cgi-bin/study.cgi?study_id=phs000853.v1.p1.

Example 15: Comparison of Survival Predictor Models for all-Cause Mortality with Survival Biomarkers from Multiple Studies Predictor models of all-cause mortality were built to predict mortality for subjects in the Framingham methylation data. A first group of 10 CpG sites (cg01612140, cg05575921, cg06126421, cg08362785, cg10321156, cg14975410, cg19572487, cg23665802, cg24704287 and cg25983901) and a second group of 58 CpG sites (cg03725309, cg25763716, cg13854219, cg25189904, cg15459165, cg19266329, cg24397007, cg23079012, cg27241845, cg06905155, cg16503724, cg19859270, cg02657160, cg14975410, cg14855367, cg05575921, cg14817490, cg21161138, cg12513616, cg20732076, cg25285720, cg06126421, cg15342087, cg01612140, cg25983901, cg12510708, cg26286961, cg00285394, cg01140244, cg23190089, cg07123182, cg26963277, cg18550212, cg10321156, cg25193885, cg07986378, cg23665802, cg04987734, cg19459791, cg00310412, cg26709988, cg23842572, cg19572487, cg01572694, cg08546016, cg18181703, cg03636183, cg24704287, cg11341610, cg14085840, cg26470501, cg05492306, cg25607249, cg01406381, cg07626482, cg03707168, cg25491402, and cg08362785) were evaluated as survival biomarkers (see "DNA methylation signatures in peripheral blood strongly predict all-cause mortality", by Zhang et al. (2017), published in Nat. Commun. 8: 14617, published online 2017 Mar. 17. doi: 10.1038/ncomms14617, herein incorporated by reference in its entirety for use of methylation biomarkers in predictive models relating to mortality and mortality associated diseases.)

The numerical methylation scores for the CpG markers cg01612140, cg05575921, cg06126421, cg08362785, cg10321156, cg14975410, cg19572487, cg23665802, cg24704287 and cg25983901 were multiplied by the weight coefficients −0.38253, −0.92224, −1.70129, 2.71749, −0.02073, −0.04156, −0.28069, −0.89440, −2.98637, and −1.80325 and then summed, such that for each particular individual represented in the Framingham methylation data, the corresponding risk score was equal to the sum of the numeric methylation values for each of the ten methylation markers weighted by the respective weight coefficients. Ten-fold cross validation was used to evaluate the performance of a linear Cox proportional hazards model using this risk score alone as a predictor variable, and a concordance index of 0.5926 was attained.

The 485512 methylation markers from the Framingham Heart Study were controlled for clinical factors as described above and a nonlinear predictive model for all-cause mortality was built thusly: The random seed was set to 1. A regularized elastic net regression model with the hyperparameter alpha set equal to 1 was fit on the set of 485512 methylation markers, with the value of the hyperparameter lambda selected by a 5-fold cross-validated grid search over the values of lambda of the form $2^{-x}$ where x is one of 3, 3.125, 3.25, 3.375, 3.5, 3.615, 3.75, 3.875, 4, 4.125, 4.25, 4.375, 4.5, 4.625, 4.75, 4.875, 5, 5.125, and 5.25. Let the optimum value of lambda denote the value of lambda, where lambda is the hyperparameter of the elastic net regression model controlling the strength of regularization, for which the cross-validated root mean square error of the elastic net predictor model is minimized. Let the effective maximal value of lambda denote the least value of lambda, out of the values of lambda evaluated by the 5-fold cross-validated grid search, for which the number of methylation markers selected as predictor variables with nonzero coefficients by the elastic net predictor model was zero. Let the intermediate optimal value of lambda be the value of lambda, selected from the values of lambda evaluated by the cross-validated grid search which fall strictly between the optimum value of lambda and the effective maximal value of lambda, for which the cross-validated mean square error is closest to the average of the cross-validated root mean square errors associated with the optimum value of lambda and the effective maximal value of lambda, as calculated by the cross-validated grid search during the training of the elastic net predictor model. Let the one standard error value of lambda be the greatest value of lambda, out of those values of lambda evaluated by the cross-validated grid search, for which the root mean square error associated with the value of lambda, as calculated by the cross-validated grid search, is at most one standard error greater than the minimum of the root mean square errors associated with each value of lambda, again as calculated by the cross-validated grid search. There were no non-zero coefficients in the survival predictor model associated with the one standard error value of lambda.

The set of predictor variables, i.e. the methylation markers associated with nonzero coefficients in the elastic net regression model with the value of lambda set equal to the intermediate optimal value of lambda, was adjoined to the methylation markers cg01612140, cg05575921, cg06126421, cg08362785, cg10321156, cg14975410, cg19572487, cg23665802, cg24704287 and cg25983901 (except for those already represented to avoid repeats), herein collectively referred to as the set of augmented methylation markers. The random seed was set to 1. A nonlinear predictor model for survival was fit using gradient boosting with the Cox proportional hazard loss function (implemented as the method "gbm" in version 2.1.3 of the package "gbm" in R version 3.4.0, with distribution="cox."). We used the interaction depth set to 2 to model nonlinearity, and set the shrinkage parameter equal to 0.0005. To evaluate the performance of the nonlinear predictive model and select the number of trees used in "gbm", the entire process described above was evaluated via 10-fold cross-validation, yielding a cross-validated concordance index of 0.612. This concordance was attained with a "gbm" model with number of trees in model=11,000.

Figure 2:
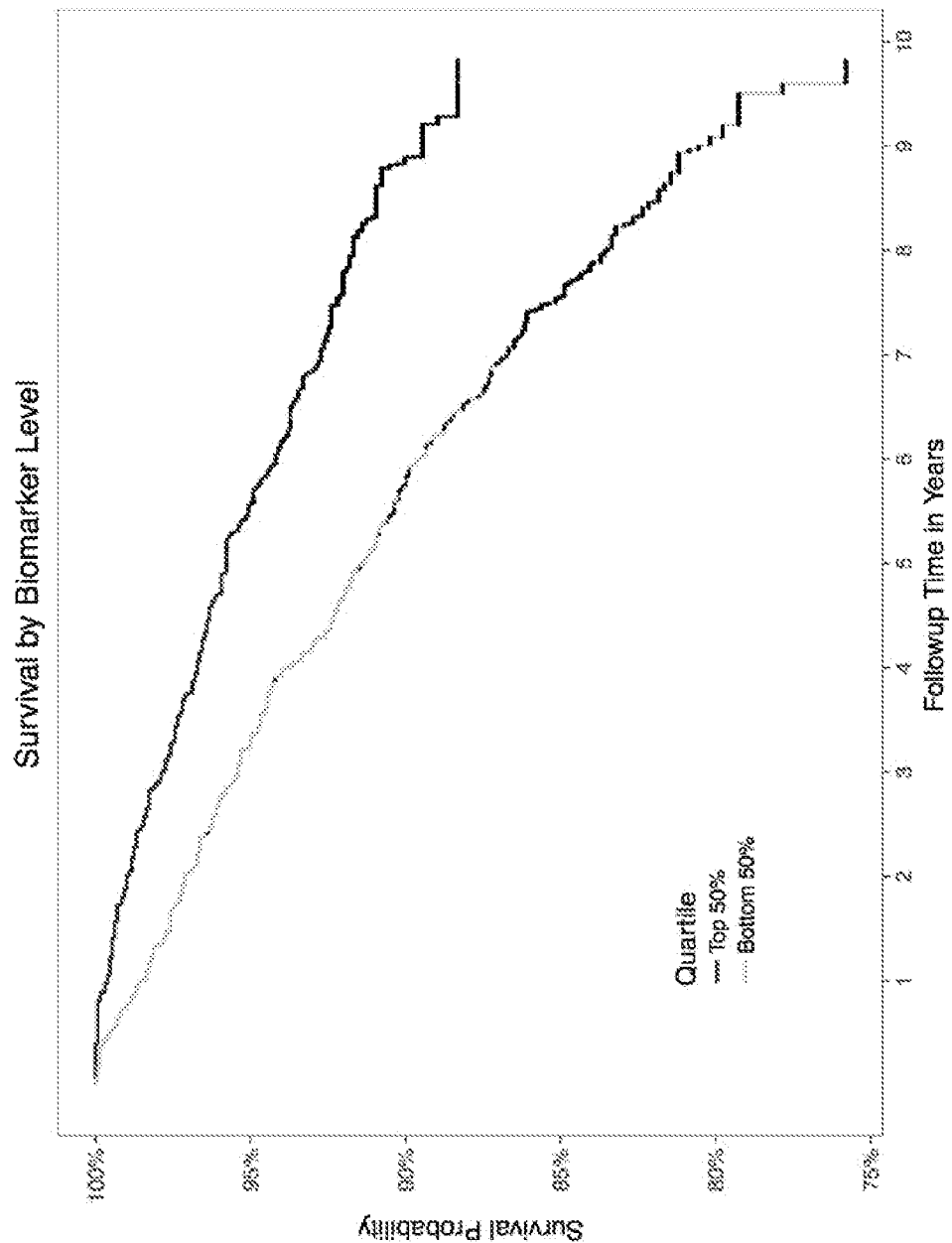
FIG. 2 illustrates a survival curve example for a survival predictor model built using gradient boosted machines using measured methylation markers.

To determine a final model, we performed the above process using the entire dataset for training. We set the random seed equal to 1. LASSO regression selected the methylation markers cg26987613, cg00252813 and cg07890785 when the intermediate lambda of $2^{-4.5}$ was used. We then set the random seed equal to 1 again, and trained "gbm" on the union of these and the first group of 10 CpG sites (in the order in which the 13 markers appear in the original dataset) with boosting hyperparameters given by interaction depth equal to 2, shrinkage equal to 0.0005 and number of trees equal to 11,000. This yielded our first final model. FIG. 2 shows the survival curve example for this first final model. The survival curves are for the top 50% most likely to survive and bottom 50% most likely to survive according to the cross-validated predictions in connection with the concordance index 0.612.

We also generated a second final model using the same process, except that after using LASSO to select the markers cg26987613, cg00252813 and cg07890785, gbm was used with parameters setting the interaction depth to 2, shrinkage to 0.0005, and the number of trees to 100 to illustrate a smaller example of a similar model. Table 14, produced at the end of the detailed description below, specifies this model.

Our first final model having 11,000 trees using methylation markers including but not restricted to the first group of 10 CpG sites attained a higher cross-validated concordance than the linear model constructed from the risk score (calculated from the first group of 10 CpG sites as described above).

Example 16: Evaluation of Survival Predictor Models for all-Cause Mortality with Survival Biomarkers from Multiple Studies on Different Study Cohorts We further evaluated survival predictor models on the Normative Aging Study methylation and mortality data.

A training subset of methylation sites was selected consisting of the shared methylation sites in the set of 26987 methylation sites that are available for sequencing by HumanMethylation27K BeadChip (HM27) (Illumina) and the set of 485512 sites from the Framingham methylation data. A predictor subset of methylation sites was selected from the training subset of methylation sites in the Framingham methylation data, which were i) represented in the Normative Aging Study methylation data, and ii) represented in the second group of 58 methylation markers identified above. Nonlinear survival predictor models with superior predictive power for mortality in the Normative Aging Study were created using methylation biomarkers from a variety of sources in comparison to survival predictor models comprising solely methylation biomarkers from the predictor subset of methylation sites.

The Normative Aging Study methylation data were controlled for the following clinical factors: age at time when blood was drawn, years of education, diabetes status/diagnosis, hypertension status/diagnosis, coronary heart disease status/diagnosis, number of neutrophils in blood, number of lymphocytes in blood, number of monocytes in blood, number of eosinophils in blood, number of basophils in blood, amount of smoking, and APOE4 status.

A first survival predictor model was created by building a linear model for mortality that was trained upon the training subset of methylation markers using, as predictor variables, the predictor subset of methylation sites. The generalizable performance of this linear model for predicting mortality in the Normative Aging Study was evaluated with 10-fold cross-validation and the linear model was found to attain a concordance index of 0.5720.

Using the training subset of methylation sites, a second survival predictor model for all-cause mortality was built thusly: The random seed was set to 1. The method described in Example 15 for the creation of a nonlinear predictor model was used to select optimal "gbm" hyperparameters for a nonlinear predictor model of mortality, except instead of adjoining the first group of 10 CpG sites described in Example 15, the predictor subset of methylation sites was adjoined to the markers associated with the intermediate optimal value of lambda. The selected hyperparameters were shrinkage=0.0005 and number of trees=5,000, with the interaction depth set to 2 to account for nonlinearity. Subsequently, without cross-validation, the method used for constructing the augmented set of methylation markers (as defined in Example 15 within the method for constructing the nonlinear predictor model of mortality), and again adjoining the predictor subset of methylation sites instead of the first group of 10 CpG sites described in Example 15, was applied to the training subset of methylation sites. A predictor-subset-informed augmented set of methylation markers was formed by adjoining the four methylation markers cg02679745, cg15814508, cg20430631, and cg00984060 to the predictor subset of methylation sites. The predictor-subset-informed augmented set of methylation markers was used with the previously determined optimal parameters of "gbm" to train a nonlinear "gbm" predictor model for mortality trained upon the training subset of methylation markers. Ten-fold cross-validation was applied to evaluate the generalizable performance of this second survival predictor model in regard to predicting mortality in the Normative Aging Study methylation data, and the model was found to attain a concordance index of 0.5896—a clear improvement over the first survival predictor model built using methylation biomarkers only from the predictor subset of methylation sites.

Additionally, the cross-validated concordance index associated with the optimal "gbm" parameters, trained and evaluated upon the Framingham methylation data alone, was 0.5896. In Example 15, we attained a greater cross-validated concordance for the nonlinear "gbm" model of 0.612, demonstrating that a machine learning technique may be applied on expanded sets of methylation sites leading to survival predictor models with greater generalization performance.

ADDITIONAL CONSIDERATIONS

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included in the invention, unless the context clearly dictates otherwise.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Various embodiments may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a tangible computer readable storage medium or any type of media suitable for storing electronic instructions, and coupled to a computer system bus. Furthermore, any computing systems referred to in the specification may include a single processor or may be architectures employing multiple processor designs for increased computing capability.

Various embodiments may also relate to a computer data signal embodied in a carrier wave, where the computer data signal includes any embodiment of a computer program product or other data combination described herein. The computer data signal is a product that is presented in a tangible medium or carrier wave and modulated or otherwise encoded in the carrier wave, which is tangible, and transmitted according to any suitable transmission method.

All publications, patents, and patent applications mentioned in this specification are herein incorporated by reference to the same extent as if each individual publication, patent, or patent application was specifically and individually indicated to be incorporated by reference.

While many embodiments have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed in practicing the invention. It is intended that the following claims define the scope of the invention and that methods and structures within the scope of these claims and their equivalents be covered thereby.

TABLE 14

| tree | node | SplitVar | SplitCodePred | LeftNode | RightNode |
|---|---|---|---|---|---|
| 1 | 0 | cg01612140 | −1.684748858 | 1 | 5 |
| 1 | 1 | cg10321156 | 0.809457929 | 2 | 3 |
| 1 | 2 | N/A | −0.003117068 | NA | NA |
| 1 | 3 | N/A | 0 | NA | NA |
| 1 | 4 | N/A | −0.001416849 | NA | NA |
| 1 | 5 | N/A | −0.003291442 | NA | NA |
| 1 | 6 | N/A | −0.003210831 | NA | NA |
| 2 | 0 | cg01612140 | −1.571674594 | 1 | 2 |
| 2 | 1 | N/A | 0.001120849 | NA | NA |
| 2 | 2 | cg07890785 | −2.052250942 | 3 | 4 |
| 2 | 3 | N/A | 0.002670737 | NA | NA |
| 2 | 4 | N/A | 0 | NA | NA |
| 2 | 5 | N/A | 2.22376E−05 | NA | NA |
| 2 | 6 | N/A | 8.92366E−05 | NA | NA |
| 3 | 0 | cg10321156 | 1.994012306 | 1 | 5 |
| 3 | 1 | cg26987613 | −1.652387261 | 2 | 3 |
| 3 | 2 | N/A | 0.001181856 | NA | NA |
| 3 | 3 | N/A | 0 | NA | NA |
| 3 | 4 | N/A | 4.96735E−05 | NA | NA |
| 3 | 5 | N/A | 0.003456003 | NA | NA |
| 3 | 6 | N/A | 9.76125E−05 | NA | NA |
| 4 | 0 | cg01612140 | −1.672499878 | 1 | 2 |
| 4 | 1 | N/A | 0.001471734 | NA | NA |
| 4 | 2 | cg26987613 | −2.109739335 | 3 | 4 |
| 4 | 3 | N/A | 0.00260561 | NA | NA |
| 4 | 4 | N/A | 0 | NA | NA |
| 4 | 5 | N/A | 3.44828E−05 | NA | NA |
| 4 | 6 | N/A | 0.000113144 | NA | NA |
| 5 | 0 | cg26987613 | −0.773685383 | 1 | 5 |
| 5 | 1 | cg05575921 | −1.37528495 | 2 | 3 |
| 5 | 2 | N/A | 0.001543135 | NA | NA |
| 5 | 3 | N/A | 0 | NA | NA |
| 5 | 4 | N/A | 0.000155985 | NA | NA |
| 5 | 5 | N/A | −0.000498866 | NA | NA |
| 5 | 6 | N/A | −0.000357041 | NA | NA |
| 6 | 0 | cg06126421 | −1.865398745 | 1 | 2 |
| 6 | 1 | N/A | 0.001821373 | NA | NA |
| 6 | 2 | cg10321156 | −2.435878931 | 3 | 4 |
| 6 | 3 | N/A | 0.004048751 | NA | NA |
| 6 | 4 | N/A | 0 | NA | NA |
| 6 | 5 | N/A | 3.2494E−05 | NA | NA |
| 6 | 6 | N/A | 7.86496E−05 | NA | NA |
| 7 | 0 | cg01612140 | −1.622756729 | 1 | 5 |
| 7 | 1 | cg10321156 | 0.854123211 | 2 | 3 |
| 7 | 2 | N/A | −0.002777712 | NA | NA |
| 7 | 3 | N/A | 0 | NA | NA |
| 7 | 4 | N/A | −0.001243752 | NA | NA |
| 7 | 5 | N/A | −0.002970165 | NA | NA |
| 7 | 6 | N/A | −0.002879728 | NA | NA |
| 8 | 0 | cg05575921 | −1.485199322 | 1 | 5 |
| 8 | 1 | cg26987613 | −0.749524311 | 2 | 3 |
| 8 | 2 | N/A | 0.002793775 | NA | NA |
| 8 | 3 | N/A | 0 | NA | NA |
| 8 | 4 | N/A | 0.000808724 | NA | NA |
| 8 | 5 | N/A | −0.000504924 | NA | NA |
| 8 | 6 | N/A | −0.000426865 | NA | NA |
| 9 | 0 | cg01612140 | −2.010463982 | 1 | 2 |
| 9 | 1 | N/A | 0.004582827 | NA | NA |
| 9 | 2 | cg23665802 | −0.188788949 | 3 | 4 |
| 9 | 3 | N/A | 0.000453699 | NA | NA |
| 9 | 4 | N/A | 0 | NA | NA |
| 9 | 5 | N/A | 0.000184304 | NA | NA |
| 9 | 6 | N/A | 0.000273719 | NA | NA |
| 10 | 0 | cg26987613 | −1.478735034 | 1 | 2 |
| 10 | 1 | N/A | 0.001566814 | NA | NA |
| 10 | 2 | cg05575921 | −1.375427109 | 3 | 4 |
| 10 | 3 | N/A | 0.00097786 | NA | NA |
| 10 | 4 | N/A | 0 | NA | NA |
| 10 | 5 | N/A | 7.07181E−05 | NA | NA |
| 10 | 6 | N/A | 0.000159618 | NA | NA |
| 11 | 0 | cg07890785 | −1.661479935 | 1 | 2 |
| 11 | 1 | N/A | 0.001331153 | NA | NA |
| 11 | 2 | cg05575921 | −1.367006849 | 3 | 4 |
| 11 | 3 | N/A | 0.000767824 | NA | NA |
| 11 | 4 | N/A | 0 | NA | NA |
| 11 | 5 | N/A | 6.19315E−05 | NA | NA |
| 11 | 6 | N/A | 0.000125442 | NA | NA |
| 12 | 0 | cg10321156 | 1.768165239 | 1 | 5 |
| 12 | 1 | cg26987613 | −0.732994439 | 2 | 3 |
| 12 | 2 | N/A | 0.000456479 | NA | NA |
| 12 | 3 | N/A | 0 | NA | NA |
| 12 | 4 | N/A | 0.000108808 | NA | NA |
| 12 | 5 | N/A | 0.002163719 | NA | NA |
| 12 | 6 | N/A | 0.000161827 | NA | NA |
| 13 | 0 | cg05575921 | −1.516654808 | 1 | 2 |
| 13 | 1 | N/A | 0.001680784 | NA | NA |
| 13 | 2 | cg07890785 | −2.092380313 | 3 | 4 |
| 13 | 3 | N/A | 0.002604132 | NA | NA |
| 13 | 4 | N/A | 0 | NA | NA |
| 13 | 5 | N/A | 3.41806E−05 | NA | NA |
| 13 | 6 | N/A | 0.000111425 | NA | NA |
| 14 | 0 | cg10321156 | 2.083926235 | 1 | 5 |
| 14 | 1 | cg05575921 | −1.038566412 | 2 | 3 |
| 14 | 2 | N/A | 0.000594337 | NA | NA |
| 14 | 3 | N/A | 0 | NA | NA |
| 14 | 4 | N/A | 8.88904E−05 | NA | NA |
| 14 | 5 | N/A | 0.003066387 | NA | NA |
| 14 | 6 | N/A | 0.000140106 | NA | NA |
| 15 | 0 | cg06126421 | −1.845176362 | 1 | 2 |
| 15 | 1 | N/A | 0.001628247 | NA | NA |
| 15 | 2 | cg23665802 | −0.051733355 | 3 | 4 |
| 15 | 3 | N/A | 0.000378189 | NA | NA |
| 15 | 4 | N/A | 0 | NA | NA |
| 15 | 5 | N/A | 0.000178819 | NA | NA |
| 15 | 6 | N/A | 0.000230949 | NA | NA |
| 16 | 0 | cg10321156 | 1.98603389 | 1 | 5 |
| 16 | 1 | cg07890785 | 0.10287202 | 2 | 3 |
| 16 | 2 | N/A | 0.000367198 | NA | NA |
| 16 | 3 | N/A | 0 | NA | NA |
| 16 | 4 | N/A | 0.000193247 | NA | NA |
| 16 | 5 | N/A | 0.002966471 | NA | NA |
| 16 | 6 | N/A | 0.000243117 | NA | NA |
| 17 | 0 | cg07890785 | −1.706044626 | 1 | 2 |
| 17 | 1 | N/A | 0.001682819 | NA | NA |
| 17 | 2 | cg05575921 | −1.831590797 | 3 | 4 |
| 17 | 3 | N/A | 0.00174109 | NA | NA |
| 17 | 4 | N/A | 0 | NA | NA |
| 17 | 5 | N/A | 4.25694E−05 | NA | NA |
| 17 | 6 | N/A | 0.000109257 | NA | NA |
| 18 | 0 | cg10321156 | −2.77326559 | 1 | 2 |
| 18 | 1 | N/A | 0.005372563 | NA | NA |
| 18 | 2 | cg01612140 | −2.050994185 | 3 | 4 |
| 18 | 3 | N/A | 0.002092323 | NA | NA |
| 18 | 4 | N/A | 0 | NA | NA |
| 18 | 5 | N/A | 4.29025E−05 | NA | NA |
| 18 | 6 | N/A | 8.87401E−05 | NA | NA |
| 19 | 0 | cg07890785 | −2.227502346 | 1 | 2 |
| 19 | 1 | N/A | 0.00437303 | NA | NA |
| 19 | 2 | cg05575921 | −1.726788735 | 3 | 4 |
| 19 | 3 | N/A | 0.002156873 | NA | NA |
| 19 | 4 | N/A | 0 | NA | NA |
| 19 | 5 | N/A | 3.57493E−05 | NA | NA |
| 19 | 6 | N/A | 7.64431E−05 | NA | NA |
| 20 | 0 | cg06126421 | −1.848154262 | 1 | 2 |
| 20 | 1 | N/A | 0.002023811 | NA | NA |
| 20 | 2 | cg23665802 | −0.389244059 | 3 | 4 |
| 20 | 3 | N/A | 0.000404368 | NA | NA |
| 20 | 4 | N/A | 0 | NA | NA |
| 20 | 5 | N/A | 0.000140311 | NA | NA |
| 20 | 6 | N/A | 0.000190381 | NA | NA |
| 21 | 0 | cg05575921 | −1.748965079 | 1 | 2 |
| 21 | 1 | N/A | 0.00202267 | NA | NA |
| 21 | 2 | cg07890785 | −2.208539209 | 3 | 4 |
| 21 | 3 | N/A | 0.005646196 | NA | NA |
| 21 | 4 | N/A | 0 | NA | NA |
| 21 | 5 | N/A | 4.54239E−05 | NA | NA |
| 21 | 6 | N/A | 0.000101077 | NA | NA |
| 22 | 0 | cg06126421 | −1.237216067 | 1 | 5 |
| 22 | 1 | cg10321156 | 1.75849781 | 2 | 3 |
| 22 | 2 | N/A | −0.003625867 | NA | NA |
| 22 | 3 | N/A | 0 | NA | NA |
| 22 | 4 | N/A | −0.00335528 | NA | NA |
| 22 | 5 | N/A | −0.004200167 | NA | NA |
| 22 | 6 | N/A | −0.004111649 | NA | NA |
| 23 | 0 | cg26987613 | −0.716379486 | 1 | 2 |
| 23 | 1 | N/A | 0.000691864 | NA | NA |

TABLE 14-continued

| tree | node | SplitVar | SplitCodePred | LeftNode | RightNode |
|---|---|---|---|---|---|
| 23 | 2 | cg05575921 | −1.827012706 | 3 | 4 |
| 23 | 3 | N/A | 0.002004422 | NA | NA |
| 23 | 4 | N/A | 0 | NA | NA |
| 23 | 5 | N/A | 4.00042E−05 | NA | NA |
| 23 | 6 | N/A | 0.000206664 | NA | NA |
| 24 | 0 | cg01612140 | −1.799958654 | 1 | 2 |
| 24 | 1 | N/A | 0.002254089 | NA | NA |
| 24 | 2 | cg26987613 | −1.069698342 | 3 | 4 |
| 24 | 3 | N/A | 0.000528239 | NA | NA |
| 24 | 4 | N/A | 0 | NA | NA |
| 24 | 5 | N/A | 7.55841E−05 | NA | NA |
| 24 | 6 | N/A | 0.000135199 | NA | NA |
| 25 | 0 | cg26987613 | −1.274543944 | 1 | 2 |
| 25 | 1 | N/A | 0.000963964 | NA | NA |
| 25 | 2 | cg25983901 | −1.915116671 | 3 | 4 |
| 25 | 3 | N/A | 0.002188615 | NA | NA |
| 25 | 4 | N/A | 0 | NA | NA |
| 25 | 5 | N/A | 3.63494E−05 | NA | NA |
| 25 | 6 | N/A | 0.00013426 | NA | NA |
| 26 | 0 | cg10321156 | 2.083926235 | 1 | 5 |
| 26 | 1 | cg05575921 | −1.284175684 | 2 | 3 |
| 26 | 2 | N/A | 0.000857413 | NA | NA |
| 26 | 3 | N/A | 0 | NA | NA |
| 26 | 4 | N/A | 7.20744E−05 | NA | NA |
| 26 | 5 | N/A | 0.003090594 | NA | NA |
| 26 | 6 | N/A | 0.000114555 | NA | NA |
| 27 | 0 | cg23665802 | −0.192138015 | 1 | 5 |
| 27 | 1 | cg26987613 | −1.502139413 | 2 | 3 |
| 27 | 2 | N/A | 0.001273901 | NA | NA |
| 27 | 3 | N/A | 0 | NA | NA |
| 27 | 4 | N/A | 0.00013194 | NA | NA |
| 27 | 5 | N/A | −0.000331036 | NA | NA |
| 27 | 6 | N/A | −0.000128326 | NA | NA |
| 28 | 0 | cg06126421 | −1.860528711 | 1 | 2 |
| 28 | 1 | N/A | −0.001396229 | NA | NA |
| 28 | 2 | cg10321156 | 2.483310842 | 3 | 4 |
| 28 | 3 | N/A | −0.003092413 | NA | NA |
| 28 | 4 | N/A | 0 | NA | NA |
| 28 | 5 | N/A | −0.003067554 | NA | NA |
| 28 | 6 | N/A | −0.003021818 | NA | NA |
| 29 | 0 | cg06126421 | −1.862985997 | 1 | 2 |
| 29 | 1 | N/A | 0.001378198 | NA | NA |
| 29 | 2 | cg10321156 | −2.510975891 | 3 | 4 |
| 29 | 3 | N/A | 0.002507675 | NA | NA |
| 29 | 4 | N/A | 0 | NA | NA |
| 29 | 5 | N/A | 2.03215E−05 | NA | NA |
| 29 | 6 | N/A | 6.80967E−05 | NA | NA |
| 30 | 0 | cg00252813 | −2.175046889 | 1 | 2 |
| 30 | 1 | N/A | 0.002630768 | NA | NA |
| 30 | 2 | cg05575921 | −1.481465628 | 3 | 4 |
| 30 | 3 | N/A | 0.001110387 | NA | NA |
| 30 | 4 | N/A | 0 | NA | NA |
| 30 | 5 | N/A | 5.48558E−05 | NA | NA |
| 30 | 6 | N/A | 0.000103192 | NA | NA |
| 31 | 0 | cg10321156 | 2.207117964 | 1 | 5 |
| 31 | 1 | cg26987613 | −0.772975662 | 2 | 3 |
| 31 | 2 | N/A | 0.000454173 | NA | NA |
| 31 | 3 | N/A | 0 | NA | NA |
| 31 | 4 | N/A | 9.83742E−05 | NA | NA |
| 31 | 5 | N/A | 0.004213176 | NA | NA |
| 31 | 6 | N/A | 0.000143415 | NA | NA |
| 32 | 0 | cg10321156 | 2.019226221 | 1 | 5 |
| 32 | 1 | cg10321156 | −2.898039739 | 2 | 3 |
| 32 | 2 | N/A | 0.003893383 | NA | NA |
| 32 | 3 | N/A | 0 | NA | NA |
| 32 | 4 | N/A | 3.0949E−05 | NA | NA |
| 32 | 5 | N/A | 0.002923277 | NA | NA |
| 32 | 6 | N/A | 7.84384E−05 | NA | NA |
| 33 | 0 | cg01612140 | −2.162433932 | 1 | 2 |
| 33 | 1 | N/A | 0.002986289 | NA | NA |
| 33 | 2 | cg05575921 | −1.286314212 | 3 | 4 |
| 33 | 3 | N/A | 0.000759113 | NA | NA |
| 33 | 4 | N/A | 0 | NA | NA |
| 33 | 5 | N/A | 6.85186E−05 | NA | NA |
| 33 | 6 | N/A | 0.000105019 | NA | NA |
| 34 | 0 | cg06126421 | −2.063538409 | 1 | 2 |
| 34 | 1 | N/A | −0.000377568 | NA | NA |
| 34 | 2 | cg10321156 | 2.133075053 | 3 | 4 |
| 34 | 3 | N/A | −0.002659797 | NA | NA |
| 34 | 4 | N/A | 0 | NA | NA |
| 34 | 5 | N/A | −0.002628032 | NA | NA |
| 34 | 6 | N/A | −0.002587563 | NA | NA |
| 35 | 0 | cg06126421 | −1.36253456 | 1 | 2 |
| 35 | 1 | N/A | 0.001064817 | NA | NA |
| 35 | 2 | cg07890785 | −1.702461225 | 3 | 4 |
| 35 | 3 | N/A | 0.001241449 | NA | NA |
| 35 | 4 | N/A | 0 | NA | NA |
| 35 | 5 | N/A | 4.79118E−05 | NA | NA |
| 35 | 6 | N/A | 0.000137756 | NA | NA |
| 36 | 0 | cg23665802 | −0.343512194 | 1 | 5 |
| 36 | 1 | cg10321156 | 2.100959905 | 2 | 3 |
| 36 | 2 | N/A | −0.002537667 | NA | NA |
| 36 | 3 | N/A | 0 | NA | NA |
| 36 | 4 | N/A | −0.002450723 | NA | NA |
| 36 | 5 | N/A | −0.002888706 | NA | NA |
| 36 | 6 | N/A | −0.002728786 | NA | NA |
| 37 | 0 | cg23665802 | −0.39277622 | 1 | 5 |
| 37 | 1 | cg26987613 | −0.992615735 | 2 | 3 |
| 37 | 2 | N/A | 0.000839119 | NA | NA |
| 37 | 3 | N/A | 0 | NA | NA |
| 37 | 4 | N/A | 0.000245916 | NA | NA |
| 37 | 5 | N/A | −0.000270871 | NA | NA |
| 37 | 6 | N/A | −9.02579E−05 | NA | NA |
| 38 | 0 | cg10321156 | 1.841772607 | 1 | 5 |
| 38 | 1 | cg26987613 | −1.276505132 | 2 | 3 |
| 38 | 2 | N/A | 0.000808911 | NA | NA |
| 38 | 3 | N/A | 0 | NA | NA |
| 38 | 4 | N/A | 7.66679E−05 | NA | NA |
| 38 | 5 | N/A | 0.001987481 | NA | NA |
| 38 | 6 | N/A | 0.000127464 | NA | NA |
| 39 | 0 | cg07890785 | −1.671807081 | 1 | 2 |
| 39 | 1 | N/A | −0.000387934 | NA | NA |
| 39 | 2 | cg10321156 | 1.9770277 | 3 | 4 |
| 39 | 3 | N/A | −0.001578982 | NA | NA |
| 39 | 4 | N/A | 0 | NA | NA |
| 39 | 5 | N/A | −0.001558171 | NA | NA |
| 39 | 6 | N/A | −0.001498699 | NA | NA |
| 40 | 0 | cg01612140 | −2.030498741 | 1 | 2 |
| 40 | 1 | N/A | 0.002032197 | NA | NA |
| 40 | 2 | cg25983901 | −1.294801631 | 3 | 4 |
| 40 | 3 | N/A | 0.000729685 | NA | NA |
| 40 | 4 | N/A | 0 | NA | NA |
| 40 | 5 | N/A | 6.14903E−05 | NA | NA |
| 40 | 6 | N/A | 0.000112337 | NA | NA |
| 41 | 0 | cg06126421 | −1.899094314 | 1 | 2 |
| 41 | 1 | N/A | 0.001502628 | NA | NA |
| 41 | 2 | cg07890785 | −2.071371529 | 3 | 4 |
| 41 | 3 | N/A | 0.002065489 | NA | NA |
| 41 | 4 | N/A | 0 | NA | NA |
| 41 | 5 | N/A | 2.33577E−05 | NA | NA |
| 41 | 6 | N/A | 7.07776E−05 | NA | NA |
| 42 | 0 | cg05575921 | −1.531179182 | 1 | 2 |
| 42 | 1 | N/A | 0.000726945 | NA | NA |
| 42 | 2 | cg10321156 | 1.024752837 | 3 | 4 |
| 42 | 3 | N/A | −0.000553381 | NA | NA |
| 42 | 4 | N/A | 0 | NA | NA |
| 42 | 5 | N/A | −0.000477178 | NA | NA |
| 42 | 6 | N/A | −0.000421632 | NA | NA |
| 43 | 0 | cg01612140 | −1.992252214 | 1 | 2 |
| 43 | 1 | N/A | 0.00273982 | NA | NA |
| 43 | 2 | cg07890785 | −2.061479882 | 3 | 4 |
| 43 | 3 | N/A | 0.002196901 | NA | NA |
| 43 | 4 | N/A | 0 | NA | NA |
| 43 | 5 | N/A | 2.80083E−05 | NA | NA |
| 43 | 6 | N/A | 7.88945E−05 | NA | NA |
| 44 | 0 | cg05575921 | −1.835425911 | 1 | 2 |
| 44 | 1 | N/A | 0.002137997 | NA | NA |
| 44 | 2 | cg07890785 | −1.661479935 | 3 | 4 |
| 44 | 3 | N/A | 0.000824945 | NA | NA |
| 44 | 4 | N/A | 0 | NA | NA |
| 44 | 5 | N/A | 4.94571E−05 | NA | NA |
| 44 | 6 | N/A | 9.51797E−05 | NA | NA |
| 45 | 0 | cg01612140 | −1.799421907 | 1 | 2 |
| 45 | 1 | N/A | 0.00159686 | NA | NA |
| 45 | 2 | cg06126421 | −1.860528711 | 3 | 4 |
| 45 | 3 | N/A | 0.00136923 | NA | NA |

TABLE 14-continued

| tree | node | SplitVar | SplitCodePred | LeftNode | RightNode |
|---|---|---|---|---|---|
| 45 | 4 | N/A | 0 | NA | NA |
| 45 | 5 | N/A | 3.10433E-05 | NA | NA |
| 45 | 6 | N/A | 8.49103E-05 | NA | NA |
| 46 | 0 | cg26987613 | -1.367694176 | 1 | 5 |
| 46 | 1 | cg05575921 | 0.385396141 | 2 | 3 |
| 46 | 2 | N/A | 0.002007155 | NA | NA |
| 46 | 3 | N/A | 0 | NA | NA |
| 46 | 4 | N/A | 0.001416815 | NA | NA |
| 46 | 5 | N/A | 0.00025109 | NA | NA |
| 46 | 6 | N/A | 0.000328562 | NA | NA |
| 47 | 0 | cg05575921 | -1.516654808 | 1 | 5 |
| 47 | 1 | cg26987613 | -0.073139136 | 2 | 3 |
| 47 | 2 | N/A | 0.002620939 | NA | NA |
| 47 | 3 | N/A | 0 | NA | NA |
| 47 | 4 | N/A | 0.001606382 | NA | NA |
| 47 | 5 | N/A | -3.18352E-05 | NA | NA |
| 47 | 6 | N/A | 4.7578E-05 | NA | NA |
| 48 | 0 | cg05575921 | -1.948073675 | 1 | 2 |
| 48 | 1 | N/A | 0.004088278 | NA | NA |
| 48 | 2 | cg26987613 | -0.634523811 | 3 | 4 |
| 48 | 3 | N/A | 0.000436505 | NA | NA |
| 48 | 4 | N/A | 0 | NA | NA |
| 48 | 5 | N/A | 0.000112925 | NA | NA |
| 48 | 6 | N/A | 0.000159548 | NA | NA |
| 49 | 0 | cg25983901 | -1.06417788 | 1 | 5 |
| 49 | 1 | cg05575921 | -1.402867011 | 2 | 3 |
| 49 | 2 | N/A | 0.003607995 | NA | NA |
| 49 | 3 | N/A | 0 | NA | NA |
| 49 | 4 | N/A | 0.000366915 | NA | NA |
| 49 | 5 | N/A | -0.000492645 | NA | NA |
| 49 | 6 | N/A | -0.000373691 | NA | NA |
| 50 | 0 | cg05575921 | -1.406473813 | 1 | 2 |
| 50 | 1 | N/A | 0.001153449 | NA | NA |
| 50 | 2 | cg26987613 | -1.483701738 | 3 | 4 |
| 50 | 3 | N/A | 0.000909268 | NA | NA |
| 50 | 4 | N/A | 0 | NA | NA |
| 50 | 5 | N/A | 4.82131E-05 | NA | NA |
| 50 | 6 | N/A | 0.000110431 | NA | NA |
| 51 | 0 | cg06126421 | -1.860528711 | 1 | 2 |
| 51 | 1 | N/A | -0.000429545 | NA | NA |
| 51 | 2 | cg10321156 | 1.994005054 | 3 | 4 |
| 51 | 3 | N/A | -0.002046055 | NA | NA |
| 51 | 4 | N/A | 0 | NA | NA |
| 51 | 5 | N/A | -0.002014654 | NA | NA |
| 51 | 6 | N/A | -0.001963841 | NA | NA |
| 52 | 0 | cg10321156 | 0.702238895 | 1 | 2 |
| 52 | 1 | N/A | -0.000457334 | NA | NA |
| 52 | 2 | cg01612140 | -1.663178338 | 3 | 4 |
| 52 | 3 | N/A | 0.001885186 | NA | NA |
| 52 | 4 | N/A | 0 | NA | NA |
| 52 | 5 | N/A | 0.000208144 | NA | NA |
| 52 | 6 | N/A | -0.000292396 | NA | NA |
| 53 | 0 | cg06126421 | -1.35461919 | 1 | 5 |
| 53 | 1 | cg10321156 | 1.543045709 | 2 | 3 |
| 53 | 2 | N/A | -0.004241272 | NA | NA |
| 53 | 3 | N/A | 0 | NA | NA |
| 53 | 4 | N/A | -0.00354976 | NA | NA |
| 53 | 5 | N/A | -0.004956803 | NA | NA |
| 53 | 6 | N/A | -0.004855593 | NA | NA |
| 54 | 0 | cg10321156 | 1.994012306 | 1 | 5 |
| 54 | 1 | cg07890785 | -1.764606037 | 2 | 3 |
| 54 | 2 | N/A | 0.001890893 | NA | NA |
| 54 | 3 | N/A | 0 | NA | NA |
| 54 | 4 | N/A | 5.29027E-05 | NA | NA |
| 54 | 5 | N/A | 0.002201456 | NA | NA |
| 54 | 6 | N/A | 9.9939E-05 | NA | NA |
| 55 | 0 | cg01612140 | -1.806811794 | 1 | 2 |
| 55 | 1 | N/A | 0.001898579 | NA | NA |
| 55 | 2 | cg25983901 | -1.814044594 | 3 | 4 |
| 55 | 3 | N/A | 0.001565955 | NA | NA |
| 55 | 4 | N/A | 0 | NA | NA |
| 55 | 5 | N/A | 4.16746E-05 | NA | NA |
| 55 | 6 | N/A | 9.82964E-05 | NA | NA |
| 56 | 0 | cg10321156 | 1.9770277 | 1 | 5 |
| 56 | 1 | cg23665802 | -0.15614071 | 2 | 3 |
| 56 | 2 | N/A | 0.000441415 | NA | NA |
| 56 | 3 | N/A | 0 | NA | NA |
| 56 | 4 | N/A | 0.000189278 | NA | NA |
| 56 | 5 | N/A | 0.00250599 | NA | NA |
| 56 | 6 | N/A | 0.000229128 | NA | NA |
| 57 | 0 | cg10321156 | 1.24859261 | 1 | 2 |
| 57 | 1 | N/A | -0.000286164 | NA | NA |
| 57 | 2 | cg26987613 | -0.927261807 | 3 | 4 |
| 57 | 3 | N/A | 0.002095285 | NA | NA |
| 57 | 4 | N/A | 0 | NA | NA |
| 57 | 5 | N/A | 0.000698428 | NA | NA |
| 57 | 6 | N/A | -0.000198405 | NA | NA |
| 58 | 0 | cg10321156 | 2.211474903 | 1 | 5 |
| 58 | 1 | cg26987613 | -0.626175102 | 2 | 3 |
| 58 | 2 | N/A | 0.000511606 | NA | NA |
| 58 | 3 | N/A | 0 | NA | NA |
| 58 | 4 | N/A | 0.00013883 | NA | NA |
| 58 | 5 | N/A | 0.003398737 | NA | NA |
| 58 | 6 | N/A | 0.000177062 | NA | NA |
| 59 | 0 | cg07890785 | -2.227502346 | 1 | 2 |
| 59 | 1 | N/A | 0.004088172 | NA | NA |
| 59 | 2 | cg05575921 | -1.482581486 | 3 | 4 |
| 59 | 3 | N/A | 0.001069649 | NA | NA |
| 59 | 4 | N/A | 0 | NA | NA |
| 59 | 5 | N/A | 6.16293E-05 | NA | NA |
| 59 | 6 | N/A | 9.94077E-05 | NA | NA |
| 60 | 0 | cg10321156 | 2.082225047 | 1 | 5 |
| 60 | 1 | cg10321156 | 1.007108695 | 2 | 3 |
| 60 | 2 | N/A | -0.000564754 | NA | NA |
| 60 | 3 | N/A | 0 | NA | NA |
| 60 | 4 | N/A | -0.00048644 | NA | NA |
| 60 | 5 | N/A | 0.00293207 | NA | NA |
| 60 | 6 | N/A | -0.000441002 | NA | NA |
| 61 | 0 | cg06126421 | -2.135812285 | 1 | 2 |
| 61 | 1 | N/A | 0.002452159 | NA | NA |
| 61 | 2 | cg01612140 | -2.035591826 | 3 | 4 |
| 61 | 3 | N/A | 0.002017192 | NA | NA |
| 61 | 4 | N/A | 0 | NA | NA |
| 61 | 5 | N/A | 2.88628E-05 | NA | NA |
| 61 | 6 | N/A | 6.86511E-05 | NA | NA |
| 62 | 0 | cg07890785 | -0.037591496 | 1 | 5 |
| 62 | 1 | cg10321156 | 1.974138935 | 2 | 3 |
| 62 | 2 | N/A | -0.001808339 | NA | NA |
| 62 | 3 | N/A | 0 | NA | NA |
| 62 | 4 | N/A | -0.001740947 | NA | NA |
| 62 | 5 | N/A | -0.002192967 | NA | NA |
| 62 | 6 | N/A | -0.001965366 | NA | NA |
| 63 | 0 | cg25983901 | -1.033230774 | 1 | 5 |
| 63 | 1 | cg05575921 | -1.528275408 | 2 | 3 |
| 63 | 2 | N/A | 0.003252367 | NA | NA |
| 63 | 3 | N/A | 0 | NA | NA |
| 63 | 4 | N/A | 0.000342354 | NA | NA |
| 63 | 5 | N/A | -0.000504101 | NA | NA |
| 63 | 6 | N/A | -0.000378357 | NA | NA |
| 64 | 0 | cg07890785 | -0.208611829 | 1 | 5 |
| 64 | 1 | cg10321156 | 1.024578129 | 2 | 3 |
| 64 | 2 | N/A | -0.000743477 | NA | NA |
| 64 | 3 | N/A | 0 | NA | NA |
| 64 | 4 | N/A | -0.000574745 | NA | NA |
| 64 | 5 | N/A | -0.000989827 | NA | NA |
| 64 | 6 | N/A | -0.000806788 | NA | NA |
| 65 | 0 | cg05575921 | -1.832590967 | 1 | 2 |
| 65 | 1 | N/A | 0.002961298 | NA | NA |
| 65 | 2 | cg26987613 | -1.282999915 | 3 | 4 |
| 65 | 3 | N/A | 0.00090817 | NA | NA |
| 65 | 4 | N/A | 0 | NA | NA |
| 65 | 5 | N/A | 8.40764E-05 | NA | NA |
| 65 | 6 | N/A | 0.000142566 | NA | NA |
| 66 | 0 | cg01612140 | -2.109105949 | 1 | 2 |
| 66 | 1 | N/A | 0.003361607 | NA | NA |
| 66 | 2 | cg26987613 | -1.479716215 | 3 | 4 |
| 66 | 3 | N/A | 0.001022099 | NA | NA |
| 66 | 4 | N/A | 0 | NA | NA |
| 66 | 5 | N/A | 4.95613E-05 | NA | NA |
| 66 | 6 | N/A | 0.000103942 | NA | NA |
| 67 | 0 | cg07890785 | -1.937914423 | 1 | 2 |
| 67 | 1 | N/A | 0.002485363 | NA | NA |
| 67 | 2 | cg23665802 | -0.165960102 | 3 | 4 |
| 67 | 3 | N/A | 0.000389787 | NA | NA |
| 67 | 4 | N/A | 0 | NA | NA |
| 67 | 5 | N/A | 0.000171718 | NA | NA |

TABLE 14-continued

| tree | node | SplitVar | SplitCodePred | LeftNode | RightNode |
|---|---|---|---|---|---|
| 67 | 6 | N/A | 0.000218751 | NA | NA |
| 68 | 0 | cg01612140 | −1.678024026 | 1 | 2 |
| 68 | 1 | N/A | 0.001343309 | NA | NA |
| 68 | 2 | cg10321156 | −2.77326559 | 3 | 4 |
| 68 | 3 | N/A | 0.002610566 | NA | NA |
| 68 | 4 | N/A | 0 | NA | NA |
| 68 | 5 | N/A | 2.14685E−05 | NA | NA |
| 68 | 6 | N/A | 8.65787E−05 | NA | NA |
| 69 | 0 | cg05575921 | −1.279045166 | 1 | 2 |
| 69 | 1 | N/A | 0.000878233 | NA | NA |
| 69 | 2 | cg07890785 | −1.671807081 | 3 | 4 |
| 69 | 3 | N/A | 0.001208205 | NA | NA |
| 69 | 4 | N/A | 0 | NA | NA |
| 69 | 5 | N/A | 5.08609E−05 | NA | NA |
| 69 | 6 | N/A | 0.000125253 | NA | NA |
| 70 | 0 | cg10321156 | 0.720950493 | 1 | 5 |
| 70 | 1 | cg10321156 | −2.017121098 | 2 | 3 |
| 70 | 2 | N/A | 0.001282509 | NA | NA |
| 70 | 3 | N/A | 0 | NA | NA |
| 70 | 4 | N/A | 5.18857E−05 | NA | NA |
| 70 | 5 | N/A | 0.00058025 | NA | NA |
| 70 | 6 | N/A | 0.000182015 | NA | NA |
| 71 | 0 | cg07890785 | −1.668154551 | 1 | 2 |
| 71 | 1 | N/A | 0.001480615 | NA | NA |
| 71 | 2 | cg05575921 | −1.038566412 | 3 | 4 |
| 71 | 3 | N/A | 0.000607077 | NA | NA |
| 71 | 4 | N/A | 0 | NA | NA |
| 71 | 5 | N/A | 8.08444E−05 | NA | NA |
| 71 | 6 | N/A | 0.000141038 | NA | NA |
| 72 | 0 | cg01612140 | −1.785641893 | 1 | 2 |
| 72 | 1 | N/A | 0.0015925 | NA | NA |
| 72 | 2 | cg23665802 | −0.156257212 | 3 | 4 |
| 72 | 3 | N/A | 0.000413147 | NA | NA |
| 72 | 4 | N/A | 0 | NA | NA |
| 72 | 5 | N/A | 0.000178604 | NA | NA |
| 72 | 6 | N/A | 0.000237193 | NA | NA |
| 73 | 0 | cg26987613 | −1.002498848 | 1 | 5 |
| 73 | 1 | cg19572487 | 1.94112413 | 2 | 3 |
| 73 | 2 | N/A | −0.004106908 | NA | NA |
| 73 | 3 | N/A | 0 | NA | NA |
| 73 | 4 | N/A | −0.00390946 | NA | NA |
| 73 | 5 | N/A | −0.004705774 | NA | NA |
| 73 | 6 | N/A | −0.004576272 | NA | NA |
| 74 | 0 | cg10321156 | 1.97895284 | 1 | 5 |
| 74 | 1 | cg26987613 | −0.734493448 | 2 | 3 |
| 74 | 2 | N/A | 0.000499557 | NA | NA |
| 74 | 3 | N/A | 0 | NA | NA |
| 74 | 4 | N/A | 0.000115129 | NA | NA |
| 74 | 5 | N/A | 0.003103623 | NA | NA |
| 74 | 6 | N/A | 0.000173544 | NA | NA |
| 75 | 0 | cg05575921 | −1.507304114 | 1 | 5 |
| 75 | 1 | cg00252813 | −0.730185859 | 2 | 3 |
| 75 | 2 | N/A | 0.002564363 | NA | NA |
| 75 | 3 | N/A | 0 | NA | NA |
| 75 | 4 | N/A | 0.001104101 | NA | NA |
| 75 | 5 | N/A | −0.000398325 | NA | NA |
| 75 | 6 | N/A | −0.000313748 | NA | NA |
| 76 | 0 | cg06126421 | −1.860528711 | 1 | 2 |
| 76 | 1 | N/A | 0.00169914 | NA | NA |
| 76 | 2 | cg23665802 | −2.2026955 | 3 | 4 |
| 76 | 3 | N/A | 0.002973699 | NA | NA |
| 76 | 4 | N/A | 0 | NA | NA |
| 76 | 5 | N/A | 4.06047E−05 | NA | NA |
| 76 | 6 | N/A | 8.4694E−05 | NA | NA |
| 77 | 0 | cg10321156 | 0.703889128 | 1 | 2 |
| 77 | 1 | N/A | −0.000284659 | NA | NA |
| 77 | 2 | cg14975410 | −0.703245738 | 3 | 4 |
| 77 | 3 | N/A | 0.000930257 | NA | NA |
| 77 | 4 | N/A | 0 | NA | NA |
| 77 | 5 | N/A | 0.000241509 | NA | NA |
| 77 | 6 | N/A | −0.000156305 | NA | NA |
| 78 | 0 | cg26987613 | −1.165209185 | 1 | 5 |
| 78 | 1 | cg06126421 | −1.486040273 | 2 | 3 |
| 78 | 2 | N/A | 0.002080051 | NA | NA |
| 78 | 3 | N/A | 0 | NA | NA |
| 78 | 4 | N/A | 0.000334294 | NA | NA |
| 78 | 5 | N/A | −0.00057858 | NA | NA |
| 78 | 6 | N/A | −0.000458671 | NA | NA |
| 79 | 0 | cg05575921 | −1.408717357 | 1 | 2 |
| 79 | 1 | N/A | 0.001454879 | NA | NA |
| 79 | 2 | cg26987613 | −1.025380382 | 3 | 4 |
| 79 | 3 | N/A | 0.000608028 | NA | NA |
| 79 | 4 | N/A | 0 | NA | NA |
| 79 | 5 | N/A | 8.75153E−05 | NA | NA |
| 79 | 6 | N/A | 0.000177319 | NA | NA |
| 80 | 0 | cg07890785 | −2.071371529 | 1 | 2 |
| 80 | 1 | N/A | 0.002577065 | NA | NA |
| 80 | 2 | cg06126421 | −1.355215056 | 3 | 4 |
| 80 | 3 | N/A | 0.000841944 | NA | NA |
| 80 | 4 | N/A | 0 | NA | NA |
| 80 | 5 | N/A | 7.01063E−05 | NA | NA |
| 80 | 6 | N/A | 0.000105388 | NA | NA |
| 81 | 0 | cg07890785 | −1.702461225 | 1 | 2 |
| 81 | 1 | N/A | 0.00118264 | NA | NA |
| 81 | 2 | cg06126421 | −1.866579745 | 3 | 4 |
| 81 | 3 | N/A | 0.001311968 | NA | NA |
| 81 | 4 | N/A | 0 | NA | NA |
| 81 | 5 | N/A | 3.35017E−05 | NA | NA |
| 81 | 6 | N/A | 9.1902E−05 | NA | NA |
| 82 | 0 | cg05575921 | −1.213992709 | 1 | 2 |
| 82 | 1 | N/A | 0.000777797 | NA | NA |
| 82 | 2 | cg07890785 | −2.043422701 | 3 | 4 |
| 82 | 3 | N/A | 0.002384628 | NA | NA |
| 82 | 4 | N/A | 0 | NA | NA |
| 82 | 5 | N/A | 2.89799E−05 | NA | NA |
| 82 | 6 | N/A | 0.000103335 | NA | NA |
| 83 | 0 | cg10321156 | 0.722055531 | 1 | 2 |
| 83 | 1 | N/A | −0.000459953 | NA | NA |
| 83 | 2 | cg14975410 | −1.890606461 | 3 | 4 |
| 83 | 3 | N/A | 0.00349955 | NA | NA |
| 83 | 4 | N/A | 0 | NA | NA |
| 83 | 5 | N/A | 0.000135466 | NA | NA |
| 83 | 6 | N/A | −0.000315637 | NA | NA |
| 84 | 0 | cg06126421 | −1.268297994 | 1 | 5 |
| 84 | 1 | cg10321156 | 1.813204072 | 2 | 3 |
| 84 | 2 | N/A | −0.003242356 | NA | NA |
| 84 | 3 | N/A | 0 | NA | NA |
| 84 | 4 | N/A | −0.002972159 | NA | NA |
| 84 | 5 | N/A | −0.003892388 | NA | NA |
| 84 | 6 | N/A | −0.00380605 | NA | NA |
| 85 | 0 | cg06126421 | −1.322791069 | 1 | 5 |
| 85 | 1 | cg25983901 | −1.723672491 | 2 | 3 |
| 85 | 2 | N/A | 0.004109026 | NA | NA |
| 85 | 3 | N/A | 0 | NA | NA |
| 85 | 4 | N/A | 0.000418512 | NA | NA |
| 85 | 5 | N/A | −0.000777523 | NA | NA |
| 85 | 6 | N/A | −0.000676528 | NA | NA |
| 86 | 0 | cg05575921 | −1.441070385 | 1 | 5 |
| 86 | 1 | cg06126421 | −1.862985997 | 2 | 3 |
| 86 | 2 | N/A | 0.003077995 | NA | NA |
| 86 | 3 | N/A | 0 | NA | NA |
| 86 | 4 | N/A | 0.000826924 | NA | NA |
| 86 | 5 | N/A | −0.000576918 | NA | NA |
| 86 | 6 | N/A | −0.000503378 | NA | NA |
| 87 | 0 | cg10321156 | 2.082225047 | 1 | 5 |
| 87 | 1 | cg26987613 | −0.773685383 | 2 | 3 |
| 87 | 2 | N/A | 0.000525949 | NA | NA |
| 87 | 3 | N/A | 0 | NA | NA |
| 87 | 4 | N/A | 0.000113358 | NA | NA |
| 87 | 5 | N/A | 0.003089435 | NA | NA |
| 87 | 6 | N/A | 0.000152915 | NA | NA |
| 88 | 0 | cg26987613 | −1.482491254 | 1 | 2 |
| 88 | 1 | N/A | −0.001683367 | NA | NA |
| 88 | 2 | cg10321156 | 2.137151744 | 3 | 4 |
| 88 | 3 | N/A | −0.002750565 | NA | NA |
| 88 | 4 | N/A | 0 | NA | NA |
| 88 | 5 | N/A | −0.002716039 | NA | NA |
| 88 | 6 | N/A | −0.002648217 | NA | NA |
| 89 | 0 | cg10321156 | 2.100959905 | 1 | 5 |
| 89 | 1 | cg26987613 | −1.069868902 | 2 | 3 |
| 89 | 2 | N/A | 0.000575004 | NA | NA |
| 89 | 3 | N/A | 0 | NA | NA |
| 89 | 4 | N/A | 7.30743E−05 | NA | NA |
| 89 | 5 | N/A | 0.002207727 | NA | NA |
| 89 | 6 | N/A | 0.000106454 | NA | NA |
| 90 | 0 | cg05575921 | −1.832590967 | 1 | 2 |

TABLE 14-continued

| tree | node | SplitVar | SplitCodePred | LeftNode | RightNode |
|---|---|---|---|---|---|
| 90 | 1 | N/A | 0.002053304 | NA | NA |
| 90 | 2 | cg26987613 | −0.792727728 | 3 | 4 |
| 90 | 3 | N/A | 0.000541243 | NA | NA |
| 90 | 4 | N/A | 0 | NA | NA |
| 90 | 5 | N/A | 0.000113173 | NA | NA |
| 90 | 6 | N/A | 0.000152613 | NA | NA |
| 91 | 0 | cg05575921 | −0.586669464 | 1 | 5 |
| 91 | 1 | cg26987613 | −0.949715136 | 2 | 3 |
| 91 | 2 | N/A | 0.001373098 | NA | NA |
| 91 | 3 | N/A | 0 | NA | NA |
| 91 | 4 | N/A | 0.000240646 | NA | NA |
| 91 | 5 | N/A | −0.000292214 | NA | NA |
| 91 | 6 | N/A | −0.000130564 | NA | NA |
| 92 | 0 | cg05575921 | −1.403143496 | 1 | 2 |
| 92 | 1 | N/A | 0.001109359 | NA | NA |
| 92 | 2 | cg10321156 | −2.016278277 | 3 | 4 |
| 92 | 3 | N/A | 0.001720153 | NA | NA |
| 92 | 4 | N/A | 0 | NA | NA |
| 92 | 5 | N/A | 3.75832E−05 | NA | NA |
| 92 | 6 | N/A | 0.000112163 | NA | NA |
| 93 | 0 | cg10321156 | 1.843601068 | 1 | 5 |
| 93 | 1 | cg07890785 | −1.561267415 | 2 | 3 |
| 93 | 2 | N/A | 0.000864791 | NA | NA |
| 93 | 3 | N/A | 0 | NA | NA |
| 93 | 4 | N/A | 4.02551E−05 | NA | NA |
| 93 | 5 | N/A | 0.001927379 | NA | NA |
| 93 | 6 | N/A | 8.89456E−05 | NA | NA |
| 94 | 0 | cg10321156 | 1.843601068 | 1 | 5 |
| 94 | 1 | cg26987613 | −2.148702451 | 2 | 3 |
| 94 | 2 | N/A | 0.002528814 | NA | NA |
| 94 | 3 | N/A | 0 | NA | NA |
| 94 | 4 | N/A | 3.04921E−05 | NA | NA |
| 94 | 5 | N/A | 0.001800608 | NA | NA |
| 94 | 6 | N/A | 7.89316E−05 | NA | NA |
| 95 | 0 | cg01612140 | −1.798701138 | 1 | 2 |
| 95 | 1 | N/A | 0.001759087 | NA | NA |
| 95 | 2 | cg05575921 | −1.481465628 | 3 | 4 |
| 95 | 3 | N/A | 0.000791559 | NA | NA |
| 95 | 4 | N/A | 0 | NA | NA |
| 95 | 5 | N/A | 5.00743E−05 | NA | NA |
| 95 | 6 | N/A | 0.00011154 | NA | NA |
| 96 | 0 | cg01612140 | −1.930674778 | 1 | 2 |
| 96 | 1 | N/A | 0.002982546 | NA | NA |
| 96 | 2 | cg10321156 | −2.77326559 | 3 | 4 |
| 96 | 3 | N/A | 0.003576947 | NA | NA |
| 96 | 4 | N/A | 0 | NA | NA |
| 96 | 5 | N/A | 2.85699E−05 | NA | NA |
| 96 | 6 | N/A | 9.0929E−05 | NA | NA |
| 97 | 0 | cg07890785 | −2.208539209 | 1 | 2 |
| 97 | 1 | N/A | 0.003022301 | NA | NA |
| 97 | 2 | cg01612140 | −1.806812378 | 3 | 4 |
| 97 | 3 | N/A | 0.001528506 | NA | NA |
| 97 | 4 | N/A | 0 | NA | NA |
| 97 | 5 | N/A | 4.10824E−05 | NA | NA |
| 97 | 6 | N/A | 7.37149E−05 | NA | NA |
| 98 | 0 | cg06126421 | −1.322791069 | 1 | 5 |
| 98 | 1 | cg10321156 | 1.543045709 | 2 | 3 |
| 98 | 2 | N/A | −0.003960708 | NA | NA |
| 98 | 3 | N/A | 0 | NA | NA |
| 98 | 4 | N/A | −0.003567911 | NA | NA |
| 98 | 5 | N/A | −0.004612884 | NA | NA |
| 98 | 6 | N/A | −0.004514024 | NA | NA |
| 99 | 0 | cg01612140 | −1.815647121 | 1 | 2 |
| 99 | 1 | N/A | 0.002006384 | NA | NA |
| 99 | 2 | cg23665802 | 0.077143283 | 3 | 4 |
| 99 | 3 | N/A | 0.000364383 | NA | NA |
| 99 | 4 | N/A | 0 | NA | NA |
| 99 | 5 | N/A | 0.000187472 | NA | NA |
| 99 | 6 | N/A | 0.000240091 | NA | NA |
| 100 | 0 | cg05575921 | −1.516654808 | 1 | 5 |
| 100 | 1 | cg25983901 | −1.618320922 | 2 | 3 |
| 100 | 2 | N/A | 0.007277606 | NA | NA |
| 100 | 3 | N/A | 0 | NA | NA |
| 100 | 4 | N/A | 0.001010779 | NA | NA |
| 100 | 5 | N/A | −0.000817275 | NA | NA |
| 100 | 6 | N/A | −0.000714367 | NA | NA |

What is claimed is:

1. A computer system comprising a computer processor and a non-transitory computer readable storage medium storing instructions that, when executed by the processor, cause the processor to:
    access a training set of methylation fraction values for m methylation sites relating to j training subjects;
    train a machine-learned model using the accessed training set of methylation fraction values, the trained machine-learned model comprising a set of weights determined based on a classification of each methylation fraction value within the accessed training set of methylation fraction values indicating whether a sample associated with the methylation fraction value survived, the trained machine-learned model configured to predict one or more survival metrics based on methylation fraction values;
    access methylation fraction values for n nucleic acid methylation sites relating to a test subject; and
    apply the trained machine-learned model to the accessed methylation fraction values for the n nucleic acid methylation sites to generate a survival metric for the test subject based on the accessed methylation fraction values for the n nucleic acid methylation sites, wherein the survival metric represents a likelihood that the test subject will survive over an interval of time.

2. The computer system of claim 1, wherein the machine-learned model is nonlinear.

3. The computer system of claim 1, where the machine-learned model is trained with a Cox proportional hazard loss function.

4. The computer system of claim 1, wherein the machine-learned model is trained by gradient boosting.

5. The computer system of claim 1, wherein the machine-learned model is trained using elastic net regression.

6. The computer system of claim 1, wherein the training set further comprises values for k clinical factors.

7. The computer system claim of claim 6, wherein the k clinical factors are selected from a group consisting of age, sex, systolic blood pressure, diastolic blood pressure, high cholesterol status, cardiovascular disease status, high blood sugar status, smoking status, alcohol consumption status, a number of cigarettes smoked per day, period lived as a smoker, frequency of alcohol consumption, daily amount of alcohol consumption, time spent engaging in mild physical activity, time spent engaging in moderate physical activity, time spent engaging in heavy physical activity, race, ethnicity, diastolic blood pressure, systolic blood pressure, height, weight, a body mass index, resting heart rate, a family history parameter, a medical history parameter, and a medical symptom parameter.

8. The computer system of claim 1, wherein the machine-learned model is further configured to accept values for l clinical factors and to generate survival metrics for i test subjects based on the l clinical factors.

9. The computer system of claim 8, wherein the l clinical factors are selected from a group consisting of age, sex, systolic blood pressure, diastolic blood pressure, high cholesterol status, cardiovascular disease status, high blood sugar status, smoking status, alcohol consumption status, a number of cigarettes smoked per day, period lived as a smoker, frequency of alcohol consumption, daily amount of alcohol consumption, time spent engaging in mild physical activity, time spent engaging in moderate physical activity, time spent engaging in heavy physical activity, race, ethnicity, diastolic blood pressure, systolic blood pressure, height, weight, a body mass index, resting heart rate, a family history parameter, a medical history parameter, and a medical symptom parameter.

10. The computer system of claim 1, wherein the methylation fraction values for the n nucleic acid methylation sites are derived from a blood sample.

11. The computer system of claim 1, wherein the training set consists of methylation fraction values for subjects having a preset value for a screening clinical factor.

12. The computer system of claim 11, wherein the screening clinical factor is gender.

13. The computer system of claim 1, wherein the survival metric is indicative of the test subject's relative survival risk.

14. The computer system of claim 13, wherein the survival metric is indicative of the test subject's relative likelihood of contracting an aging-related disease, chance of survival, or chance of death.

15. The computer system of claim 1, wherein the n nucleic acid methylation sites applied to the machine-learned model comprise y nucleic acid methylation sites identified using a first dataset of nucleic acid methylation sites and a first modeling technique, and n−y nucleic acid methylation sites identified using a second dataset of nucleic acid methylation sites and a second modeling technique.

16. The computer system of claim 15, wherein the first dataset is different from the second dataset, wherein the first modeling technique is different from the second modeling technique, or combinations thereof.

17. The computer system of claim 1, wherein the nucleic acid methylation sites include at least two or more of cg01612140, cg05575921, cg06126421, cg08362785, cg10321156, cg14975410, cg19572487, cg23665802, cg24704287, cg25983901, cg26987613, cg00252813, cg07890785, cg02679745, cg15814508, cg20430631, and cg00984060.

18. The computer system of claim 1, wherein the nucleic acid methylation sites include at least two or more of the nucleic acid methylation sites of Tables 1, 2, 3, 4, 5, 6, 7, 8, 9, 10 or 11.

19. A method for predicting survival likelihood comprising:
accessing a training set of methylation fraction values for m methylation sites relating to j training subjects;
training a machine-learned model using the accessed training set of methylation fraction values, the trained machine-learned model comprising a set of weights determined based on a classification of each methylation fraction value within the accessed training set of methylation fraction values indicating whether a sample associated with the methylation fraction value survived, the trained machine-learned model configured to predict one or more survival metrics based on methylation fraction values;
accessing methylation fraction values for n nucleic acid methylation sites relating to a test subject; and
applying the trained machine-learned model to the accessed methylation fraction values for the n nucleic acid methylation sites to generate a survival metric for the test subject based on the accessed methylation fraction values for the n nucleic acid methylation sites, wherein the survival metric represents a likelihood that the test subject will survive over an interval of time.

* * * * *

UNITED STATES PATENT AND TRADEMARK OFFICE
CERTIFICATE OF CORRECTION

PATENT NO. : 11,445,981 B1
APPLICATION NO. : 16/040615
DATED : September 20, 2022
INVENTOR(S) : Kristen Patricia Fortney et al.

Page 1 of 1

It is certified that error appears in the above-identified patent and that said Letters Patent is hereby corrected as shown below:

On the Title Page

Item (73), under Assignee, Lines 1-2, delete "BioAge Labs, Ipc., Richmond, CA" and insert
-- BioAge Labs, Inc., Richmond, CA --, therefor.

In the Claims

In Column 60, Claim 7, Line 39, delete "system claim of" and insert -- system of --, therefor.

Signed and Sealed this
Twenty-seventh Day of December, 2022

Katherine Kelly Vidal
Director of the United States Patent and Trademark Office